(12) United States Patent
Carr

(10) Patent No.: US 6,632,936 B2
(45) Date of Patent: *Oct. 14, 2003

(54) CELL-CYCLE CHECKPOINT GENES

(76) Inventor: Antony Michael Carr, MRC Cell Mutation Unit, University of Sussex, Falmer Brighton BN1 9RR (GB)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/029,047
(22) PCT Filed: Sep. 6, 1996
(86) PCT No.: PCT/GB96/02197
§ 371 (c)(1), (2), (4) Date: May 11, 1999
(87) PCT Pub. No.: WO97/09433
PCT Pub. Date: Mar. 13, 1997

(65) Prior Publication Data
US 2003/0007975 A1 Jan. 9, 2003

(30) Foreign Application Priority Data
Sep. 6, 1995 (GB) .............................. 9518220

(51) Int. Cl.⁷ ........................ C07H 21/04; C07H 21/02; C12Q 1/68; C12P 21/06; C12N 15/00
(52) U.S. Cl. ........................ 536/23.5; 536/23.1; 435/6; 435/325; 435/320.1; 435/69.1
(58) Field of Search .............................. 435/320.1, 69.1, 435/6, 536, 23.5, 325; 536/23.1

(56) References Cited

U.S. PATENT DOCUMENTS
5,912,143 A * 6/1999 Bandman et al.

FOREIGN PATENT DOCUMENTS
WO   WO 89/03891   5/1989
WO   WO 90/13667   11/1990

OTHER PUBLICATIONS

Bowie et al (Science, 1990, 257:1306–1310).*
Burgess et al (J of Cell Bio. 111:2129–2138, 1990).*
Lazar et al (Molecular and Cellular Biology, 1988, 8:1247–1252).*
Reiger et al (Glossary of Genetics and Cytogenetics, Classical and Molecular, 4th Ed., Springer–Verlay, Berlin, 1976).*
Sumitomo Chem. Co. (Q47789), Genbank Sequence Database, National Center for Biotechnology Information, National Library of Medicine, Bethesda, Maryland, publicly available Mar. 2, 1994.*
Hillier et al (R09128), Genbank Sequence Database, National Center for Biotechnology Information, National Library of Medicine, Bethesda, Maryland, publicly available Apr. 5, 1995.*
Groudine et al. (T91040) GENESEQ Database, National Center for Biotechnology Information, National Library of Medicine, Bethesda, Maryland.*
Harris et al. J. of The Am Society of Nephrology 6:1125–33, 1995.*
Ahn et al. Nature Genetics 3(4):283–91, 1993.*
Cawthon et al. Genomics 9(3):446–60, 1991.*
Groudine et al. (X01275) GENESEQ Database, National Center for Biotechnology Information, National Library of Medicine, Bethesda, Maryland.*
Boehringer Mannheim Inc. (Catalog, 1994).*
Harper, et al., "The p21 Cdk–Interacting Protein Cip1 Is a Potent Inhibitor of G1 Cyclin–Dependent Kinases," *Cell*, 75:805–816 (1993).
Hartwell, et al., "Cell Cycle Control and Cancer," *Science*, 266:1821–1828 (1994).
Hiles, et al., "Phosphatidylinositol 3–Kinase: Structure and Expression of the 110 kd Catalytic Subunit," *Cell*, 70:419–429 (1992).
Jimenez, et al., "The rad3⁺gene of *Schizosaccharomyces pombe* is involved in multiple checkpoint functions and in DNA repair," *Proc.Nat'l.Acad.Sci.* (*USA*) 89:4952–4956 (1992).
Kato, et al., "An essential gene, ESR1, is required for mitotic cell growth, DNA repair and meiotic recombination in *Saccharomyces cerevisiae*," *Nucl.Acids.Res.*, 22:3104–3112 (1994).
Lamb, et al., "Inhibition of DNA replication by ionizing radiation is mediated by a trans–acting factor," *Int.J.Radiat.Biol.*, 56:125–130 (1989).
Leach, et al., "Regional Localization of 188 Sequence Tagged Sites on a Somatic Cell Hybrid Mapping Panel for Human Chromosome 3," *Genomics*, 24:549–556 (1994).
Maundrell, K., "nmt1 of Fission Yeast," *J.Biol.Chem.*, 265:10857–10864 (1990).

(List continued on next page.)

*Primary Examiner*—Anthony C. Caputa
*Assistant Examiner*—Gary B. Nickol
(74) *Attorney, Agent, or Firm*—Marshall, Gerstein & Borun

(57) ABSTRACT

This invention relates to a class of checkpoint genes and their polypeptide products which control progression through the cell cycle in eukaryotic cells. In particular this invention relates to *Schizosaccharomyces pombe* rad3 gene, to its human homologue (ATR) and to their encoded proteins. The invention further relates to assay methods for selecting compounds which modulate the activity of the polypeptide products of these checkpoint genes and the use of the selected compounds in anticancer therapy.

6 Claims, 1 Drawing Sheet

OTHER PUBLICATIONS

Morrow, et al., "TEL1, an S. cervisiae Homolog of the Human Gene Mutated in Ataxia Talangiectasia, Is Functionally Related to the Yeast Checkpoint Gene MEC1," *Cell*, 82:831–840 (1995).

Murray, et al., "Cloning and characterization of the *S.pombe rad15* gene, a homologue to the *S. cerevisiae RAD3* and human *ERCC2* genes," *Nucl.Acids Res.*, 20:2673–2678 (1992).

Nasim, et al., Genetic Control of Radiation Sensitivity in *Schizosaccharomyces Pombe, Genetics*, 79:573–582 (1975).

Painter, et al., "Radiosensitivity in ataxia–telangiectasia: A new explanation," *Proc.Nat'l.Acad.Sci. (USA)* 77:7315–7317 (1980).

Beamish, et al., "Radiosensitivity in ataxia–telangiectasia: anomalies in radiation–induced cell cycle delay," *Int.J.Radiant.Biol.*, 65:175–184 (1994).

Carr, et al., "The cellular responses to DNA damage," *Trends in Cell Biol.* 5:32–40 (1995).

Chein, et al., "The two–hybrid system: A Method to identify and clone genes for proteins that interact with a protein of interest," *Proc.Nat'l.Acad.Sci. (USA)* 88:9578–9582 (1991).

Deng, et al., "Mice Lacking p21$^{CIP1/WAF1}$ Undergo Normal Development, but Are Defective in G1 Checkpoint Control," *Cell*, 62:675–684 (1995).

Drwinga, et al., "NIGMS Human/Rodent Somatic Cell Hybrid Mapping panels 1 and 2," *Genomics* 16:311–314 (1993).

El–Deiry, et al., "WAF1, a Potential Mediator of p53 Tumor Suppression," *Cell*, 75:817–812 (1993).

Enoch, et al., "Fission yeast genes involved in coupling mitosis to completion of DNA replication," *Genes Dev.*, 6:2035–1046 (1992).

Geysen, et al., "A Priori Delineation of a Peptide which Mimics a Discontinuous Antigenic Determinant," *Mol.Immunol.*23:709–715 (1986).

Greenwell, et al., "TEL1, a Gene Involved in Controlling Telomere Length in *S. cerevisiae*, Is Homologous to the Human Ataxia Telangiectasia Gene," *Cell*, 82:823–829 (1995).

Grimm, et al., "Genetic engineering of *Schizosaccharomyces pombe*: A system for gene disruption and replacement using the ura4 gene as a selectable marker," *Mol. Gen. Genet.*, 215:81–86 (1988).

Gutz, et al., In Handbook of Genetics, King, R.C., Ed., Plenum Press, New York, vol. 1 pp. 395–446 (1974).

Hari, et al., "The mei–41 Gene of D. melanogaster Is a Structural and Functional Homolog of the Human Ataxia Telangiectasia Gene," *Cell*, 82:815–821 (1995).

Al–Khodairy, et al., "DNA repair mutants defining $G_2$ checkpoint pathways in *Schizosaccharomyces pombe*," *EMBO, J.*, 11:1343–1350 (1992).

Al–Khodairy, et al., "Identification and Characterization of New Elements Involved in Checkpoint and Feedback Controls in Fission Yeast," *Mol.Biol.Cell*, 5:147–160 (1994).

Allen, et al., "The SAD/RAD53 protein kinase control multiple checkpoints and DNA damage–induced transcription in yeast," *Genes Dev.*, 8:2401–2415 (1994).

Barbet, et al. "Versatile shuttle vectors and genomic libraries for use with *Schizosaccharomyces pombe*," *Gene*, 114:59–66 (1992).

Rowley, et al., "Checkpoint controls in *Schizosaccharomyces pombe:rad1*," *J.Embo.*, 11:1335–1342 (1992).

Savitsky, et al., "A single Ataxia Telangiectasia Gene with a Product Similar to P1–3 Kinase," *Science*, 268:1749–1753 (1995).

Seaton, et al., "Isolation and characterization of the *Schizosaccharomyces pombe rad3* gene, involved in the DNA damage and DNA synthesis checkpoints," *Gene*, 119:83–89 (1992).

Schu, et al., "Phosphatidylinositol 3–Kinase Encoded by Yeast VPS34 Gene Essential for Protein Sorting," *Science*, 260:88–91 (1993).

Sheldrick, et al., "Feedback Controls and G2 Checkpoints: Fission Yeast as a Model System," *BioEssays*, 15:755–782 (1993).

Walworth, et al., "Fission yeast chk1 protein kinase links that rad checkpoint pathway to cdc2," *Nature*, 363:368–371 (1993).

Weinert, et al., "Mitotic checkpoint genes in budding yeast and the dependence of mitosis on DNA replication and repair," *Genes Dev.* 8:652–665 (1994).

Weinert, et al., The RAD9 Gene Controls the Cell Cycle Response to DNA Damage in *Saccharomyces cerevisiae, Science*, 241:317–322 (1988).

Cimprich, "cDNA cloning and gene mapping of a candidate human cell cycle checkpoint gene," *Proc. Natl. Acad. Sci. U.S.A.*, vol. 93, pp. 2850–2855(1996).

\* cited by examiner

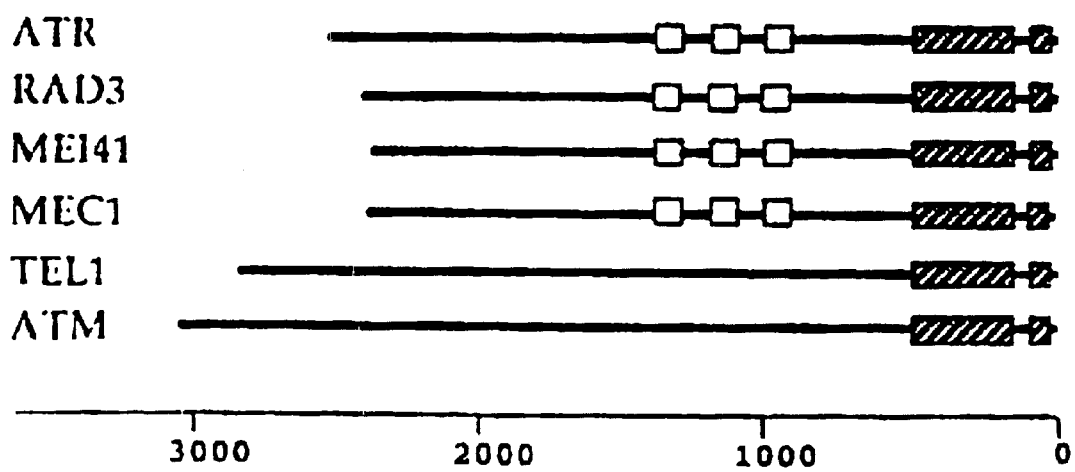
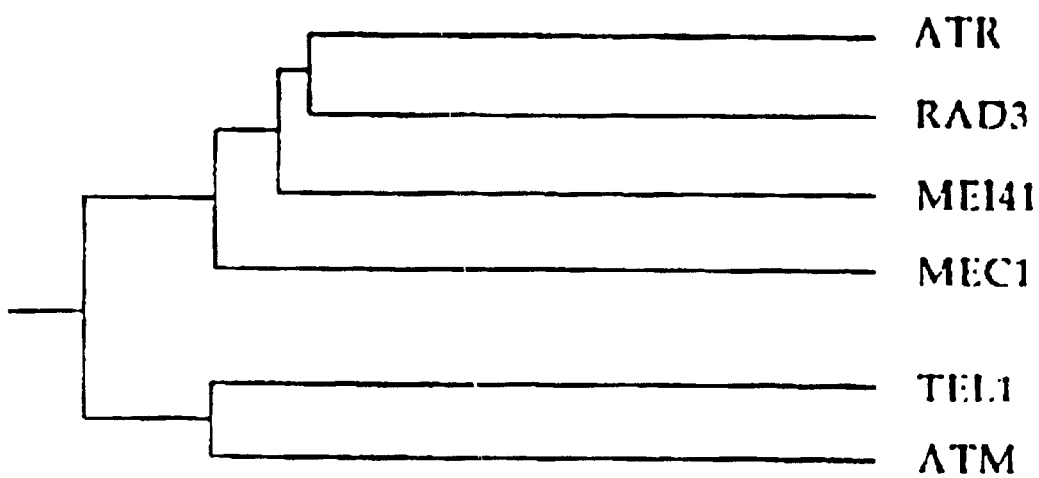

SEQUENCE LISTING

<160> NUMBER OF SEQ ID NOS: 14

<210> SEQ ID NO 1
<211> LENGTH: 8239
<212> TYPE: DNA
<213> ORGANISM: Homo sapiens
<220> FEATURE:
<221> NAME/KEY: CDS
<222> LOCATION: (80)..(8011)

<400> SEQUENCE: 1

```
gcgctcttcc ggcagcggta cgtttggaga cgccgggaac ccgcgttggc gtggttgact        60
agtgcctcgc agcctcagc atg ggg gaa cat ggc ctg gag ctg gct tcc atg        112
                    Met Gly Glu His Gly Leu Glu Leu Ala Ser Met
                      1               5                  10 atc ccc gcc ctg cgg gag ctg ggc agt gcc aca cca gag gaa tat aat        160
Ile Pro Ala Leu Arg Glu Leu Gly Ser Ala Thr Pro Glu Glu Tyr Asn
              15                  20                  25 aca gtt gta cag aag cca aga caa att ctg tgt caa ttc att gac cgg        208
Thr Val Val Gln Lys Pro Arg Gln Ile Leu Cys Gln Phe Ile Asp Arg
         30                  35                  40 ata ctt aca gat gta aat gtt gtt gct gta gaa ctt gta aag aaa act        256
Ile Leu Thr Asp Val Asn Val Val Ala Val Glu Leu Val Lys Lys Thr
     45                  50                  55 gac tct cag cca acc tcc gtg atg ttg ctt gat ttc atc cag cat atc        304
Asp Ser Gln Pro Thr Ser Val Met Leu Leu Asp Phe Ile Gln His Ile
 60                  65                  70                  75 atg aaa tcc tcc cca ctt atg ttt gta aat gtg agt gga agc cat gag        352
Met Lys Ser Ser Pro Leu Met Phe Val Asn Val Ser Gly Ser His Glu
                 80                  85                  90 cgc aaa ggc agt tgt att gaa ttc agt aat tgg atc ata acg aga ctt        400
Arg Lys Gly Ser Cys Ile Glu Phe Ser Asn Trp Ile Ile Thr Arg Leu
             95                 100                 105 ctg cgg att gca gca act ccc tcc tgt cat ttg tta cac aag aaa atc        448
Leu Arg Ile Ala Ala Thr Pro Ser Cys His Leu Leu His Lys Lys Ile
        110                 115                 120 tgt gaa gtc atc tgt tca tta tta ttt ctt ttt aaa agc aag agt cct        496
Cys Glu Val Ile Cys Ser Leu Leu Phe Leu Phe Lys Ser Lys Ser Pro
    125                 130                 135 gct att ttt ggg gta ctc aca aaa gaa tta tta caa ctt ttt gaa gac        544
Ala Ile Phe Gly Val Leu Thr Lys Glu Leu Leu Gln Leu Phe Glu Asp
140                 145                 150                 155 ttg gtt tac ctc cat aga aga aat gtg atg ggt cat gct gtg gaa tgg        592
Leu Val Tyr Leu His Arg Arg Asn Val Met Gly His Ala Val Glu Trp
                160                 165                 170 cca gtg gtc atg agc cga ttt tta agt caa tta gat gaa cac atg gga        640
Pro Val Val Met Ser Arg Phe Leu Ser Gln Leu Asp Glu His Met Gly
            175                 180                 185
```

```
                                                        -continued tat tta caa tca gct cct ttg cag ttg atg agt atg caa aat tta gaa     688
Tyr Leu Gln Ser Ala Pro Leu Gln Leu Met Ser Met Gln Asn Leu Glu
        190                 195                 200 ttt att gaa gtc act tta tta atg gtt ctt act cgt att att gca att     736
Phe Ile Glu Val Thr Leu Leu Met Val Leu Thr Arg Ile Ile Ala Ile
205                 210                 215 gtg ttt ttt aga agg caa gaa ctc tta ctt tgg cag ata ggt tgt gtt     784
Val Phe Phe Arg Arg Gln Glu Leu Leu Leu Trp Gln Ile Gly Cys Val
220                 225                 230                 235 ctg cta gag tat ggt agt cca aaa att aaa tcc cta gca att agc ttt     832
Leu Leu Glu Tyr Gly Ser Pro Lys Ile Lys Ser Leu Ala Ile Ser Phe
            240                 245                 250 tta aca gaa ctt ttt cag ctt gga gga cta cca gca caa cca gct agc     880
Leu Thr Glu Leu Phe Gln Leu Gly Gly Leu Pro Ala Gln Pro Ala Ser
        255                 260                 265 act ttt ttc agc tca ttt ttg gaa tta tta aaa cac ctt gta gaa atg     928
Thr Phe Phe Ser Ser Phe Leu Glu Leu Leu Lys His Leu Val Glu Met
    270                 275                 280 gat act gac caa ttg aaa ctc tat gaa gag cca tta tca aag ctg ata     976
Asp Thr Asp Gln Leu Lys Leu Tyr Glu Glu Pro Leu Ser Lys Leu Ile
285                 290                 295 aag aca cta ttt ccc ttt gaa gca gaa gct tat aga aat att gaa cct    1024
Lys Thr Leu Phe Pro Phe Glu Ala Glu Ala Tyr Arg Asn Ile Glu Pro
300                 305                 310                 315 gtc tat tta aat atg ctg ctg gaa aaa ctc tgt gtc atg ttt gaa gac    1072
Val Tyr Leu Asn Met Leu Leu Glu Lys Leu Cys Val Met Phe Glu Asp
            320                 325                 330 ggt gtg ctc atg cgg ctt aag tct gat ttg cta aaa gca gct ttg tgc    1120
Gly Val Leu Met Arg Leu Lys Ser Asp Leu Leu Lys Ala Ala Leu Cys
        335                 340                 345 cat tta ctg cag tat ttc ctt aaa ttt gtg cca gct ggg tat gaa tct    1168
His Leu Leu Gln Tyr Phe Leu Lys Phe Val Pro Ala Gly Tyr Glu Ser
    350                 355                 360 gct tta caa gtc agg aag gtc tat gtg aga aat att tgt aaa gct ctt    1216
Ala Leu Gln Val Arg Lys Val Tyr Val Arg Asn Ile Cys Lys Ala Leu
365                 370                 375 ttg gat gtg ctt gga att gag gta gat gca gag tac ttg ttg ggc cca    1264
Leu Asp Val Leu Gly Ile Glu Val Asp Ala Glu Tyr Leu Leu Gly Pro
380                 385                 390                 395 ctt tat gca gct ttg aaa atg gaa agt atg gaa atc att gag gag att    1312
Leu Tyr Ala Ala Leu Lys Met Glu Ser Met Glu Ile Ile Glu Glu Ile
            400                 405                 410 caa tgc caa act caa cag gaa aac ctc agc agt aat agt gat gga ata    1360
Gln Cys Gln Thr Gln Gln Glu Asn Leu Ser Ser Asn Ser Asp Gly Ile
        415                 420                 425 tca ccc aaa agg cgt cgt ctc agc tcg tct cta aac cct tct aaa aga    1408
Ser Pro Lys Arg Arg Arg Leu Ser Ser Ser Leu Asn Pro Ser Lys Arg
    430                 435                 440 gca cca aaa cag act gag gaa att aaa cat gtg gac atg aac caa aag    1456
Ala Pro Lys Gln Thr Glu Glu Ile Lys His Val Asp Met Asn Gln Lys
445                 450                 455 agc ata tta tgg agt gca ctg aaa cag aaa gct gaa tcc ctt cag att    1504
Ser Ile Leu Trp Ser Ala Leu Lys Gln Lys Ala Glu Ser Leu Gln Ile
460                 465                 470                 475 tcc ctt gaa tac agt ggc cta aag aat cct gtt att gag atg tta gaa    1552
Ser Leu Glu Tyr Ser Gly Leu Lys Asn Pro Val Ile Glu Met Leu Glu
            480                 485                 490 gga att gct gtt gtc tta caa ctg act gct ctg tgt act gtt cat tgt    1600
Gly Ile Ala Val Val Leu Gln Leu Thr Ala Leu Cys Thr Val His Cys
        495                 500                 505
```

```
tct cat caa aac atg aac tgc cgt act ttc aag gac tgt caa cat aaa    1648
Ser His Gln Asn Met Asn Cys Arg Thr Phe Lys Asp Cys Gln His Lys
        510                 515                 520 tcc aag aag aaa cct tct gta gtg ata act tgg atg tca ttg gat ttt    1696
Ser Lys Lys Lys Pro Ser Val Val Ile Thr Trp Met Ser Leu Asp Phe
525                 530                 535 tac aca aaa gtg ctt aag agc tgt aga agt ttg tta gaa tct gtt cag    1744
Tyr Thr Lys Val Leu Lys Ser Cys Arg Ser Leu Leu Glu Ser Val Gln
540                 545                 550                 555 aaa ctg gac ctg gag gca acc att gat aag gtg gtg aaa att tat gat    1792
Lys Leu Asp Leu Glu Ala Thr Ile Asp Lys Val Val Lys Ile Tyr Asp
                560                 565                 570 gct ttg att tat atg caa gta aac agt tca ttt gaa gat cat atc ctg    1840
Ala Leu Ile Tyr Met Gln Val Asn Ser Ser Phe Glu Asp His Ile Leu
            575                 580                 585 gaa gat tta tgt ggt atg ctc tca ctt cca tgg att tat tcc cat tct    1888
Glu Asp Leu Cys Gly Met Leu Ser Leu Pro Trp Ile Tyr Ser His Ser
        590                 595                 600 gat gat ggc tgt tta aag ttg acc aca ttt gcc gct aat ctc cta aca    1936
Asp Asp Gly Cys Leu Lys Leu Thr Thr Phe Ala Ala Asn Leu Leu Thr
    605                 610                 615 tta agc tgt agg att tca gat agc tat tca cca cag gca caa tca cga    1984
Leu Ser Cys Arg Ile Ser Asp Ser Tyr Ser Pro Gln Ala Gln Ser Arg
620                 625                 630                 635 tgt gtg ttt ctt ctg act ctg ttt cca aga aga ata ttc ctt gag tgg    2032
Cys Val Phe Leu Leu Thr Leu Phe Pro Arg Arg Ile Phe Leu Glu Trp
                640                 645                 650 aga aca gca gtt tac aac tgg gcc ctg cag agc tcc cat gaa gta atc    2080
Arg Thr Ala Val Tyr Asn Trp Ala Leu Gln Ser Ser His Glu Val Ile
            655                 660                 665 cgg gct agt tgt gtt agt gga ttt ttt atc tta ttg cag cag cag aat    2128
Arg Ala Ser Cys Val Ser Gly Phe Phe Ile Leu Leu Gln Gln Gln Asn
        670                 675                 680 tct tgt aac aga gtt ccc aag att ctt ata gat aaa gtc aaa gat gat    2176
Ser Cys Asn Arg Val Pro Lys Ile Leu Ile Asp Lys Val Lys Asp Asp
    685                 690                 695 tct gac att gtc aag aaa gaa ttt gct tct ata ctt ggt caa ctt gtc    2224
Ser Asp Ile Val Lys Lys Glu Phe Ala Ser Ile Leu Gly Gln Leu Val
700                 705                 710                 715 tgt act ctt cac ggc atg ttt tat ctg aca agt tct tta aca gaa cct    2272
Cys Thr Leu His Gly Met Phe Tyr Leu Thr Ser Ser Leu Thr Glu Pro
                720                 725                 730 ttc tct gaa cac gga cat gtg gac ctc ttc tgt agg aac ttg aaa gcc    2320
Phe Ser Glu His Gly His Val Asp Leu Phe Cys Arg Asn Leu Lys Ala
            735                 740                 745 act tct caa cat gaa tgt tca tct tct caa cta aaa gct tct gtc tgc    2368
Thr Ser Gln His Glu Cys Ser Ser Ser Gln Leu Lys Ala Ser Val Cys
        750                 755                 760 aag cca ttc ctt ttc cta ctg aaa aaa aaa ata cct agt cca gta aaa    2416
Lys Pro Phe Leu Phe Leu Leu Lys Lys Lys Ile Pro Ser Pro Val Lys
    765                 770                 775 ctt gct ttc ata gat aat cta cat cat ctt tgt aag cat ctt gat ttt    2464
Leu Ala Phe Ile Asp Asn Leu His His Leu Cys Lys His Leu Asp Phe
780                 785                 790                 795 aga gaa gat gaa aca gat gta aaa gca gtt ctt gga act tta tta aat    2512
Arg Glu Asp Glu Thr Asp Val Lys Ala Val Leu Gly Thr Leu Leu Asn
                800                 805                 810 tta atg gaa gat cca gac aaa gat gtt aga gtg gct ttt agt gga aat    2560
Leu Met Glu Asp Pro Asp Lys Asp Val Arg Val Ala Phe Ser Gly Asn
            815                 820                 825
```

```
atc aag cac ata ttg gaa tcc ttg gac tct gaa gat gga ttt ata aag    2608
Ile Lys His Ile Leu Glu Ser Leu Asp Ser Glu Asp Gly Phe Ile Lys
        830                 835                 840 gag ctt ttt gtc tta aga atg aag gaa gca tat aca cat gcc caa ata    2656
Glu Leu Phe Val Leu Arg Met Lys Glu Ala Tyr Thr His Ala Gln Ile
845                 850                 855 tca aga aat aat gag ctg aag gat acc ttg att ctt aca aca ggg gat    2704
Ser Arg Asn Asn Glu Leu Lys Asp Thr Leu Ile Leu Thr Thr Gly Asp
860                 865                 870                 875 att gga agg gcc gca aaa gga gat ttg gta cca ttt gca ctc tta cac    2752
Ile Gly Arg Ala Ala Lys Gly Asp Leu Val Pro Phe Ala Leu Leu His
                880                 885                 890 tta ttg cat tgt ttg tta tcc aag tca gca tct gtc tct gga gca gca    2800
Leu Leu His Cys Leu Leu Ser Lys Ser Ala Ser Val Ser Gly Ala Ala
            895                 900                 905 tac aca gaa att aga gct ctg gtt gca gct aaa agt gtt aaa ctg caa    2848
Tyr Thr Glu Ile Arg Ala Leu Val Ala Ala Lys Ser Val Lys Leu Gln
        910                 915                 920 agt ttt ttc agc cag tat aag aaa ccc atc tgt cag ttt ttg gta gaa    2896
Ser Phe Phe Ser Gln Tyr Lys Lys Pro Ile Cys Gln Phe Leu Val Glu
925                 930                 935 tcc ctt cac tct agt cag atg aca gca ctt ccg aat act cca tgc cag    2944
Ser Leu His Ser Ser Gln Met Thr Ala Leu Pro Asn Thr Pro Cys Gln
940                 945                 950                 955 aat gct gac gtg cga aaa caa gat gtg gct cac cag aga gaa atg gct    2992
Asn Ala Asp Val Arg Lys Gln Asp Val Ala His Gln Arg Glu Met Ala
                960                 965                 970 tta aat acg ttg tct gaa att gcc aac gtt ttc gac ttt cct gat ctt    3040
Leu Asn Thr Leu Ser Glu Ile Ala Asn Val Phe Asp Phe Pro Asp Leu
            975                 980                 985 aat cgt ttt ctt act agg aca tta caa gtt cta cta cct  gat ctt gct   3088
Asn Arg Phe Leu Thr Arg Thr Leu Gln Val Leu Leu Pro  Asp Leu Ala
        990                 995                 1000 gcc aaa  gca agc cct gca gct  tct gct ctc att cga  act tta gga aaa 3136
Ala Lys  Ala Ser Pro Ala Ala  Ser Ala Leu Ile Arg  Thr Leu Gly Lys
    1005             1010              1015 caa  tta aat gtc aat cgt  aga gag att tta ata  aac aac ttc aaa tat 3184
Gln  Leu Asn Val Asn Arg  Arg Glu Ile Leu Ile  Asn Asn Phe Lys Tyr
1020              1025              1030              1035 att ttt tct cat ttg  gtc tgt tct tgt tcc  aaa gat gaa tta gaa  cgt 3232
Ile Phe Ser His Leu  Val Cys Ser Cys Ser  Lys Asp Glu Leu Glu  Arg
             1040              1045              1050 gcc ctt cat tat  ctg aag aat gaa aca  gaa att gaa ctg ggg  agc ctg 3280
Ala Leu His Tyr  Leu Lys Asn Glu Thr  Glu Ile Glu Leu Gly  Ser Leu
             1055              1060              1065 ttg aga caa  gat ttc caa gga ttg  cat aat gaa tta ttg  ctg cgt att 3328
Leu Arg Gln  Asp Phe Gln Gly Leu  His Asn Glu Leu Leu  Leu Arg Ile
        1070              1075              1080 gga gaa  cac tat caa cag gtt  ttt aat ggt ttg tca  ata ctt gcc tca 3376
Gly Glu  His Tyr Gln Gln Val  Phe Asn Gly Leu Ser  Ile Leu Ala Ser
    1085              1090              1095 ttt  gca tcc agt gat gat  cca tat cag ggc ccg  aga gat atc ata tca 3424
Phe  Ala Ser Ser Asp Asp  Pro Tyr Gln Gly Pro  Arg Asp Ile Ile Ser
1100              1105              1110              1115 cct gaa ctg atg gct  gat tat tta caa ccc  aaa ttg ttg ggc att  ttg 3472
Pro Glu Leu Met Ala  Asp Tyr Leu Gln Pro  Lys Leu Leu Gly Ile  Leu
             1120              1125              1130 gct ttt ttt aac  atg cag tta ctg agc  tct agt gtt ggc att  gaa gat 3520
Ala Phe Phe Asn  Met Gln Leu Leu Ser  Ser Ser Val Gly Ile  Glu Asp
             1135              1140              1145
```

-continued

```
aag aaa atg gcc ttg aac agt ttg atg tct ttg atg aag tta atg gga    3568
Lys Lys Met Ala Leu Asn Ser Leu Met Ser Leu Met Lys Leu Met Gly
        1150                1155                1160 ccc aaa cat gtc agt tct gtg agg gtg aag atg atg acc aca ctg aga    3616
Pro Lys His Val Ser Ser Val Arg Val Lys Met Met Thr Thr Leu Arg
        1165                1170                1175 act ggc ctt cga ttc aag gat gat ttt cct gaa ttg tgt tgc aga gct    3664
Thr Gly Leu Arg Phe Lys Asp Asp Phe Pro Glu Leu Cys Cys Arg Ala
1180                1185                1190                1195 tgg gac tgc ttt gtt cgc tgc ctg gat cat gct tgt ctg ggc tcc ctt    3712
Trp Asp Cys Phe Val Arg Cys Leu Asp His Ala Cys Leu Gly Ser Leu
                1200                1205                1210 ctc agt cat gta ata gta gct ttg tta cct ctt ata cac atc cag cct    3760
Leu Ser His Val Ile Val Ala Leu Leu Pro Leu Ile His Ile Gln Pro
        1215                1220                1225 aaa gaa act gca gct atc ttc cac tac ctc ata att gaa aac agg gat    3808
Lys Glu Thr Ala Ala Ile Phe His Tyr Leu Ile Ile Glu Asn Arg Asp
        1230                1235                1240 gct gtg caa gat ttt ctt cat gaa ata tat ttt tta cct gat cat cca    3856
Ala Val Gln Asp Phe Leu His Glu Ile Tyr Phe Leu Pro Asp His Pro
        1245                1250                1255 gaa tta aaa aag ata aaa gcc gtt ctc cag gaa tac aga aag gag acc    3904
Glu Leu Lys Lys Ile Lys Ala Val Leu Gln Glu Tyr Arg Lys Glu Thr
1260                1265                1270                1275 tct gag agc act gat ctt cag aca act ctt cag ctc tct atg aag gcc    3952
Ser Glu Ser Thr Asp Leu Gln Thr Thr Leu Gln Leu Ser Met Lys Ala
                1280                1285                1290 att caa cat gaa aat gtc gat gtt cgt att cat gct ctt aca agc ttg    4000
Ile Gln His Glu Asn Val Asp Val Arg Ile His Ala Leu Thr Ser Leu
        1295                1300                1305 aag gaa acc ttg tat aaa aat cag gaa aaa ctg ata aag tat gca aca    4048
Lys Glu Thr Leu Tyr Lys Asn Gln Glu Lys Leu Ile Lys Tyr Ala Thr
        1310                1315                1320 gac agt gaa aca gta gaa cct att atc tca cag ttg gtg aca gtg ctt    4096
Asp Ser Glu Thr Val Glu Pro Ile Ile Ser Gln Leu Val Thr Val Leu
        1325                1330                1335 ttg aaa ggt tgc caa gat gca aac tct caa gct cgg ttg ctc tgt ggg    4144
Leu Lys Gly Cys Gln Asp Ala Asn Ser Gln Ala Arg Leu Leu Cys Gly
1340                1345                1350                1355 gaa tgt tta ggg gaa ttg ggg gcg ata gat cca ggt cga tta gat ttc    4192
Glu Cys Leu Gly Glu Leu Gly Ala Ile Asp Pro Gly Arg Leu Asp Phe
                1360                1365                1370 tca aca act gaa act caa gga aaa gat ttt aca ttt gtg act gga gta    4240
Ser Thr Thr Glu Thr Gln Gly Lys Asp Phe Thr Phe Val Thr Gly Val
        1375                1380                1385 gaa gat tca agc ttt gcc tat gga tta ttg atg gag cta aca aga gct    4288
Glu Asp Ser Ser Phe Ala Tyr Gly Leu Leu Met Glu Leu Thr Arg Ala
        1390                1395                1400 tac ctt gcg tat gct gat aat agc cga gct caa gat tca gct gcc tat    4336
Tyr Leu Ala Tyr Ala Asp Asn Ser Arg Ala Gln Asp Ser Ala Ala Tyr
        1405                1410                1415 gcc att cag gag ttg ctt tct att tat gac tgt aga gag atg gag acc    4384
Ala Ile Gln Glu Leu Leu Ser Ile Tyr Asp Cys Arg Glu Met Glu Thr
1420                1425                1430                1435 aac ggc cca ggt cac caa ttg tgg agg aga ttt cct gag cat gtt cgg    4432
Asn Gly Pro Gly His Gln Leu Trp Arg Arg Phe Pro Glu His Val Arg
                1440                1445                1450 gaa ata cta gaa cct cat cta aat acc aga tac aag agt tct cag aag    4480
Glu Ile Leu Glu Pro His Leu Asn Thr Arg Tyr Lys Ser Ser Gln Lys
        1455                1460                1465
```

```
tca acc gat tgg tct gga gta aag aag cca att tac tta agt aaa ttg    4528
Ser Thr Asp Trp Ser Gly Val Lys Lys Pro Ile Tyr Leu Ser Lys Leu
        1470                1475                1480 ggt agt aac ttt gca gaa tgg tca gca tct tgg gca ggt tat ctt att    4576
Gly Ser Asn Phe Ala Glu Trp Ser Ala Ser Trp Ala Gly Tyr Leu Ile
    1485                1490                1495 aca aag gtt cga cat gat ctt gcc agt aaa att ttc acc tgc tgt agc    4624
Thr Lys Val Arg His Asp Leu Ala Ser Lys Ile Phe Thr Cys Cys Ser
1500                1505                1510                1515 att atg atg aag cat gat ttc aaa gtg acc atc tat ctt ctt cca cat    4672
Ile Met Met Lys His Asp Phe Lys Val Thr Ile Tyr Leu Leu Pro His
            1520                1525                1530 att ctg gtg tat gtc tta ctg ggt tgt aat caa gaa gat cag cag gag    4720
Ile Leu Val Tyr Val Leu Leu Gly Cys Asn Gln Glu Asp Gln Gln Glu
        1535                1540                1545 gtt tat gca gaa att atg gca gtt cta aag cat gac gat cag cat acc    4768
Val Tyr Ala Glu Ile Met Ala Val Leu Lys His Asp Asp Gln His Thr
    1550                1555                1560 ata aat acc caa gac att gca tct gat ctg tgt caa ctc agt aca cag    4816
Ile Asn Thr Gln Asp Ile Ala Ser Asp Leu Cys Gln Leu Ser Thr Gln
1565                1570                1575 act gtg ttc tcc atg ctt gac cat ctc aca cag tgg gca agg cac aaa    4864
Thr Val Phe Ser Met Leu Asp His Leu Thr Gln Trp Ala Arg His Lys
1580                1585                1590                1595 ttt cag gca ctg aaa gct gag aaa tgt cca cac agc aaa tca aac aga    4912
Phe Gln Ala Leu Lys Ala Glu Lys Cys Pro His Ser Lys Ser Asn Arg
            1600                1605                1610 aat aag gta gac tca atg gta tct act gtg gat tat gaa gac tat cag    4960
Asn Lys Val Asp Ser Met Val Ser Thr Val Asp Tyr Glu Asp Tyr Gln
        1615                1620                1625 agt gta acc cgt ttt cta gac ctc ata ccc cag gat act ctg gca gta    5008
Ser Val Thr Arg Phe Leu Asp Leu Ile Pro Gln Asp Thr Leu Ala Val
    1630                1635                1640 gct tcc ttt cgc tcc aaa gca tac aca cga gct gta atg cac ttt gaa    5056
Ala Ser Phe Arg Ser Lys Ala Tyr Thr Arg Ala Val Met His Phe Glu
1645                1650                1655 tca ttt att aca gaa aag aag caa aat att cag gaa cat ctt gga ttt    5104
Ser Phe Ile Thr Glu Lys Lys Gln Asn Ile Gln Glu His Leu Gly Phe
1660                1665                1670                1675 tta cag aaa ttg tat gct gct atg cat gaa cct gat gga gtg gcc gga    5152
Leu Gln Lys Leu Tyr Ala Ala Met His Glu Pro Asp Gly Val Ala Gly
            1680                1685                1690 gtc agt gca att aga aag gca gaa cca tct cta aaa gaa cag atc ctt    5200
Val Ser Ala Ile Arg Lys Ala Glu Pro Ser Leu Lys Glu Gln Ile Leu
        1695                1700                1705 gaa cat gaa agc ctt ggc ttg ctg agg gat gcc act gct tgt tat gac    5248
Glu His Glu Ser Leu Gly Leu Leu Arg Asp Ala Thr Ala Cys Tyr Asp
    1710                1715                1720 agg gct att cag cta gaa cca gac cag atc att cat tat cat ggt gta    5296
Arg Ala Ile Gln Leu Glu Pro Asp Gln Ile Ile His Tyr His Gly Val
1725                1730                1735 gta aag tcc atg tta ggt ctt ggt cag ctg tct act gtt atc act cag    5344
Val Lys Ser Met Leu Gly Leu Gly Gln Leu Ser Thr Val Ile Thr Gln
1740                1745                1750                1755 gtg aat gga gtg cat gct aac agg tcc gag tgg aca gat gaa tta aac    5392
Val Asn Gly Val His Ala Asn Arg Ser Glu Trp Thr Asp Glu Leu Asn
            1760                1765                1770 acg tac aga gtg gaa gca gct tgg aaa ttg tca cag tgg gat ttg gtg    5440
Thr Tyr Arg Val Glu Ala Ala Trp Lys Leu Ser Gln Trp Asp Leu Val
        1775                1780                1785
```

-continued

```
gaa aac tat  ttg gca gca gat gga  aaa tct aca aca tgg  agt gtc aga  5488
Glu Asn Tyr  Leu Ala Ala Asp Gly  Lys Ser Thr Thr Trp  Ser Val Arg
         1790                1795                 1800 ctg gga cag cta tta tta tca  gcc aaa aaa aga gat  atc aca gct ttt  5536
Leu Gly Gln Leu Leu Leu Ser  Ala Lys Lys Arg Asp  Ile Thr Ala Phe
        1805                1810                  1815 tat  gac tca ctg aaa cta  gtg aga gca gaa  caa att gta cct ctt tca  5584
Tyr  Asp Ser Leu Lys Leu  Val Arg Ala Glu  Gln Ile Val Pro Leu Ser
1820                1825                 1830                 1835 gct gca agc ttt gaa  aga ggc tcc tac caa  cga gga tat gaa tat  att  5632
Ala Ala Ser Phe Glu  Arg Gly Ser Tyr Gln  Arg Gly Tyr Glu Tyr  Ile
             1840                 1845                 1850 gtg aga ttg cac  atg tta tgt gag ttg  gag cat agc atc aaa  cca ctt  5680
Val Arg Leu His  Met Leu Cys Glu Leu  Glu His Ser Ile Lys  Pro Leu
            1855                 1860                1865 ttc cag cat tct cca ggt gac agt  tct caa gaa gat tct  cta aac tgg  5728
Phe Gln His Ser Pro Gly Asp Ser  Ser Gln Glu Asp Ser  Leu Asn Trp
        1870                1875                 1880 gta gct cga cta gaa atg acc  cag aat tcc tac aga  gcc aag gac cct  5776
Val Ala Arg Leu Glu Met Thr  Gln Asn Ser Tyr Arg  Ala Lys Asp Pro
        1885                1890                 1895 atc ctg gct ctc cgg agg  gct tta cta agc ctc  aac aaa aga cca gat  5824
Ile Leu Ala Leu Arg Arg  Ala Leu Leu Ser Leu  Asn Lys Arg Pro Asp
1900                1905                 1910                 1915 tac aat gaa atg gtt  gga gaa tgc tgg ctg  cag agt gcc agg gta  gct  5872
Tyr Asn Glu Met Val  Gly Glu Cys Trp Leu  Gln Ser Ala Arg Val  Ala
             1920                 1925                 1930 aga aag gct ggt  cac cac cag aca gcc  tac aat gct ctc ctt  aat gca  5920
Arg Lys Ala Gly  His His Gln Thr Ala  Tyr Asn Ala Leu Leu  Asn Ala
            1935                 1940                1945 ggg gaa tca cga ctc gct gaa ctg  tac gtg gaa agg gca  aag tgg ctc  5968
Gly Glu Ser Arg Leu Ala Glu Leu  Tyr Val Glu Arg Ala  Lys Trp Leu
        1950                1955                 1960 tgg tcc aag ggt gat gtt cac  cag gca cta att gtt  ctt caa aaa ggt  6016
Trp Ser Lys Gly Asp Val His  Gln Ala Leu Ile Val  Leu Gln Lys Gly
        1965                1970                 1975 gtt  gaa tta tgt ttt cct  gaa aat gaa acc  cca cct gag ggt aag aac  6064
Val  Glu Leu Cys Phe Pro  Glu Asn Glu Thr  Pro Pro Glu Gly Lys Asn
1980                1985                 1990                 1995 atg tta atc cat ggt  cga gct atg cta cta  gtg ggc cga ttt atg  gaa  6112
Met Leu Ile His Gly  Arg Ala Met Leu Leu  Val Gly Arg Phe Met  Glu
             2000                2005                 2010 gaa aca gct aac  ttt gaa agc aat gca  att atg aaa aaa tat  aag gat  6160
Glu Thr Ala Asn  Phe Glu Ser Asn Ala  Ile Met Lys Lys Tyr  Lys Asp
            2015                 2020                2025 gtg acc gcg tgc ctg cca gaa tgg  gag gat ggg cat ttt  tac ctt gcc  6208
Val Thr Ala Cys Leu Pro Glu Trp  Glu Asp Gly His Phe  Tyr Leu Ala
        2030                2035                 2040 aag tac tat gac aaa ttg atg  ccc atg gtc aca gac  aac aaa atg gaa  6256
Lys Tyr Tyr Asp Lys Leu Met  Pro Met Val Thr Asp  Asn Lys Met Glu
        2045                2050                 2055 aag caa ggt gat ctc atc  cgg tat ata gtt  ctt cat ttt ggc aga tct  6304
Lys Gln Gly Asp Leu Ile  Arg Tyr Ile Val  Leu His Phe Gly Arg Ser
2060                2065                 2070                 2075 cta caa tat gga aat  cag ttc ata tat cag  tca atg cca cga atg  tta  6352
Leu Gln Tyr Gly Asn  Gln Phe Ile Tyr Gln  Ser Met Pro Arg Met  Leu
             2080                2085                 2090 act cta tgg ctt  gat tat ggt aca aag  gca tat gaa tgg gaa  aaa gct  6400
Thr Leu Trp Leu  Asp Tyr Gly Thr Lys  Ala Tyr Glu Trp Glu  Lys Ala
            2095                 2100                2105
```

```
ggc cgc tcc gat cgt gta caa atg agg aat gat ttg ggt aaa ata aac    6448
Gly Arg Ser Asp Arg Val Gln Met Arg Asn Asp Leu Gly Lys Ile Asn
        2110                2115                2120 aag gtt atc aca gag cat aca aac tat tta gct cca tat caa ttt ttg    6496
Lys Val Ile Thr Glu His Thr Asn Tyr Leu Ala Pro Tyr Gln Phe Leu
    2125                2130                2135 act gct ttt tca caa ttg atc tct cga att tgt cat tct cac gat gaa    6544
Thr Ala Phe Ser Gln Leu Ile Ser Arg Ile Cys His Ser His Asp Glu
2140                2145                2150                2155 gtt ttt gtt gtc ttg atg gaa ata ata gcc aaa gta ttt cta gcc tat    6592
Val Phe Val Val Leu Met Glu Ile Ile Ala Lys Val Phe Leu Ala Tyr
        2160                2165                2170 cct caa caa gca atg tgg atg atg aca gct gtg tca aag tca tct tat    6640
Pro Gln Gln Ala Met Trp Met Met Thr Ala Val Ser Lys Ser Ser Tyr
    2175                2180                2185 ccc atg cgt gtg aac aga tgc aag gaa atc ctc aat aaa gct att cat    6688
Pro Met Arg Val Asn Arg Cys Lys Glu Ile Leu Asn Lys Ala Ile His
        2190                2195                2200 atg aaa aaa tcc tta gag aag ttt gtt gga gat gca act cgc cta aca    6736
Met Lys Lys Ser Leu Glu Lys Phe Val Gly Asp Ala Thr Arg Leu Thr
    2205                2210                2215 gat aag ctt cta gaa ttg tgc aat aaa ccg gtt gat gga agt agt tcc    6784
Asp Lys Leu Leu Glu Leu Cys Asn Lys Pro Val Asp Gly Ser Ser Ser
2220                2225                2230                2235 aca tta agc atg agc act cat ttt aaa atg ctt aaa aag ctg gta gaa    6832
Thr Leu Ser Met Ser Thr His Phe Lys Met Leu Lys Lys Leu Val Glu
        2240                2245                2250 gaa gca aca ttt agt gaa atc ctc att cct cta caa tca gtc atg ata    6880
Glu Ala Thr Phe Ser Glu Ile Leu Ile Pro Leu Gln Ser Val Met Ile
    2255                2260                2265 cct aca ctt cca tca att ctg ggt acc cat gct aac cat gct agc cat    6928
Pro Thr Leu Pro Ser Ile Leu Gly Thr His Ala Asn His Ala Ser His
        2270                2275                2280 gaa cca ttt cct gga cat tgg gcc tat att gca ggg ttt gat gat atg    6976
Glu Pro Phe Pro Gly His Trp Ala Tyr Ile Ala Gly Phe Asp Asp Met
    2285                2290                2295 gtg gaa att ctt gct tct ctt cag aaa cca aag aag att tct tta aaa    7024
Val Glu Ile Leu Ala Ser Leu Gln Lys Pro Lys Lys Ile Ser Leu Lys
2300                2305                2310                2315 ggc tca gat gga aag ttc tac atc atg atg tgt aag cca aaa gat gac    7072
Gly Ser Asp Gly Lys Phe Tyr Ile Met Met Cys Lys Pro Lys Asp Asp
        2320                2325                2330 ctg aga aag gat tgt aga cta atg gaa ttc aat tcc ttg att aat aag    7120
Leu Arg Lys Asp Cys Arg Leu Met Glu Phe Asn Ser Leu Ile Asn Lys
    2335                2340                2345 tgc tta aga aaa gat gca gag tct cgt aga aga gaa ctt cat att cga    7168
Cys Leu Arg Lys Asp Ala Glu Ser Arg Arg Arg Glu Leu His Ile Arg
    2350                2355                2360 aca tat gca gtt att cca cta aat gat gaa tgt ggg att att gaa tgg    7216
Thr Tyr Ala Val Ile Pro Leu Asn Asp Glu Cys Gly Ile Ile Glu Trp
    2365                2370                2375 gtg aac aac act gct ggt ttg aga cct att ctg acc aaa cta tat aaa    7264
Val Asn Asn Thr Ala Gly Leu Arg Pro Ile Leu Thr Lys Leu Tyr Lys
2380                2385                2390                2395 gaa aag gga gtg tat atg aca gga aaa gaa ctt cgc cag tgt atg cta    7312
Glu Lys Gly Val Tyr Met Thr Gly Lys Glu Leu Arg Gln Cys Met Leu
        2400                2405                2410 cca aag tca gca gct tta tct gaa aaa ctc aaa gta ttc cga gaa ttt    7360
Pro Lys Ser Ala Ala Leu Ser Glu Lys Leu Lys Val Phe Arg Glu Phe
    2415                2420                2425
```

-continued

```
ctc ctg ccc agg cat cct cct att ttt cat gag tgg ttt ctg aga aca    7408
Leu Leu Pro Arg His Pro Pro Ile Phe His Glu Trp Phe Leu Arg Thr
        2430            2435                2440 ttc cct gat cct aca tca tgg tac agt agt aga tca gct tac tgc cgt    7456
Phe Pro Asp Pro Thr Ser Trp Tyr Ser Ser Arg Ser Ala Tyr Cys Arg
    2445            2450                2455 tcc act gca gta atg tca atg gtt ggt tat att ctg ggg ctt gga gac    7504
Ser Thr Ala Val Met Ser Met Val Gly Tyr Ile Leu Gly Leu Gly Asp
2460            2465                2470            2475 cgt cat ggt gaa aat att ctc ttt gat tct ttg act ggt gaa tgc gta    7552
Arg His Gly Glu Asn Ile Leu Phe Asp Ser Leu Thr Gly Glu Cys Val
            2480            2485                2490 cat gta gat ttc aat tgt ctt ttc aat aag gga gaa acc ttt gaa gtt    7600
His Val Asp Phe Asn Cys Leu Phe Asn Lys Gly Glu Thr Phe Glu Val
        2495            2500                2505 cca gaa att gtg cca ttt cgc ctg act cat aat atg gtt aat gga atg    7648
Pro Glu Ile Val Pro Phe Arg Leu Thr His Asn Met Val Asn Gly Met
    2510            2515                2520 ggt cct atg gga aca gag ggt ctt ttt cga aga gca tgt gaa gtt aca    7696
Gly Pro Met Gly Thr Glu Gly Leu Phe Arg Arg Ala Cys Glu Val Thr
2525            2530                2535 atg agg ctg atg cgt gat cag cga gag cct tta atg agt gtc tta aag    7744
Met Arg Leu Met Arg Asp Gln Arg Glu Pro Leu Met Ser Val Leu Lys
2540            2545                2550            2555 act ttt cta cat gat cct ctt gtg gaa tgg agt aaa cca gtg aaa ggg    7792
Thr Phe Leu His Asp Pro Leu Val Glu Trp Ser Lys Pro Val Lys Gly
        2560            2565                2570 cat tcc aaa gcg cca ctg aat gaa act gga gaa gtt gtc aat gaa aag    7840
His Ser Lys Ala Pro Leu Asn Glu Thr Gly Glu Val Val Asn Glu Lys
    2575            2580                2585 gcc aag acc cat gtt ctt gac att gag cag cga cta caa ggt gta atc    7888
Ala Lys Thr His Val Leu Asp Ile Glu Gln Arg Leu Gln Gly Val Ile
        2590            2595                2600 aag act cga aat aga gtg aca gga ctg ccg tta tct att gaa gga cat    7936
Lys Thr Arg Asn Arg Val Thr Gly Leu Pro Leu Ser Ile Glu Gly His
    2605            2610                2615 gtg cat tac ctt ata caa gaa gct act gat gaa aac tta cta tgc cag    7984
Val His Tyr Leu Ile Gln Glu Ala Thr Asp Glu Asn Leu Leu Cys Gln
2620            2625                2630            2635 atg tat ctt ggt tgg act cca tat atg tgaaatgaaa ttatgtaaaa          8031
Met Tyr Leu Gly Trp Thr Pro Tyr Met
                2640 gaatatgtta ataatctaaa agtaatgcat ttggtatgaa tctgtggttg tatctgttca  8091 attctaaagt acaacataaa tttacgttct cagcaactgt tatttctctc tgatcattaa  8151 ttatatgtaa aataatatac attcagttat taagaaataa actgctttct taataaaaaa  8211 aaaaaaaaaa aaaaaaaaa aaaaaaaa                                      8239

<210> SEQ ID NO 2
<211> LENGTH: 2644
<212> TYPE: PRT
<213> ORGANISM: Homo sapiens

<400> SEQUENCE: 2

Met Gly Glu His Gly Leu Glu Leu Ala Ser Met Ile Pro Ala Leu Arg
1               5                   10                  15

Glu Leu Gly Ser Ala Thr Pro Glu Glu Tyr Asn Thr Val Val Gln Lys
            20                  25                  30
```

-continued

```
Pro Arg Gln Ile Leu Cys Gln Phe Ile Asp Arg Ile Leu Thr Asp Val
         35                  40                  45
Asn Val Val Ala Val Glu Leu Val Lys Lys Thr Asp Ser Gln Pro Thr
 50                  55                  60
Ser Val Met Leu Leu Asp Phe Ile Gln His Ile Met Lys Ser Ser Pro
 65                  70                  75                  80
Leu Met Phe Val Asn Val Ser Gly Ser His Glu Arg Lys Gly Ser Cys
                 85                  90                  95
Ile Glu Phe Ser Asn Trp Ile Ile Thr Arg Leu Leu Arg Ile Ala Ala
             100                 105                 110
Thr Pro Ser Cys His Leu Leu His Lys Lys Ile Cys Glu Val Ile Cys
             115                 120                 125
Ser Leu Leu Phe Leu Phe Lys Ser Lys Ser Pro Ala Ile Phe Gly Val
130                 135                 140
Leu Thr Lys Glu Leu Leu Gln Leu Phe Glu Asp Leu Val Tyr Leu His
145                 150                 155                 160
Arg Arg Asn Val Met Gly His Ala Val Glu Trp Pro Val Val Met Ser
                 165                 170                 175
Arg Phe Leu Ser Gln Leu Asp Glu His Met Gly Tyr Leu Gln Ser Ala
             180                 185                 190
Pro Leu Gln Leu Met Ser Met Gln Asn Leu Glu Phe Ile Glu Val Thr
             195                 200                 205
Leu Leu Met Val Leu Thr Arg Ile Ile Ala Ile Val Phe Phe Arg Arg
210                 215                 220
Gln Glu Leu Leu Leu Trp Gln Ile Gly Cys Val Leu Leu Glu Tyr Gly
225                 230                 235                 240
Ser Pro Lys Ile Lys Ser Leu Ala Ile Ser Phe Leu Thr Glu Leu Phe
                 245                 250                 255
Gln Leu Gly Gly Leu Pro Ala Gln Pro Ala Ser Thr Phe Phe Ser Ser
             260                 265                 270
Phe Leu Glu Leu Leu Lys His Leu Val Glu Met Asp Thr Asp Gln Leu
             275                 280                 285
Lys Leu Tyr Glu Glu Pro Leu Ser Lys Leu Ile Lys Thr Leu Phe Pro
             290                 295                 300
Phe Glu Ala Glu Ala Tyr Arg Asn Ile Glu Pro Val Tyr Leu Asn Met
305                 310                 315                 320
Leu Leu Glu Lys Leu Cys Val Met Phe Glu Asp Gly Val Leu Met Arg
                 325                 330                 335
Leu Lys Ser Asp Leu Leu Lys Ala Ala Leu Cys His Leu Leu Gln Tyr
             340                 345                 350
Phe Leu Lys Phe Val Pro Ala Gly Tyr Glu Ser Ala Leu Gln Val Arg
             355                 360                 365
Lys Val Tyr Val Arg Asn Ile Cys Lys Ala Leu Leu Asp Val Leu Gly
             370                 375                 380
Ile Glu Val Asp Ala Glu Tyr Leu Leu Gly Pro Leu Tyr Ala Ala Leu
385                 390                 395                 400
Lys Met Glu Ser Met Glu Ile Ile Glu Glu Ile Gln Cys Gln Thr Gln
                 405                 410                 415
Gln Glu Asn Leu Ser Ser Asn Ser Asp Gly Ile Ser Pro Lys Arg Arg
             420                 425                 430
Arg Leu Ser Ser Ser Leu Asn Pro Ser Lys Arg Ala Pro Lys Gln Thr
             435                 440                 445
```

```
Glu Glu Ile Lys His Val Asp Met Asn Gln Lys Ser Ile Leu Trp Ser
        450                 455                 460
Ala Leu Lys Gln Lys Ala Glu Ser Leu Gln Ile Ser Leu Glu Tyr Ser
465                 470                 475                 480
Gly Leu Lys Asn Pro Val Ile Glu Met Leu Glu Gly Ile Ala Val Val
                485                 490                 495
Leu Gln Leu Thr Ala Leu Cys Thr Val His Cys Ser His Gln Asn Met
            500                 505                 510
Asn Cys Arg Thr Phe Lys Asp Cys Gln His Lys Ser Lys Lys Lys Pro
        515                 520                 525
Ser Val Val Ile Thr Trp Met Ser Leu Asp Phe Tyr Thr Lys Val Leu
    530                 535                 540
Lys Ser Cys Arg Ser Leu Leu Glu Ser Val Gln Lys Leu Asp Leu Glu
545                 550                 555                 560
Ala Thr Ile Asp Lys Val Val Lys Ile Tyr Asp Ala Leu Ile Tyr Met
                565                 570                 575
Gln Val Asn Ser Ser Phe Glu Asp His Ile Leu Glu Asp Leu Cys Gly
            580                 585                 590
Met Leu Ser Leu Pro Trp Ile Tyr Ser His Ser Asp Asp Gly Cys Leu
        595                 600                 605
Lys Leu Thr Thr Phe Ala Ala Asn Leu Leu Thr Leu Ser Cys Arg Ile
610                 615                 620
Ser Asp Ser Tyr Ser Pro Gln Ala Gln Ser Arg Cys Val Phe Leu Leu
625                 630                 635                 640
Thr Leu Phe Pro Arg Arg Ile Phe Leu Glu Trp Arg Thr Ala Val Tyr
                645                 650                 655
Asn Trp Ala Leu Gln Ser Ser His Glu Val Ile Arg Ala Ser Cys Val
            660                 665                 670
Ser Gly Phe Phe Ile Leu Leu Gln Gln Asn Ser Cys Asn Arg Val
        675                 680                 685
Pro Lys Ile Leu Ile Asp Lys Val Lys Asp Asp Ser Asp Ile Val Lys
        690                 695                 700
Lys Glu Phe Ala Ser Ile Leu Gly Gln Leu Val Cys Thr Leu His Gly
705                 710                 715                 720
Met Phe Tyr Leu Thr Ser Ser Leu Thr Glu Pro Phe Ser Glu His Gly
                725                 730                 735
His Val Asp Leu Phe Cys Arg Asn Leu Lys Ala Thr Ser Gln His Glu
            740                 745                 750
Cys Ser Ser Gln Leu Lys Ala Ser Val Cys Lys Pro Phe Leu Phe
        755                 760                 765
Leu Leu Lys Lys Lys Ile Pro Ser Pro Val Lys Leu Ala Phe Ile Asp
770                 775                 780
Asn Leu His His Leu Cys Lys His Leu Asp Phe Arg Glu Asp Glu Thr
785                 790                 795                 800
Asp Val Lys Ala Val Leu Gly Thr Leu Leu Asn Leu Met Glu Asp Pro
                805                 810                 815
Asp Lys Asp Val Arg Val Ala Phe Ser Gly Asn Ile Lys His Ile Leu
            820                 825                 830
Glu Ser Leu Asp Ser Glu Asp Gly Phe Ile Lys Glu Leu Phe Val Leu
        835                 840                 845
Arg Met Lys Glu Ala Tyr Thr His Ala Gln Ile Ser Arg Asn Asn Glu
850                 855                 860
```

-continued

```
Leu Lys Asp Thr Leu Ile Leu Thr Thr Gly Asp Ile Gly Arg Ala Ala
865                 870                 875                 880

Lys Gly Asp Leu Val Pro Phe Ala Leu Leu His Leu His Cys Leu
            885                 890                 895

Leu Ser Lys Ser Ala Ser Val Ser Gly Ala Ala Tyr Thr Glu Ile Arg
            900                 905                 910

Ala Leu Val Ala Ala Lys Ser Val Lys Leu Gln Ser Phe Phe Ser Gln
            915                 920                 925

Tyr Lys Lys Pro Ile Cys Gln Phe Leu Val Glu Ser Leu His Ser Ser
            930                 935                 940

Gln Met Thr Ala Leu Pro Asn Thr Pro Cys Gln Asn Ala Asp Val Arg
945                 950                 955                 960

Lys Gln Asp Val Ala His Gln Arg Glu Met Ala Leu Asn Thr Leu Ser
            965                 970                 975

Glu Ile Ala Asn Val Phe Asp Phe Pro Asp Leu Asn Arg Phe Leu Thr
            980                 985                 990

Arg Thr Leu Gln Val Leu Leu Pro Asp Leu Ala Ala Lys Ala Ser Pro
            995                 1000                1005

Ala Ala Ser Ala Leu Ile Arg Thr Leu Gly Lys Gln Leu Asn Val
            1010                1015                1020

Asn Arg Arg Glu Ile Leu Ile Asn Asn Phe Lys Tyr Ile Phe Ser
            1025                1030                1035

His Leu Val Cys Ser Cys Ser Lys Asp Glu Leu Glu Arg Ala Leu
            1040                1045                1050

His Tyr Leu Lys Asn Glu Thr Glu Ile Glu Leu Gly Ser Leu Leu
            1055                1060                1065

Arg Gln Asp Phe Gln Gly Leu His Asn Glu Leu Leu Leu Arg Ile
            1070                1075                1080

Gly Glu His Tyr Gln Gln Val Phe Asn Gly Leu Ser Ile Leu Ala
            1085                1090                1095

Ser Phe Ala Ser Ser Asp Asp Pro Tyr Gln Gly Pro Arg Asp Ile
            1100                1105                1110

Ile Ser Pro Glu Leu Met Ala Asp Tyr Leu Gln Pro Lys Leu Leu
            1115                1120                1125

Gly Ile Leu Ala Phe Phe Asn Met Gln Leu Leu Ser Ser Ser Val
            1130                1135                1140

Gly Ile Glu Asp Lys Lys Met Ala Leu Asn Ser Leu Met Ser Leu
            1145                1150                1155

Met Lys Leu Met Gly Pro Lys His Val Ser Ser Val Arg Val Lys
            1160                1165                1170

Met Met Thr Thr Leu Arg Thr Gly Leu Arg Phe Lys Asp Asp Phe
            1175                1180                1185

Pro Glu Leu Cys Cys Arg Ala Trp Asp Cys Phe Val Arg Cys Leu
            1190                1195                1200

Asp His Ala Cys Leu Gly Ser Leu Leu Ser His Val Ile Val Ala
            1205                1210                1215

Leu Leu Pro Leu Ile His Ile Gln Pro Lys Glu Thr Ala Ala Ile
            1220                1225                1230

Phe His Tyr Leu Ile Ile Glu Asn Arg Asp Ala Val Gln Asp Phe
            1235                1240                1245

Leu His Glu Ile Tyr Phe Leu Pro Asp His Pro Glu Leu Lys Lys
            1250                1255                1260
```

-continued

```
Ile Lys Ala Val Leu Gln Glu Tyr Arg Lys Glu Thr Ser Glu Ser
    1265                1270                1275

Thr Asp Leu Gln Thr Thr Leu Gln Leu Ser Met Lys Ala Ile Gln
    1280                1285                1290

His Glu Asn Val Asp Val Arg Ile His Ala Leu Thr Ser Leu Lys
    1295                1300                1305

Glu Thr Leu Tyr Lys Asn Gln Glu Lys Leu Ile Lys Tyr Ala Thr
    1310                1315                1320

Asp Ser Glu Thr Val Glu Pro Ile Ile Ser Gln Leu Val Thr Val
    1325                1330                1335

Leu Leu Lys Gly Cys Gln Asp Ala Asn Ser Gln Ala Arg Leu Leu
    1340                1345                1350

Cys Gly Glu Cys Leu Gly Glu Leu Gly Ala Ile Asp Pro Gly Arg
    1355                1360                1365

Leu Asp Phe Ser Thr Thr Glu Thr Gln Gly Lys Asp Phe Thr Phe
    1370                1375                1380

Val Thr Gly Val Glu Asp Ser Ser Phe Ala Tyr Gly Leu Leu Met
    1385                1390                1395

Glu Leu Thr Arg Ala Tyr Leu Ala Tyr Ala Asp Asn Ser Arg Ala
    1400                1405                1410

Gln Asp Ser Ala Ala Tyr Ala Ile Gln Glu Leu Leu Ser Ile Tyr
    1415                1420                1425

Asp Cys Arg Glu Met Glu Thr Asn Gly Pro Gly His Gln Leu Trp
    1430                1435                1440

Arg Arg Phe Pro Glu His Val Arg Glu Ile Leu Glu Pro His Leu
    1445                1450                1455

Asn Thr Arg Tyr Lys Ser Ser Gln Lys Ser Thr Asp Trp Ser Gly
    1460                1465                1470

Val Lys Lys Pro Ile Tyr Leu Ser Lys Leu Gly Ser Asn Phe Ala
    1475                1480                1485

Glu Trp Ser Ala Ser Trp Ala Gly Tyr Leu Ile Thr Lys Val Arg
    1490                1495                1500

His Asp Leu Ala Ser Lys Ile Phe Thr Cys Cys Ser Ile Met Met
    1505                1510                1515

Lys His Asp Phe Lys Val Thr Ile Tyr Leu Leu Pro His Ile Leu
    1520                1525                1530

Val Tyr Val Leu Leu Gly Cys Asn Gln Glu Asp Gln Gln Glu Val
    1535                1540                1545

Tyr Ala Glu Ile Met Ala Val Leu Lys His Asp Asp Gln His Thr
    1550                1555                1560

Ile Asn Thr Gln Asp Ile Ala Ser Asp Leu Cys Gln Leu Ser Thr
    1565                1570                1575

Gln Thr Val Phe Ser Met Leu Asp His Leu Thr Gln Trp Ala Arg
    1580                1585                1590

His Lys Phe Gln Ala Leu Lys Ala Glu Lys Cys Pro His Ser Lys
    1595                1600                1605

Ser Asn Arg Asn Lys Val Asp Ser Met Val Ser Thr Val Asp Tyr
    1610                1615                1620

Glu Asp Tyr Gln Ser Val Thr Arg Phe Leu Asp Leu Ile Pro Gln
    1625                1630                1635

Asp Thr Leu Ala Val Ala Ser Phe Arg Ser Lys Ala Tyr Thr Arg
    1640                1645                1650
```

-continued

```
Ala Val Met His Phe Glu Ser Phe Ile Thr Glu Lys Lys Gln Asn
1655                1660                1665

Ile Gln Glu His Leu Gly Phe Leu Gln Lys Leu Tyr Ala Ala Met
1670                1675                1680

His Glu Pro Asp Gly Val Ala Gly Val Ser Ala Ile Arg Lys Ala
1685                1690                1695

Glu Pro Ser Leu Lys Glu Gln Ile Leu Glu His Glu Ser Leu Gly
1700                1705                1710

Leu Leu Arg Asp Ala Thr Ala Cys Tyr Asp Arg Ala Ile Gln Leu
1715                1720                1725

Glu Pro Asp Gln Ile Ile His Tyr His Gly Val Val Lys Ser Met
1730                1735                1740

Leu Gly Leu Gly Gln Leu Ser Thr Val Ile Thr Gln Val Asn Gly
1745                1750                1755

Val His Ala Asn Arg Ser Glu Trp Thr Asp Glu Leu Asn Thr Tyr
1760                1765                1770

Arg Val Glu Ala Ala Trp Lys Leu Ser Gln Trp Asp Leu Val Glu
1775                1780                1785

Asn Tyr Leu Ala Ala Asp Gly Lys Ser Thr Thr Trp Ser Val Arg
1790                1795                1800

Leu Gly Gln Leu Leu Leu Ser Ala Lys Lys Arg Asp Ile Thr Ala
1805                1810                1815

Phe Tyr Asp Ser Leu Lys Leu Val Arg Ala Glu Gln Ile Val Pro
1820                1825                1830

Leu Ser Ala Ala Ser Phe Glu Arg Gly Ser Tyr Gln Arg Gly Tyr
1835                1840                1845

Glu Tyr Ile Val Arg Leu His Met Leu Cys Glu Leu Glu His Ser
1850                1855                1860

Ile Lys Pro Leu Phe Gln His Ser Pro Gly Asp Ser Ser Gln Glu
1865                1870                1875

Asp Ser Leu Asn Trp Val Ala Arg Leu Glu Met Thr Gln Asn Ser
1880                1885                1890

Tyr Arg Ala Lys Asp Pro Ile Leu Ala Leu Arg Arg Ala Leu Leu
1895                1900                1905

Ser Leu Asn Lys Arg Pro Asp Tyr Asn Glu Met Val Gly Glu Cys
1910                1915                1920

Trp Leu Gln Ser Ala Arg Val Ala Arg Lys Ala Gly His His Gln
1925                1930                1935

Thr Ala Tyr Asn Ala Leu Leu Asn Ala Gly Glu Ser Arg Leu Ala
1940                1945                1950

Glu Leu Tyr Val Glu Arg Ala Lys Trp Leu Trp Ser Lys Gly Asp
1955                1960                1965

Val His Gln Ala Leu Ile Val Leu Gln Lys Gly Val Glu Leu Cys
1970                1975                1980

Phe Pro Glu Asn Glu Thr Pro Pro Glu Gly Lys Asn Met Leu Ile
1985                1990                1995

His Gly Arg Ala Met Leu Leu Val Gly Arg Phe Met Glu Glu Thr
2000                2005                2010

Ala Asn Phe Glu Ser Asn Ala Ile Met Lys Lys Tyr Lys Asp Val
2015                2020                2025

Thr Ala Cys Leu Pro Glu Trp Glu Asp Gly His Phe Tyr Leu Ala
2030                2035                2040
```

-continued

```
Lys Tyr Tyr Asp Lys Leu Met Pro Met Val Thr Asp Asn Lys Met
    2045                2050                2055

Glu Lys Gln Gly Asp Leu Ile Arg Tyr Ile Val Leu His Phe Gly
    2060                2065                2070

Arg Ser Leu Gln Tyr Gly Asn Gln Phe Ile Tyr Gln Ser Met Pro
    2075                2080                2085

Arg Met Leu Thr Leu Trp Leu Asp Tyr Gly Thr Lys Ala Tyr Glu
    2090                2095                2100

Trp Glu Lys Ala Gly Arg Ser Asp Arg Val Gln Met Arg Asn Asp
    2105                2110                2115

Leu Gly Lys Ile Asn Lys Val Ile Thr Glu His Thr Asn Tyr Leu
    2120                2125                2130

Ala Pro Tyr Gln Phe Leu Thr Ala Phe Ser Gln Leu Ile Ser Arg
    2135                2140                2145

Ile Cys His Ser His Asp Glu Val Phe Val Val Leu Met Glu Ile
    2150                2155                2160

Ile Ala Lys Val Phe Leu Ala Tyr Pro Gln Gln Ala Met Trp Met
    2165                2170                2175

Met Thr Ala Val Ser Lys Ser Ser Tyr Pro Met Arg Val Asn Arg
    2180                2185                2190

Cys Lys Glu Ile Leu Asn Lys Ala Ile His Met Lys Lys Ser Leu
    2195                2200                2205

Glu Lys Phe Val Gly Asp Ala Thr Arg Leu Thr Asp Lys Leu Leu
    2210                2215                2220

Glu Leu Cys Asn Lys Pro Val Asp Gly Ser Ser Thr Leu Ser
    2225                2230                2235

Met Ser Thr His Phe Lys Met Leu Lys Lys Leu Val Glu Glu Ala
    2240                2245                2250

Thr Phe Ser Glu Ile Leu Ile Pro Leu Gln Ser Val Met Ile Pro
    2255                2260                2265

Thr Leu Pro Ser Ile Leu Gly Thr His Ala Asn His Ala Ser His
    2270                2275                2280

Glu Pro Phe Pro Gly His Trp Ala Tyr Ile Ala Gly Phe Asp Asp
    2285                2290                2295

Met Val Glu Ile Leu Ala Ser Leu Gln Lys Pro Lys Lys Ile Ser
    2300                2305                2310

Leu Lys Gly Ser Asp Gly Lys Phe Tyr Ile Met Met Cys Lys Pro
    2315                2320                2325

Lys Asp Asp Leu Arg Lys Asp Cys Arg Leu Met Glu Phe Asn Ser
    2330                2335                2340

Leu Ile Asn Lys Cys Leu Arg Lys Asp Ala Glu Ser Arg Arg Arg
    2345                2350                2355

Glu Leu His Ile Arg Thr Tyr Ala Val Ile Pro Leu Asn Asp Glu
    2360                2365                2370

Cys Gly Ile Ile Glu Trp Val Asn Asn Thr Ala Gly Leu Arg Pro
    2375                2380                2385

Ile Leu Thr Lys Leu Tyr Lys Glu Lys Gly Val Tyr Met Thr Gly
    2390                2395                2400

Lys Glu Leu Arg Gln Cys Met Leu Pro Lys Ser Ala Ala Leu Ser
    2405                2410                2415

Glu Lys Leu Lys Val Phe Arg Glu Phe Leu Leu Pro Arg His Pro
    2420                2425                2430
```

```
Pro Ile Phe His Glu Trp Phe Leu Arg Thr Phe Pro Asp Pro Thr
    2435                2440                2445

Ser Trp Tyr Ser Ser Arg Ser Ala Tyr Cys Arg Ser Thr Ala Val
    2450                2455                2460

Met Ser Met Val Gly Tyr Ile Leu Gly Leu Gly Asp Arg His Gly
    2465                2470                2475

Glu Asn Ile Leu Phe Asp Ser Leu Thr Gly Glu Cys Val His Val
    2480                2485                2490

Asp Phe Asn Cys Leu Phe Asn Lys Gly Glu Thr Phe Glu Val Pro
    2495                2500                2505

Glu Ile Val Pro Phe Arg Leu Thr His Asn Met Val Asn Gly Met
    2510                2515                2520

Gly Pro Met Gly Thr Glu Gly Leu Phe Arg Arg Ala Cys Glu Val
    2525                2530                2535

Thr Met Arg Leu Met Arg Asp Gln Arg Glu Pro Leu Met Ser Val
    2540                2545                2550

Leu Lys Thr Phe Leu His Asp Pro Leu Val Glu Trp Ser Lys Pro
    2555                2560                2565

Val Lys Gly His Ser Lys Ala Pro Leu Asn Glu Thr Gly Glu Val
    2570                2575                2580

Val Asn Glu Lys Ala Lys Thr His Val Leu Asp Ile Glu Gln Arg
    2585                2590                2595

Leu Gln Gly Val Ile Lys Thr Arg Asn Arg Val Thr Gly Leu Pro
    2600                2605                2610

Leu Ser Ile Glu Gly His Val His Tyr Leu Ile Gln Glu Ala Thr
    2615                2620                2625

Asp Glu Asn Leu Leu Cys Gln Met Tyr Leu Gly Trp Thr Pro Tyr
    2630                2635                2640

Met
```

<210> SEQ ID NO 3
<211> LENGTH: 8022
<212> TYPE: DNA
<213> ORGANISM: Homo sapiens
<220> FEATURE:
<221> NAME/KEY: CDS
<222> LOCATION: (585)..(7742)
<223> OTHER INFORMATION:

<400> SEQUENCE: 3

```
ggtaccaagt aaaaactgct tagtaagtat aaaacacaga agaatccgcg atctagtgaa    60
ccaatgccct gcgtatgacg ctccactgac gctatagtca atgagaacta ggatgtgcga   120
ttataactta tcttttcaat attttcttat tatttattta agaaataatt gaattaaaac   180
tcatttcttc ttttattagc cgtaaaatag cttattttct ctcctactac ctttcaacaa   240 taacttttttt ttttgtttat tgaccattat aatcacatca aaagtcaaaa aattcaatca   300
ttatcagaaa catccagcct aatattactt aaaagttagt ttcctctgaa aattcagtat   360
cacaaaagct cgttaattag catcgctcga tacttagtgc accatgcatc ttcctttacc   420
tcgtgagtgg aaatcgattt gataatcgat tgccactttt cgcataattc tattgagata   480
ttttattact tacaatcgtc ttttataaat gctcaagact ttgaacgcgc gtgttgcgtt   540
ttaaaaaggc ctttttttga attgaatcaa tggtttgata tagt atg agc caa cac   596
                                                 Met Ser Gln His
                                                  1
```

| | | |
|---|---|---|
| gca aaa agg aaa gct ggg tca ctc gat ctt tca ccc aga ggc tta gat<br>Ala Lys Arg Lys Ala Gly Ser Leu Asp Leu Ser Pro Arg Gly Leu Asp<br>5                              10                     15                 20 | 644 |
| gac aga cag gct ttc gga cag ctt ttg aaa gaa gta tta gca tta gac<br>Asp Arg Gln Ala Phe Gly Gln Leu Leu Lys Glu Val Leu Ala Leu Asp<br>                      25                         30                     35 | 692 |
| aaa gaa cat gag tta ggt aga agt aat tct tta cca tct atg acc tcc<br>Lys Glu His Glu Leu Gly Arg Ser Asn Ser Leu Pro Ser Met Thr Ser<br>              40                        45                     50 | 740 |
| gag ctt gtt gaa gtt tta att gaa gtt ggt ctt cta gct ttt aaa cat<br>Glu Leu Val Glu Val Leu Ile Glu Val Gly Leu Leu Ala Phe Lys His<br>            55                         60                     65 | 788 |
| gat gat tca aaa tct gaa ttt atc tct cct aag atg cta aaa gaa gcc<br>Asp Asp Ser Lys Ser Glu Phe Ile Ser Pro Lys Met Leu Lys Glu Ala<br>70                           75                     80 | 836 |
| cat ctc tct cta caa gcg tta atg cta atc tta aaa agg tct ccg aca<br>His Leu Ser Leu Gln Ala Leu Met Leu Ile Leu Lys Arg Ser Pro Thr<br>85                           90                     95              100 | 884 |
| gtt ttg cgg gag att aaa tca tct gtt act ctt ttg gat tgg att tta<br>Val Leu Arg Glu Ile Lys Ser Ser Val Thr Leu Leu Asp Trp Ile Leu<br>                      105                    110                 115 | 932 |
| ccc agg act ata tca ttg ttt gct gat att cgt ttt att aag tta ttt<br>Pro Arg Thr Ile Ser Leu Phe Ala Asp Ile Arg Phe Ile Lys Leu Phe<br>                   120                    125                  130 | 980 |
| gac tca tta aaa gag ttt cat aag cta att tat cag cta atc agt gaa<br>Asp Ser Leu Lys Glu Phe His Lys Leu Ile Tyr Gln Leu Ile Ser Glu<br>              135                    140                   145 | 1028 |
| aag tca ttc cta tgg gac tta tat gct tcg ttt atg cgt tat tgg aaa<br>Lys Ser Phe Leu Trp Asp Leu Tyr Ala Ser Phe Met Arg Tyr Trp Lys<br>150                         155                    160 | 1076 |
| tat tat att aca aac gtt tct tct ata gtt ctc caa atc act aat gct<br>Tyr Tyr Ile Thr Asn Val Ser Ser Ile Val Leu Gln Ile Thr Asn Ala<br>165                         170                    175                180 | 1124 |
| aca ttc cct tac aag atg ccc tca ccc aat tct caa cca ttg cag agt<br>Thr Phe Pro Tyr Lys Met Pro Ser Pro Asn Ser Gln Pro Leu Gln Ser<br>                   185                    190                  195 | 1172 |
| atc tcc cca aat tat cca acc cat cga gag gac aaa ttt gat tta ctt<br>Ile Ser Pro Asn Tyr Pro Thr His Arg Glu Asp Lys Phe Asp Leu Leu<br>              200                    205                   210 | 1220 |
| atc att aat ata gag gag gct tgt aca ttt ttc ttt gaa agt gcc cat<br>Ile Ile Asn Ile Glu Glu Ala Cys Thr Phe Phe Phe Glu Ser Ala His<br>                   215                    220                  225 | 1268 |
| ttt ttt gca caa tgc tca tat tta aag aaa tcc aat ttt cct agt cca<br>Phe Phe Ala Gln Cys Ser Tyr Leu Lys Lys Ser Asn Phe Pro Ser Pro<br>230                         235                    240 | 1316 |
| cct ctc ttt aca gcg tgg act tgg atc aag cca tgt ttt ttt aat ttt<br>Pro Leu Phe Thr Ala Trp Thr Trp Ile Lys Pro Cys Phe Phe Asn Phe<br>245                         250                    255                260 | 1364 |
| gtt att tta tta aaa cga atc agc atc gga gac tca cag ctc ttt cta<br>Val Ile Leu Leu Lys Arg Ile Ser Ile Gly Asp Ser Gln Leu Phe Leu<br>                   265                    270                 275 | 1412 |
| cat ttg cat tca cgt ata gtc caa act tta tgc tgt ttt tcc ttg aat<br>His Leu His Ser Arg Ile Val Gln Thr Leu Cys Cys Phe Ser Leu Asn<br>              280                    285                   290 | 1460 |
| ttt ata tat cat ggc ctt ccc att tgt gaa aaa tct aaa cat att tta<br>Phe Ile Tyr His Gly Leu Pro Ile Cys Glu Lys Ser Lys His Ile Leu<br>            295                    300                   305 | 1508 |
| atg tcc tcc atc aac tta aca ttg gga tca ttg aag aaa act tat aca<br>Met Ser Ser Ile Asn Leu Thr Leu Gly Ser Leu Lys Lys Thr Tyr Thr<br>310                         315                    320 | 1556 |

-continued

| | |
|---|---|
| gtt gct aat act gct ata tct ctt ttt ttt ctc tct tta ttt gtt tta<br>Val Ala Asn Thr Ala Ile Ser Leu Phe Phe Leu Ser Leu Phe Val Leu<br>325                       330                     335                     340 | 1604 |
| ccc aaa act gta gct ggt cta ttc tat cct ttt ggg gtt tcc tta ctt<br>Pro Lys Thr Val Ala Gly Leu Phe Tyr Pro Phe Gly Val Ser Leu Leu<br>                     345                     350                     355 | 1652 |
| tct gac ttc aag gta tta gag caa ctt gaa cca gat tct gat ctc aaa<br>Ser Asp Phe Lys Val Leu Glu Gln Leu Glu Pro Asp Ser Asp Leu Lys<br>                 360                     365                     370 | 1700 |
| aag gca ata ata tta ttt aag tgc aga tac caa agt tca gaa ata gat<br>Lys Ala Ile Ile Leu Phe Lys Cys Arg Tyr Gln Ser Ser Glu Ile Asp<br>            375                     380                     385 | 1748 |
| caa aca act ctc cgt gct ttt ggc gaa att tgt act ggt aaa ctt gaa<br>Gln Thr Thr Leu Arg Ala Phe Gly Glu Ile Cys Thr Gly Lys Leu Glu<br>390                     395                     400 | 1796 |
| aac acg ttg ttt tct aac tct gaa tta aac ctt ttt ctt tta cat tat<br>Asn Thr Leu Phe Ser Asn Ser Glu Leu Asn Leu Phe Leu Leu His Tyr<br>405                     410                     415                     420 | 1844 |
| ctt tcc ttg gac aat gac ttg tca aat att ctt aaa gtg gat ttc cag<br>Leu Ser Leu Asp Asn Asp Leu Ser Asn Ile Leu Lys Val Asp Phe Gln<br>                     425                     430                     435 | 1892 |
| aat ggt cat aac ata tgt aca ttt gca aaa tgg tgt ata aac aac aac<br>Asn Gly His Asn Ile Cys Thr Phe Ala Lys Trp Cys Ile Asn Asn Asn<br>            440                     445                     450 | 1940 |
| tta gat gaa ccg tct aat tta aag cac ttt cgt gaa atg tta gat tat<br>Leu Asp Glu Pro Ser Asn Leu Lys His Phe Arg Glu Met Leu Asp Tyr<br>                 455                     460                     465 | 1988 |
| tat agc tct cat aat gtt aca ata agt gag gac gac ctg aag aac ttc<br>Tyr Ser Ser His Asn Val Thr Ile Ser Glu Asp Asp Leu Lys Asn Phe<br>470                     475                     480 | 2036 |
| tct tta gtt ttg tgt act cat gtt gca aag gtg aat gag aaa aca aat<br>Ser Leu Val Leu Cys Thr His Val Ala Lys Val Asn Glu Lys Thr Asn<br>485                     490                     495                     500 | 2084 |
| agt att ttc cgc aca tat gaa gta cat ggt tgt gaa gtt tgt aac tca<br>Ser Ile Phe Arg Thr Tyr Glu Val His Gly Cys Glu Val Cys Asn Ser<br>                     505                     510                     515 | 2132 |
| ttt tgt tta cta ttt gat gag cgg tcg cct ttt aaa att cct tat cac<br>Phe Cys Leu Leu Phe Asp Glu Arg Ser Pro Phe Lys Ile Pro Tyr His<br>            520                     525                     530 | 2180 |
| gaa ttg ttt tgt gca ttg cta aaa aat ccc gac ata att tcc tct tct<br>Glu Leu Phe Cys Ala Leu Leu Lys Asn Pro Asp Ile Ile Ser Ser Ser<br>535                     540                     545 | 2228 |
| gtt aaa caa tca ttg ttg ctt gat ggc ttt ttt cgg tgg agc cag cat<br>Val Lys Gln Ser Leu Leu Leu Asp Gly Phe Phe Arg Trp Ser Gln His<br>550                     555                     560 | 2276 |
| tgc tca aac ttt aat aaa gaa tca atg tta agt tta aga gaa ttt att<br>Cys Ser Asn Phe Asn Lys Glu Ser Met Leu Ser Leu Arg Glu Phe Ile<br>565                     570                     575                     580 | 2324 |
| atg aaa gca tta gcc agt act tca aga tgt tta cgt gtt gtt gct gca<br>Met Lys Ala Leu Ala Ser Thr Ser Arg Cys Leu Arg Val Val Ala Ala<br>                     585                     590                     595 | 2372 |
| aaa gtt ttg ccc att ttc att aag gga cct aat aat ctt gat ata gtt<br>Lys Val Leu Pro Ile Phe Ile Lys Gly Pro Asn Asn Leu Asp Ile Val<br>            600                     605                     610 | 2420 |
| gaa ttt cac aag gaa agt aaa gcc ttg att ttt aat acg ttg aaa ata<br>Glu Phe His Lys Glu Ser Lys Ala Leu Ile Phe Asn Thr Leu Lys Ile<br>                 615                     620                     625 | 2468 |
| ttg gcg gtg gaa aat aca gct att tta gaa acg gtc att ctt tcc tgg<br>Leu Ala Val Glu Asn Thr Ala Ile Leu Glu Thr Val Ile Leu Ser Trp<br>630                     635                     640 | 2516 |

| | | |
|---|---|---|
| atc tcc tta tct aga gtg gta gaa gaa gaa gaa tta cat ttt gta cta<br>Ile Ser Leu Ser Arg Val Val Glu Glu Glu Glu Leu His Phe Val Leu<br>645                        650                       655                   660 | 2564 |
| ttg gaa gtt ata tct tct gtg ata aac agc gga ata ttt tat caa ggc<br>Leu Glu Val Ile Ser Ser Val Ile Asn Ser Gly Ile Phe Tyr Gln Gly<br>                      665                     670                    675 | 2612 |
| att ggt ctc agc gct ctg caa caa att gcc tcg acg cgt cat ata tcc<br>Ile Gly Leu Ser Ala Leu Gln Gln Ile Ala Ser Thr Arg His Ile Ser<br>         680                     685                     690 | 2660 |
| gtt tgg caa tta ctt tct cca tat tgg cca aca gtg tcc gtt gcg att<br>Val Trp Gln Leu Leu Ser Pro Tyr Trp Pro Thr Val Ser Val Ala Ile<br>         695                     700                     705 | 2708 |
| gtc caa ggt atg ggt aaa aaa ccg aac ata gcc agt tta ttt gct cag<br>Val Gln Gly Met Gly Lys Lys Pro Asn Ile Ala Ser Leu Phe Ala Gln<br>710                        715                       720 | 2756 |
| ctt atg aat att tcc gag ggc gat ttt ctt att cga aca cag gcg tac<br>Leu Met Asn Ile Ser Glu Gly Asp Phe Leu Ile Arg Thr Gln Ala Tyr<br>725                        730                     735                    740 | 2804 |
| act tta cca ttc ctt gta ctt act aaa aac aaa gcg tta ata gta cgt<br>Thr Leu Pro Phe Leu Val Leu Thr Lys Asn Lys Ala Leu Ile Val Arg<br>                     745                     750                    755 | 2852 |
| ata gct gaa ctt tca caa agt gat gtt gct act ttg tgc ctt acc aat<br>Ile Ala Glu Leu Ser Gln Ser Asp Val Ala Thr Leu Cys Leu Thr Asn<br>         760                     765                     770 | 2900 |
| atg cat aaa atc ctt gct tcg cta ctt act acg gat cat cct aat ttg<br>Met His Lys Ile Leu Ala Ser Leu Leu Thr Thr Asp His Pro Asn Leu<br>         775                     780                     785 | 2948 |
| gaa gag agt gtg atg ctt ctt ctt tca ctg gcc act tct gat ttt gaa<br>Glu Glu Ser Val Met Leu Leu Leu Ser Leu Ala Thr Ser Asp Phe Glu<br>790                        795                       800 | 2996 |
| aaa gtt gat tta acg tct ttg tta cgc tct gat cct att tct att act<br>Lys Val Asp Leu Thr Ser Leu Leu Arg Ser Asp Pro Ile Ser Ile Thr<br>805                        810                     815                  820 | 3044 |
| gtg gag ttg tta cag ctt tat cag aat gat gtt cct cat gaa aaa att<br>Val Glu Leu Leu Gln Leu Tyr Gln Asn Asp Val Pro His Glu Lys Ile<br>                     825                     830                    835 | 3092 |
| gaa aat gct tta aga aag gta gca atg att gtc tct caa gtg gtt aat<br>Glu Asn Ala Leu Arg Lys Val Ala Met Ile Val Ser Gln Val Val Asn<br>         840                     845                     850 | 3140 |
| gac gaa gac ttg agc aat aag gaa tta ctt tat gat ttt ttt aat aat<br>Asp Glu Asp Leu Ser Asn Lys Glu Leu Leu Tyr Asp Phe Phe Asn Asn<br>         855                     860                     865 | 3188 |
| cac att ttg ggt atc tta gca gaa ttt tct aat atc ctt aac gac ctg<br>His Ile Leu Gly Ile Leu Ala Glu Phe Ser Asn Ile Leu Asn Asp Leu<br>870                        875                     880 | 3236 |
| aaa gga aag act tca att aat gaa aag att aag aca att gtc ggc att<br>Lys Gly Lys Thr Ser Ile Asn Glu Lys Ile Lys Thr Ile Val Gly Ile<br>885                        890                     895                  900 | 3284 |
| gaa aaa atg tta tct tta tgt gga ggt gca gtc aaa ctt gga tta cca<br>Glu Lys Met Leu Ser Leu Cys Gly Gly Ala Val Lys Leu Gly Leu Pro<br>                     905                     910                    915 | 3332 |
| cag ata ctt tct aat tta caa agt gct ttt caa aat gag cac tta agg<br>Gln Ile Leu Ser Asn Leu Gln Ser Ala Phe Gln Asn Glu His Leu Arg<br>         920                     925                     930 | 3380 |
| ttt tat gca atc aaa gct tgg ttc agt ttg ata tta gca acc aag gag<br>Phe Tyr Ala Ile Lys Ala Trp Phe Ser Leu Ile Leu Ala Thr Lys Glu<br>         935                     940                     945 | 3428 |
| ccc gag tat agt tca att gct ggt tta agt ctt gta att tta cct cct<br>Pro Glu Tyr Ser Ser Ile Ala Gly Leu Ser Leu Val Ile Leu Pro Pro<br>         950                     955                     960 | 3476 |

```
                                                          -continued tta ttc cct tat tta gaa cca caa gaa gca gag cta gta att caa ata        3524
Leu Phe Pro Tyr Leu Glu Pro Gln Glu Ala Glu Leu Val Ile Gln Ile
965             970             975             980 ttt gat ttt att tct tct gac aca cac aag tgc cta caa gga tta aag        3572
Phe Asp Phe Ile Ser Ser Asp Thr His Lys Cys Leu Gln Gly Leu Lys
                985             990             995 tgg gct atc ccc acc agt ctg gat tca gcg tgc ttt agc ctt aag            3617
Trp Ala Ile Pro Thr Ser Leu Asp Ser Ala Cys Phe Ser Leu Lys
1000            1005            1010 gct aaa gaa ata ttc tgt tcg ctt caa aat gaa gat ttt tac tct            3662
Ala Lys Glu Ile Phe Cys Ser Leu Gln Asn Glu Asp Phe Tyr Ser
    1015            1020            1025 gag ctt caa agt ata att aag tgt tta act aac gaa aat gag cca            3707
Glu Leu Gln Ser Ile Ile Lys Cys Leu Thr Asn Glu Asn Glu Pro
1030            1035            1040 gtt tgt tat tta ggt tta caa aaa tta gaa ctt ttt ttt caa gcc            3752
Val Cys Tyr Leu Gly Leu Gln Lys Leu Glu Leu Phe Phe Gln Ala
    1045            1050            1055 aag gtg gac gag tta cat gac aca cta aat ttg gac ata tcc aac            3797
Lys Val Asp Glu Leu His Asp Thr Leu Asn Leu Asp Ile Ser Asn
1060            1065            1070 gaa gtt ctg gac caa tta cta aga tgc ctt tta gat tgt tgt gta            3842
Glu Val Leu Asp Gln Leu Leu Arg Cys Leu Leu Asp Cys Cys Val
    1075            1080            1085 aaa tat gct tca aca aat atg caa ata tca tat ctt gct gca aaa            3887
Lys Tyr Ala Ser Thr Asn Met Gln Ile Ser Tyr Leu Ala Ala Lys
1090            1095            1100 aat ctt ggt gaa ttg ggt gcg ata gat ccc agc cgc gcc aag gct            3932
Asn Leu Gly Glu Leu Gly Ala Ile Asp Pro Ser Arg Ala Lys Ala
    1105            1110            1115 caa cat att att aaa gaa aca gtt gtt ctt gat aac ttt gaa aac            3977
Gln His Ile Ile Lys Glu Thr Val Val Leu Asp Asn Phe Glu Asn
1120            1125            1130 gga gaa gaa agt ttg aag ttt att cta gat ttt atg caa tcg cag            4022
Gly Glu Glu Ser Leu Lys Phe Ile Leu Asp Phe Met Gln Ser Gln
    1135            1140            1145 tta att cca gct ttc ctt gtt act act gat act aaa gca caa ggt            4067
Leu Ile Pro Ala Phe Leu Val Thr Thr Asp Thr Lys Ala Gln Gly
1150            1155            1160 ttt ctt gcc tat gct ctg caa gag ttt cta aag ctt ggt gga ttc            4112
Phe Leu Ala Tyr Ala Leu Gln Glu Phe Leu Lys Leu Gly Gly Phe
    1165            1170            1175 aag tcc gca gtg att aat aaa aaa aag gga cta act gtg gta aca            4157
Lys Ser Ala Val Ile Asn Lys Lys Lys Gly Leu Thr Val Val Thr
1180            1185            1190 gaa cat tgg atg tct ttg cct gat tta tcc aaa cgt gtg ctt ata            4202
Glu His Trp Met Ser Leu Pro Asp Leu Ser Lys Arg Val Leu Ile
    1195            1200            1205 cca ttt tta act tcc aag tat cat tta aca cca atc ccc aaa att            4247
Pro Phe Leu Thr Ser Lys Tyr His Leu Thr Pro Ile Pro Lys Ile
1210            1215            1220 gac att cgg tac cct att tat aaa gaa aat gtt act att cat act            4292
Asp Ile Arg Tyr Pro Ile Tyr Lys Glu Asn Val Thr Ile His Thr
    1225            1230            1235 tgg atg cag ttg ttt tct ctt aaa ttg atg gag tac gcc cat tcg            4337
Trp Met Gln Leu Phe Ser Leu Lys Leu Met Glu Tyr Ala His Ser
1240            1245            1250 caa aac gct gaa aaa ata ttt ggt att tgt tcg aaa gta gtg aaa            4382
Gln Asn Ala Glu Lys Ile Phe Gly Ile Cys Ser Lys Val Val Lys
    1255            1260            1265
```

```
gac caa gag gtt aac att ccc tgt ttt ctt ctt ccc ttt ctt gtt      4427
Asp Gln Glu Val Asn Ile Pro Cys Phe Leu Leu Pro Phe Leu Val
            1270                1275                1280 tta aat gtt att tta acc gag tca gaa ctg gaa gtt aat aaa gtc      4472
Leu Asn Val Ile Leu Thr Glu Ser Glu Leu Glu Val Asn Lys Val
        1285                1290                1295 att gaa gaa ttc cag ctt gtt att aat caa ccg gga cct gat gga      4517
Ile Glu Glu Phe Gln Leu Val Ile Asn Gln Pro Gly Pro Asp Gly
    1300                1305                1310 tta aat tcc gtg ggg caa caa aga tac acc tca ttt gta gat gta      4562
Leu Asn Ser Val Gly Gln Gln Arg Tyr Thr Ser Phe Val Asp Val
1315                1320                1325 ttt ttt aag att gtg gat tac ctt aac aaa tgg ctt cgc atg cga      4607
Phe Phe Lys Ile Val Asp Tyr Leu Asn Lys Trp Leu Arg Met Arg
            1330                1335                1340 aag aag agg aat tgg gat aga cgt tct gcc att gca agg aaa gag      4652
Lys Lys Arg Asn Trp Asp Arg Arg Ser Ala Ile Ala Arg Lys Glu
        1345                1350                1355 aac cgt tat atg tcg gtg gaa gat gct acc tct cga gaa tca tcg      4697
Asn Arg Tyr Met Ser Val Glu Asp Ala Thr Ser Arg Glu Ser Ser
    1360                1365                1370 atc tca aaa gtt gag tca ttt ctt tct cga ttt cct tca aaa aca      4742
Ile Ser Lys Val Glu Ser Phe Leu Ser Arg Phe Pro Ser Lys Thr
1375                1380                1385 tta ggt att gtc tct tta aat tgt gga ttt cat gct cgt gca ttg      4787
Leu Gly Ile Val Ser Leu Asn Cys Gly Phe His Ala Arg Ala Leu
            1390                1395                1400 ttt tat tgg gag caa cac ata cgt aat gct aca gct cca tat gca      4832
Phe Tyr Trp Glu Gln His Ile Arg Asn Ala Thr Ala Pro Tyr Ala
        1405                1410                1415 gct tta gag tcc gat tat aga gtt ttg cag gaa ata tat gct gga      4877
Ala Leu Glu Ser Asp Tyr Arg Val Leu Gln Glu Ile Tyr Ala Gly
    1420                1425                1430 att gat gat cca gat gaa atc gaa gca gtg tct tta aat ttc cat      4922
Ile Asp Asp Pro Asp Glu Ile Glu Ala Val Ser Leu Asn Phe His
1435                1440                1445 gat tac tcg ttt gat caa caa ctc ctt tta cat gaa aat tca gga      4967
Asp Tyr Ser Phe Asp Gln Gln Leu Leu Leu His Glu Asn Ser Gly
            1450                1455                1460 aca tgg gac tcg gct ttg agt tgt tac gaa att att att caa aag      5012
Thr Trp Asp Ser Ala Leu Ser Cys Tyr Glu Ile Ile Ile Gln Lys
        1465                1470                1475 gat cct gaa aat aaa aag gcg aaa atc ggt ttg ctt aac agc atg      5057
Asp Pro Glu Asn Lys Lys Ala Lys Ile Gly Leu Leu Asn Ser Met
    1480                1485                1490 ctg caa tcg ggg cat tat gaa tct ctt gtt ttg agt tta gat tct      5102
Leu Gln Ser Gly His Tyr Glu Ser Leu Val Leu Ser Leu Asp Ser
1495                1500                1505 ttt ata atc aat gac aac cac gag tat tcg aag atg tta aat ttg      5147
Phe Ile Ile Asn Asp Asn His Glu Tyr Ser Lys Met Leu Asn Leu
            1510                1515                1520 ggt att gaa gct tca tgg cgt tcg cta tct att gat tcg tta aaa      5192
Gly Ile Glu Ala Ser Trp Arg Ser Leu Ser Ile Asp Ser Leu Lys
        1525                1530                1535 aag tgt ctt tca aaa agc aac ttg gaa tct ttc gaa gct aaa ttg      5237
Lys Cys Leu Ser Lys Ser Asn Leu Glu Ser Phe Glu Ala Lys Leu
    1540                1545                1550 ggt agc ata ttt tac caa tac cta cgg aag gat tct ttt gct gaa      5282
Gly Ser Ile Phe Tyr Gln Tyr Leu Arg Lys Asp Ser Phe Ala Glu
1555                1560                1565
```

-continued

| | | | | | | | | | | | | | |
|---|---|---|---|---|---|---|---|---|---|---|---|---|---|
| ttg | acg | gag | cgg | ctg | caa | ccc | ttg | tac | gtt | gat | gct | gct | aca | gca | 5327 |
| Leu | Thr | Glu | Arg | Leu | Gln | Pro | Leu | Tyr | Val | Asp | Ala | Ala | Thr | Ala |
| | | 1570 | | | | 1575 | | | | 1580 | | | |
| att | gca | aac | aca | ggc | gcc | cat | tca | gcc | tat | gat | tgt | tat | gat | att | 5372 |
| Ile | Ala | Asn | Thr | Gly | Ala | His | Ser | Ala | Tyr | Asp | Cys | Tyr | Asp | Ile |
| | 1585 | | | | 1590 | | | | 1595 | | | |
| tta | tct | aag | ctg | cac | gca | att | aat | gac | ttt | agt | agg | att | gct | gaa | 5417 |
| Leu | Ser | Lys | Leu | His | Ala | Ile | Asn | Asp | Phe | Ser | Arg | Ile | Ala | Glu |
| 1600 | | | | 1605 | | | | 1610 | | | |
| act | gac | gga | att | gtt | tcc | gac | aat | ctt | gat | att | gtt | ctt | cgc | cgt | 5462 |
| Thr | Asp | Gly | Ile | Val | Ser | Asp | Asn | Leu | Asp | Ile | Val | Leu | Arg | Arg |
| | | 1615 | | | | 1620 | | | | 1625 | | | |
| cgg | ctt | agc | caa | gta | gct | ccg | tac | ggt | aaa | ttc | aag | cac | caa | atc | 5507 |
| Arg | Leu | Ser | Gln | Val | Ala | Pro | Tyr | Gly | Lys | Phe | Lys | His | Gln | Ile |
| | 1630 | | | | 1635 | | | | 1640 | | | |
| ctg | tcc | act | cac | tta | gtt | ggc | tat | gaa | aaa | ttt | gaa | aac | acg | aag | 5552 |
| Leu | Ser | Thr | His | Leu | Val | Gly | Tyr | Glu | Lys | Phe | Glu | Asn | Thr | Lys |
| 1645 | | | | 1650 | | | | 1655 | | | |
| aaa | act | gct | gaa | ata | tat | ctc | gag | att | gca | aga | ata | tct | cga | aaa | 5597 |
| Lys | Thr | Ala | Glu | Ile | Tyr | Leu | Glu | Ile | Ala | Arg | Ile | Ser | Arg | Lys |
| | | 1660 | | | | 1665 | | | | 1670 | | | |
| aat | ggt | caa | ttt | caa | aga | gcc | ttc | aat | gcc | atc | ctc | aaa | gca | atg | 5642 |
| Asn | Gly | Gln | Phe | Gln | Arg | Ala | Phe | Asn | Ala | Ile | Leu | Lys | Ala | Met |
| | 1675 | | | | 1680 | | | | 1685 | | | |
| gat | tta | gat | aaa | ccg | cta | gca | aca | ata | gag | cac | gca | caa | tgg | tgg | 5687 |
| Asp | Leu | Asp | Lys | Pro | Leu | Ala | Thr | Ile | Glu | His | Ala | Gln | Trp | Trp |
| 1690 | | | | 1695 | | | | 1700 | | | |
| tgg | cat | caa | ggg | caa | cat | cgt | aaa | gct | att | tct | gaa | ttg | aat | ttt | 5732 |
| Trp | His | Gln | Gly | Gln | His | Arg | Lys | Ala | Ile | Ser | Glu | Leu | Asn | Phe |
| | | 1705 | | | | 1710 | | | | 1715 | | | |
| tcg | ctt | aat | aac | aac | atg | ttt | gat | ttg | gtt | gat | gag | cat | gaa | gaa | 5777 |
| Ser | Leu | Asn | Asn | Asn | Met | Phe | Asp | Leu | Val | Asp | Glu | His | Glu | Glu |
| | 1720 | | | | 1725 | | | | 1730 | | | |
| aga | cct | aaa | aat | cgt | aaa | gaa | act | tta | gga | aat | cca | ctt | aaa | gga | 5822 |
| Arg | Pro | Lys | Asn | Arg | Lys | Glu | Thr | Leu | Gly | Asn | Pro | Leu | Lys | Gly |
| 1735 | | | | 1740 | | | | 1745 | | | |
| aaa | gtg | ttc | ttg | aaa | ctt | aca | aaa | tgg | ctc | gga | aaa | gct | ggc | caa | 5867 |
| Lys | Val | Phe | Leu | Lys | Leu | Thr | Lys | Trp | Leu | Gly | Lys | Ala | Gly | Gln |
| | | 1750 | | | | 1755 | | | | 1760 | | | |
| ctg | gga | ttg | aag | gat | ttg | gag | acg | tat | tat | cat | aaa | gcg | gta | gag | 5912 |
| Leu | Gly | Leu | Lys | Asp | Leu | Glu | Thr | Tyr | Tyr | His | Lys | Ala | Val | Glu |
| | 1765 | | | | 1770 | | | | 1775 | | | |
| att | tac | tca | gaa | tgt | gag | aat | acg | cat | tat | tat | ctt | ggc | cat | cat | 5957 |
| Ile | Tyr | Ser | Glu | Cys | Glu | Asn | Thr | His | Tyr | Tyr | Leu | Gly | His | His |
| 1780 | | | | 1785 | | | | 1790 | | | |
| cga | gtt | tta | atg | tat | gaa | gaa | gaa | caa | aag | ctc | cca | gtt | aat | gaa | 6002 |
| Arg | Val | Leu | Met | Tyr | Glu | Glu | Glu | Gln | Lys | Leu | Pro | Val | Asn | Glu |
| | | 1795 | | | | 1800 | | | | 1805 | | | |
| cag | agc | gaa | cga | ttt | tta | agt | ggt | gag | tta | gta | act | cgc | ata | att | 6047 |
| Gln | Ser | Glu | Arg | Phe | Leu | Ser | Gly | Glu | Leu | Val | Thr | Arg | Ile | Ile |
| | 1810 | | | | 1815 | | | | 1820 | | | |
| aac | gaa | ttt | ggt | cga | tct | ttg | tac | tat | ggt | aca | aat | cat | ata | tat | 6092 |
| Asn | Glu | Phe | Gly | Arg | Ser | Leu | Tyr | Tyr | Gly | Thr | Asn | His | Ile | Tyr |
| 1825 | | | | 1830 | | | | 1835 | | | |
| gaa | agt | atg | cca | aaa | ttg | ctc | aca | ctg | tgg | ctt | gat | ttt | ggg | gcc | 6137 |
| Glu | Ser | Met | Pro | Lys | Leu | Leu | Thr | Leu | Trp | Leu | Asp | Phe | Gly | Ala |
| | | 1840 | | | | 1845 | | | | 1850 | | | |
| gaa | gaa | ctt | cgc | tta | tct | aaa | gat | gac | ggc | gaa | aag | tac | ttt | cgt | 6182 |
| Glu | Glu | Leu | Arg | Leu | Ser | Lys | Asp | Asp | Gly | Glu | Lys | Tyr | Phe | Arg |
| | 1855 | | | | 1860 | | | | 1865 | | | |

-continued

| | | |
|---|---|---|
| gaa cac att atc tct tcg aga aaa aaa tct ttg gaa ctt atg aat<br>Glu His Ile Ile Ser Ser Arg Lys Lys Ser Leu Glu Leu Met Asn<br>1870                                    1875                               1880 | 6227 |

| tcg aat gtt tgt cgc ctt tct atg aaa att cct caa tac ttt ttt<br>Ser Asn Val Cys Arg Leu Ser Met Lys Ile Pro Gln Tyr Phe Phe<br>1885 1890 1895 | 6272 |
| ctg gtt gca tta tcc caa atg ata tcc aga gta tgc cat cca aat<br>Leu Val Ala Leu Ser Gln Met Ile Ser Arg Val Cys His Pro Asn<br>1900 1905 1910 | 6317 |
| aat aaa gtt tat aaa att ttg gaa cat ata att gca aac gtt gta<br>Asn Lys Val Tyr Lys Ile Leu Glu His Ile Ile Ala Asn Val Val<br>1915 1920 1925 | 6362 |
| gca tct tat cct ggg gag acg cta tgg caa tta atg gca aca ata<br>Ala Ser Tyr Pro Gly Glu Thr Leu Trp Gln Leu Met Ala Thr Ile<br>1930 1935 1940 | 6407 |
| aaa tcg act tct caa aag cgc tcg ctt cgt gga aaa agc att tta<br>Lys Ser Thr Ser Gln Lys Arg Ser Leu Arg Gly Lys Ser Ile Leu<br>1945 1950 1955 | 6452 |
| aat gtt tta cat tct agg aag ctt tct atg tct tcc aaa gtt gat<br>Asn Val Leu His Ser Arg Lys Leu Ser Met Ser Ser Lys Val Asp<br>1960 1965 1970 | 6497 |
| ata aaa gca ctc agt caa tct gca att ctc att act gaa aag tta<br>Ile Lys Ala Leu Ser Gln Ser Ala Ile Leu Ile Thr Glu Lys Leu<br>1975 1980 1985 | 6542 |
| atc aat ttg tgc aat aca agg att aac agt aaa tct gta aaa atg<br>Ile Asn Leu Cys Asn Thr Arg Ile Asn Ser Lys Ser Val Lys Met<br>1990 1995 2000 | 6587 |
| agc tta aag gat cat ttt cgg ctt tct ttt gat gat ccg gta gat<br>Ser Leu Lys Asp His Phe Arg Leu Ser Phe Asp Asp Pro Val Asp<br>2005 2010 2015 | 6632 |
| tta gtc att cct gct aaa tca ttt tta gac att act tta cca gct<br>Leu Val Ile Pro Ala Lys Ser Phe Leu Asp Ile Thr Leu Pro Ala<br>2020 2025 2030 | 6677 |
| aaa gat gct aac aga gct agt cat tat cca ttt cca aaa act cag<br>Lys Asp Ala Asn Arg Ala Ser His Tyr Pro Phe Pro Lys Thr Gln<br>2035 2040 2045 | 6722 |
| cct act ctg ttg aaa ttt gag gat gag gtg gat ata atg aac tct<br>Pro Thr Leu Leu Lys Phe Glu Asp Glu Val Asp Ile Met Asn Ser<br>2050 2055 2060 | 6767 |
| ctt caa aaa cca aga aaa gtg tac gtt aga ggt acg gat ggc aac<br>Leu Gln Lys Pro Arg Lys Val Tyr Val Arg Gly Thr Asp Gly Asn<br>2065 2070 2075 | 6812 |
| tta tac cca ttc ttg tgc aaa ccc aaa gat gat ctt cgt aag gat<br>Leu Tyr Pro Phe Leu Cys Lys Pro Lys Asp Asp Leu Arg Lys Asp<br>2080 2085 2090 | 6857 |
| gct aga ttg atg gaa ttt aat aat ctt att tgt aaa ata ttg agg<br>Ala Arg Leu Met Glu Phe Asn Asn Leu Ile Cys Lys Ile Leu Arg<br>2095 2100 2105 | 6902 |
| aaa gat caa gaa gcg aac aga agg aac ttg tgt att aga act tat<br>Lys Asp Gln Glu Ala Asn Arg Arg Asn Leu Cys Ile Arg Thr Tyr<br>2110 2115 2120 | 6947 |
| gtt gtt att cct tta aat gaa gaa tgc gga ttt atc gaa tgg gta<br>Val Val Ile Pro Leu Asn Glu Glu Cys Gly Phe Ile Glu Trp Val<br>2125 2130 2135 | 6992 |
| aat cat act cgt cca ttt aga gaa att ttg tta aaa agc tat aga<br>Asn His Thr Arg Pro Phe Arg Glu Ile Leu Leu Lys Ser Tyr Arg<br>2140 2145 2150 | 7037 |
| cag aaa aac att ccc ata tca tat caa gaa atc aaa gtt gat tta<br>Gln Lys Asn Ile Pro Ile Ser Tyr Gln Glu Ile Lys Val Asp Leu<br>2155 2160 2165 | 7082 |

```
gac ttt gca ctg cga agt cct aac cct ggt gat ata ttt gaa aag      7127
Asp Phe Ala Leu Arg Ser Pro Asn Pro Gly Asp Ile Phe Glu Lys
            2170                2175                2180 aaa atc tta ccg aaa ttt cct cca gtt ttt tat gag tgg ttt gtt      7172
Lys Ile Leu Pro Lys Phe Pro Pro Val Phe Tyr Glu Trp Phe Val
            2185                2190                2195 gaa tct ttc cca gaa cca aat aat tgg gtt act agt aga caa aac      7217
Glu Ser Phe Pro Glu Pro Asn Asn Trp Val Thr Ser Arg Gln Asn
            2200                2205                2210 tat tgc cga act tta gca gta atg tca ata gtt ggc tac gtt ttg      7262
Tyr Cys Arg Thr Leu Ala Val Met Ser Ile Val Gly Tyr Val Leu
            2215                2220                2225 ggt ttg gga gat cgc cat ggc gaa aac ata ttg ttt gat gaa ttt      7307
Gly Leu Gly Asp Arg His Gly Glu Asn Ile Leu Phe Asp Glu Phe
            2230                2235                2240 aca ggt gaa gct atc cat gtc gat ttc aac tgt ctt ttt gat aaa      7352
Thr Gly Glu Ala Ile His Val Asp Phe Asn Cys Leu Phe Asp Lys
            2245                2250                2255 ggt ctt act ttt gaa aaa cct gaa aag gtg ccg ttc aga tta act      7397
Gly Leu Thr Phe Glu Lys Pro Glu Lys Val Pro Phe Arg Leu Thr
            2260                2265                2270 cat aat atg gta gat gca atg ggt ccg aca ggt tat gaa ggg ggt      7442
His Asn Met Val Asp Ala Met Gly Pro Thr Gly Tyr Glu Gly Gly
            2275                2280                2285 ttc agg aaa gct agc gaa ata acg atg cgg ctt ctt cgc tca aac      7487
Phe Arg Lys Ala Ser Glu Ile Thr Met Arg Leu Leu Arg Ser Asn
            2290                2295                2300 caa gat aca ttg atg agc gta cta gag tct ttc cta cat gat cct      7532
Gln Asp Thr Leu Met Ser Val Leu Glu Ser Phe Leu His Asp Pro
            2305                2310                2315 tta gtc gag tgg aat aga aag aag tcg tca agc aag tac ccg aat      7577
Leu Val Glu Trp Asn Arg Lys Lys Ser Ser Ser Lys Tyr Pro Asn
            2320                2325                2330 aat gaa gca aat gaa gtt ttg gat ata att cgc aaa aaa ttt caa      7622
Asn Glu Ala Asn Glu Val Leu Asp Ile Ile Arg Lys Lys Phe Gln
            2335                2340                2345 ggc ttt atg cca ggg gag acg ata cct tta tct att gaa ggg caa      7667
Gly Phe Met Pro Gly Glu Thr Ile Pro Leu Ser Ile Glu Gly Gln
            2350                2355                2360 att caa gaa ttg atc aaa tct gct gtc aac cca aaa aac ctg gta      7712
Ile Gln Glu Leu Ile Lys Ser Ala Val Asn Pro Lys Asn Leu Val
            2365                2370                2375 gaa atg tac att ggt tgg gct gct tat ttc tagcatttta ctaacaaaaa    7762
Glu Met Tyr Ile Gly Trp Ala Ala Tyr Phe
            2380                2385 tttcaatgaa caagctaccc attattaaac ttatgatttg aatcgaagat atttatttta 7822 ttaatccgat gaagaattct cgctgagttg ttcaatttct tgtaattttc cttccatttc 7882 taaatcgtcg attcgcttaa ataggggcact ggcttttttgt gcattttttct ctcgtaaagc 7942 agcttctgat tgaaaaaaag ctatatctgt ttctgagtca tcatccgaat caacaatata 8002 ttttgcagat cgacctgcag                                            8022

<210> SEQ ID NO 4
<211> LENGTH: 2386
<212> TYPE: PRT
<213> ORGANISM: Homo sapiens
```

-continued

```
<400> SEQUENCE: 4

Met Ser Gln His Ala Lys Arg Lys Ala Gly Ser Leu Asp Leu Ser Pro
1               5                   10                  15

Arg Gly Leu Asp Asp Arg Gln Ala Phe Gly Gln Leu Leu Lys Glu Val
            20                  25                  30

Leu Ala Leu Asp Lys Glu His Glu Leu Gly Arg Ser Asn Ser Leu Pro
        35                  40                  45

Ser Met Thr Ser Glu Leu Val Glu Val Leu Ile Glu Val Gly Leu Leu
    50                  55                  60

Ala Phe Lys His Asp Asp Ser Lys Ser Glu Phe Ile Ser Pro Lys Met
65                  70                  75                  80

Leu Lys Glu Ala His Leu Ser Leu Gln Ala Leu Met Leu Ile Leu Lys
                85                  90                  95

Arg Ser Pro Thr Val Leu Arg Glu Ile Lys Ser Ser Val Thr Leu Leu
            100                 105                 110

Asp Trp Ile Leu Pro Arg Thr Ile Ser Leu Phe Ala Asp Ile Arg Phe
        115                 120                 125

Ile Lys Leu Phe Asp Ser Leu Lys Glu Phe His Lys Leu Ile Tyr Gln
130                 135                 140

Leu Ile Ser Glu Lys Ser Phe Leu Trp Asp Leu Tyr Ala Ser Phe Met
145                 150                 155                 160

Arg Tyr Trp Lys Tyr Tyr Ile Thr Asn Val Ser Ser Ile Val Leu Gln
                165                 170                 175

Ile Thr Asn Ala Thr Phe Pro Tyr Lys Met Pro Ser Pro Asn Ser Gln
            180                 185                 190

Pro Leu Gln Ser Ile Ser Pro Asn Tyr Pro Thr His Arg Glu Asp Lys
        195                 200                 205

Phe Asp Leu Leu Ile Ile Asn Ile Glu Glu Ala Cys Thr Phe Phe Phe
210                 215                 220

Glu Ser Ala His Phe Phe Ala Gln Cys Ser Tyr Leu Lys Lys Ser Asn
225                 230                 235                 240

Phe Pro Ser Pro Pro Leu Phe Thr Ala Trp Thr Trp Ile Lys Pro Cys
                245                 250                 255

Phe Phe Asn Phe Val Ile Leu Leu Lys Arg Ile Ser Ile Gly Asp Ser
            260                 265                 270

Gln Leu Phe Leu His Leu His Ser Arg Ile Val Gln Thr Leu Cys Cys
        275                 280                 285

Phe Ser Leu Asn Phe Ile Tyr His Gly Leu Pro Ile Cys Glu Lys Ser
290                 295                 300

Lys His Ile Leu Met Ser Ser Ile Asn Leu Thr Leu Gly Ser Leu Lys
305                 310                 315                 320

Lys Thr Tyr Thr Val Ala Asn Thr Ala Ile Ser Leu Phe Phe Leu Ser
                325                 330                 335

Leu Phe Val Leu Pro Lys Thr Val Ala Gly Leu Phe Tyr Pro Phe Gly
            340                 345                 350

Val Ser Leu Ser Asp Phe Lys Val Leu Glu Gln Leu Glu Pro Asp
        355                 360                 365

Ser Asp Leu Lys Lys Ala Ile Ile Leu Phe Lys Cys Arg Tyr Gln Ser
    370                 375                 380

Ser Glu Ile Asp Gln Thr Thr Leu Arg Ala Phe Gly Glu Ile Cys Thr
385                 390                 395                 400

Gly Lys Leu Glu Asn Thr Leu Phe Ser Asn Ser Glu Leu Asn Leu Phe
                405                 410                 415
```

-continued

```
Leu Leu His Tyr Leu Ser Leu Asp Asn Asp Leu Ser Asn Ile Leu Lys
            420                 425                 430

Val Asp Phe Gln Asn Gly His Asn Ile Cys Thr Phe Ala Lys Trp Cys
            435                 440                 445

Ile Asn Asn Asn Leu Asp Glu Pro Ser Asn Leu Lys His Phe Arg Glu
            450                 455                 460

Met Leu Asp Tyr Tyr Ser Ser His Asn Val Thr Ile Ser Glu Asp Asp
465                 470                 475                 480

Leu Lys Asn Phe Ser Leu Val Leu Cys Thr His Val Ala Lys Val Asn
                485                 490                 495

Glu Lys Thr Asn Ser Ile Phe Arg Thr Tyr Glu Val His Gly Cys Glu
                500                 505                 510

Val Cys Asn Ser Phe Cys Leu Leu Phe Asp Glu Arg Ser Pro Phe Lys
                515                 520                 525

Ile Pro Tyr His Glu Leu Phe Cys Ala Leu Leu Lys Asn Pro Asp Ile
                530                 535                 540

Ile Ser Ser Ser Val Lys Gln Ser Leu Leu Asp Gly Phe Phe Arg
545                 550                 555                 560

Trp Ser Gln His Cys Ser Asn Phe Asn Lys Glu Ser Met Leu Ser Leu
                565                 570                 575

Arg Glu Phe Ile Met Lys Ala Leu Ala Ser Thr Ser Arg Cys Leu Arg
                580                 585                 590

Val Val Ala Ala Lys Val Leu Pro Ile Phe Ile Lys Gly Pro Asn Asn
                595                 600                 605

Leu Asp Ile Val Glu Phe His Lys Glu Ser Lys Ala Leu Ile Phe Asn
                610                 615                 620

Thr Leu Lys Ile Leu Ala Val Glu Asn Thr Ala Ile Leu Glu Thr Val
625                 630                 635                 640

Ile Leu Ser Trp Ile Ser Leu Ser Arg Val Val Glu Glu Glu Leu
                645                 650                 655

His Phe Val Leu Leu Glu Val Ile Ser Ser Val Ile Asn Ser Gly Ile
                660                 665                 670

Phe Tyr Gln Gly Ile Gly Leu Ser Ala Leu Gln Gln Ile Ala Ser Thr
                675                 680                 685

Arg His Ile Ser Val Trp Gln Leu Leu Ser Pro Tyr Trp Pro Thr Val
                690                 695                 700

Ser Val Ala Ile Val Gln Gly Met Gly Lys Lys Pro Asn Ile Ala Ser
705                 710                 715                 720

Leu Phe Ala Gln Leu Met Asn Ile Ser Glu Gly Asp Phe Leu Ile Arg
                725                 730                 735

Thr Gln Ala Tyr Thr Leu Pro Phe Leu Val Leu Thr Lys Asn Lys Ala
                740                 745                 750

Leu Ile Val Arg Ile Ala Glu Leu Ser Gln Ser Asp Val Ala Thr Leu
                755                 760                 765

Cys Leu Thr Asn Met His Lys Ile Leu Ala Ser Leu Leu Thr Thr Asp
                770                 775                 780

His Pro Asn Leu Glu Glu Ser Val Met Leu Leu Ser Leu Ala Thr
785                 790                 795                 800

Ser Asp Phe Glu Lys Val Asp Leu Thr Ser Leu Leu Arg Ser Asp Pro
                805                 810                 815

Ile Ser Ile Thr Val Glu Leu Leu Gln Leu Tyr Gln Asn Asp Val Pro
                820                 825                 830
```

-continued

```
His Glu Lys Ile Glu Asn Ala Leu Arg Lys Val Ala Met Ile Val Ser
        835                 840                 845

Gln Val Val Asn Asp Glu Asp Leu Ser Asn Lys Glu Leu Leu Tyr Asp
        850                 855                 860

Phe Phe Asn Asn His Ile Leu Gly Ile Leu Ala Glu Phe Ser Asn Ile
865                 870                 875                 880

Leu Asn Asp Leu Lys Gly Lys Thr Ser Ile Asn Glu Lys Ile Lys Thr
                    885                 890                 895

Ile Val Gly Ile Glu Lys Met Leu Ser Leu Cys Gly Gly Ala Val Lys
                900                 905                 910

Leu Gly Leu Pro Gln Ile Leu Ser Asn Leu Gln Ser Ala Phe Gln Asn
        915                 920                 925

Glu His Leu Arg Phe Tyr Ala Ile Lys Ala Trp Phe Ser Leu Ile Leu
        930                 935                 940

Ala Thr Lys Glu Pro Glu Tyr Ser Ser Ile Ala Gly Leu Ser Leu Val
945                 950                 955                 960

Ile Leu Pro Pro Leu Phe Pro Tyr Leu Glu Pro Gln Glu Ala Glu Leu
                965                 970                 975

Val Ile Gln Ile Phe Asp Phe Ile Ser Ser Asp Thr His Lys Cys Leu
                980                 985                 990

Gln Gly Leu Lys Trp Ala Ile Pro  Thr Ser Leu Asp Ser  Ala Cys Phe
        995                 1000                  1005

Ser Leu Lys Ala Lys Glu Ile  Phe Cys Ser Leu Gln  Asn Glu Asp
        1010                 1015                  1020

Phe Tyr  Ser Glu Leu Gln Ser  Ile Ile Lys Cys Leu  Thr Asn Glu
        1025                 1030                  1035

Asn Glu  Pro Val Cys Tyr Leu  Gly Leu Gln Lys Leu  Glu Leu Phe
        1040                 1045                  1050

Phe Gln  Ala Lys Val Asp Glu  Leu His Asp Thr Leu  Asn Leu Asp
        1055                 1060                  1065

Ile Ser  Asn Glu Val Leu Asp  Gln Leu Leu Arg Cys  Leu Leu Asp
        1070                 1075                  1080

Cys Cys  Val Lys Tyr Ala Ser  Thr Asn Met Gln Ile  Ser Tyr Leu
        1085                 1090                  1095

Ala Ala  Lys Asn Leu Gly Glu  Leu Gly Ala Ile Asp  Pro Ser Arg
        1100                 1105                  1110

Ala Lys  Ala Gln His Ile Ile  Lys Glu Thr Val Val  Leu Asp Asn
        1115                 1120                  1125

Phe Glu  Asn Gly Glu Glu Ser  Leu Lys Phe Ile Leu  Asp Phe Met
        1130                 1135                  1140

Gln Ser  Gln Leu Ile Pro Ala  Phe Leu Val Thr Thr  Asp Thr Lys
        1145                 1150                  1155

Ala Gln  Gly Phe Leu Ala Tyr  Ala Leu Gln Glu Phe  Leu Lys Leu
        1160                 1165                  1170

Gly Gly  Phe Lys Ser Ala Val  Ile Asn Lys Lys Gly  Leu Thr
        1175                 1180                  1185

Val Val  Thr Glu His Trp Met  Ser Leu Pro Asp Leu  Ser Lys Arg
        1190                 1195                  1200

Val Leu  Ile Pro Phe Leu Thr  Ser Lys Tyr His Leu  Thr Pro Ile
        1205                 1210                  1215

Pro Lys  Ile Asp Ile Arg Tyr  Pro Ile Tyr Lys Glu  Asn Val Thr
        1220                 1225                  1230
```

-continued

```
Ile His Thr Trp Met Gln Leu Phe Ser Leu Lys Leu Met Glu Tyr
1235                1240                1245

Ala His Ser Gln Asn Ala Glu Lys Ile Phe Gly Ile Cys Ser Lys
1250                1255                1260

Val Val Lys Asp Gln Glu Val Asn Ile Pro Cys Phe Leu Leu Pro
1265                1270                1275

Phe Leu Val Leu Asn Val Ile Leu Thr Glu Ser Glu Leu Glu Val
1280                1285                1290

Asn Lys Val Ile Glu Glu Phe Gln Leu Val Ile Asn Gln Pro Gly
1295                1300                1305

Pro Asp Gly Leu Asn Ser Val Gly Gln Gln Arg Tyr Thr Ser Phe
1310                1315                1320

Val Asp Val Phe Phe Lys Ile Val Asp Tyr Leu Asn Lys Trp Leu
1325                1330                1335

Arg Met Arg Lys Lys Arg Asn Trp Asp Arg Arg Ser Ala Ile Ala
1340                1345                1350

Arg Lys Glu Asn Arg Tyr Met Ser Val Glu Asp Ala Thr Ser Arg
1355                1360                1365

Glu Ser Ser Ile Ser Lys Val Glu Ser Phe Leu Ser Arg Phe Pro
1370                1375                1380

Ser Lys Thr Leu Gly Ile Val Ser Leu Asn Cys Gly Phe His Ala
1385                1390                1395

Arg Ala Leu Phe Tyr Trp Glu Gln His Ile Arg Asn Ala Thr Ala
1400                1405                1410

Pro Tyr Ala Ala Leu Glu Ser Asp Tyr Arg Val Leu Gln Glu Ile
1415                1420                1425

Tyr Ala Gly Ile Asp Asp Pro Asp Glu Ile Glu Ala Val Ser Leu
1430                1435                1440

Asn Phe His Asp Tyr Ser Phe Asp Gln Gln Leu Leu His Glu
1445                1450                1455

Asn Ser Gly Thr Trp Asp Ser Ala Leu Ser Cys Tyr Glu Ile Ile
1460                1465                1470

Ile Gln Lys Asp Pro Glu Asn Lys Lys Ala Lys Ile Gly Leu Leu
1475                1480                1485

Asn Ser Met Leu Gln Ser Gly His Tyr Glu Ser Leu Val Leu Ser
1490                1495                1500

Leu Asp Ser Phe Ile Ile Asn Asp His Glu Tyr Ser Lys Met
1505                1510                1515

Leu Asn Leu Gly Ile Glu Ala Ser Trp Arg Ser Leu Ser Ile Asp
1520                1525                1530

Ser Leu Lys Lys Cys Leu Ser Lys Ser Asn Leu Glu Ser Phe Glu
1535                1540                1545

Ala Lys Leu Gly Ser Ile Phe Tyr Gln Tyr Leu Arg Lys Asp Ser
1550                1555                1560

Phe Ala Glu Leu Thr Glu Arg Leu Gln Pro Leu Tyr Val Asp Ala
1565                1570                1575

Ala Thr Ala Ile Ala Asn Thr Gly Ala His Ser Ala Tyr Asp Cys
1580                1585                1590

Tyr Asp Ile Leu Ser Lys Leu His Ala Ile Asn Asp Phe Ser Arg
1595                1600                1605

Ile Ala Glu Thr Asp Gly Ile Val Ser Asp Asn Leu Asp Ile Val
1610                1615                1620
```

-continued

```
Leu Arg Arg Arg Leu Ser Gln Val Ala Pro Tyr Gly Lys Phe Lys
1625                1630                1635

His Gln Ile Leu Ser Thr His Leu Val Gly Tyr Glu Lys Phe Glu
1640                1645                1650

Asn Thr Lys Lys Thr Ala Glu Ile Tyr Leu Glu Ile Ala Arg Ile
1655                1660                1665

Ser Arg Lys Asn Gly Gln Phe Gln Arg Ala Phe Asn Ala Ile Leu
1670                1675                1680

Lys Ala Met Asp Leu Asp Lys Pro Leu Ala Thr Ile Glu His Ala
1685                1690                1695

Gln Trp Trp His Gln Gly Gln His Arg Lys Ala Ile Ser Glu
1700                1705                1710

Leu Asn Phe Ser Leu Asn Asn Asn Met Phe Asp Leu Val Asp Glu
1715                1720                1725

His Glu Glu Arg Pro Lys Asn Arg Lys Glu Thr Leu Gly Asn Pro
1730                1735                1740

Leu Lys Gly Lys Val Phe Leu Lys Leu Thr Lys Trp Leu Gly Lys
1745                1750                1755

Ala Gly Gln Leu Gly Leu Lys Asp Leu Glu Thr Tyr Tyr His Lys
1760                1765                1770

Ala Val Glu Ile Tyr Ser Glu Cys Glu Asn Thr His Tyr Tyr Leu
1775                1780                1785

Gly His His Arg Val Leu Met Tyr Glu Glu Glu Gln Lys Leu Pro
1790                1795                1800

Val Asn Glu Gln Ser Glu Arg Phe Leu Ser Gly Glu Leu Val Thr
1805                1810                1815

Arg Ile Ile Asn Glu Phe Gly Arg Ser Leu Tyr Tyr Gly Thr Asn
1820                1825                1830

His Ile Tyr Glu Ser Met Pro Lys Leu Leu Thr Leu Trp Leu Asp
1835                1840                1845

Phe Gly Ala Glu Glu Leu Arg Leu Ser Lys Asp Asp Gly Glu Lys
1850                1855                1860

Tyr Phe Arg Glu His Ile Ile Ser Ser Arg Lys Lys Ser Leu Glu
1865                1870                1875

Leu Met Asn Ser Asn Val Cys Arg Leu Ser Met Lys Ile Pro Gln
1880                1885                1890

Tyr Phe Phe Leu Val Ala Leu Ser Gln Met Ile Ser Arg Val Cys
1895                1900                1905

His Pro Asn Asn Lys Val Tyr Lys Ile Leu Glu His Ile Ile Ala
1910                1915                1920

Asn Val Val Ala Ser Tyr Pro Gly Glu Thr Leu Trp Gln Leu Met
1925                1930                1935

Ala Thr Ile Lys Ser Thr Ser Gln Lys Arg Ser Leu Arg Gly Lys
1940                1945                1950

Ser Ile Leu Asn Val Leu His Ser Arg Lys Leu Ser Met Ser Ser
1955                1960                1965

Lys Val Asp Ile Lys Ala Leu Ser Gln Ser Ala Ile Leu Ile Thr
1970                1975                1980

Glu Lys Leu Ile Asn Leu Cys Asn Thr Arg Ile Asn Ser Lys Ser
1985                1990                1995

Val Lys Met Ser Leu Lys Asp His Phe Arg Leu Ser Phe Asp Asp
2000                2005                2010
```

```
Pro Val Asp Leu Val Ile Pro Ala Lys Ser Phe Leu Asp Ile Thr
2015                2020                 2025

Leu Pro Ala Lys Asp Ala Asn Arg Ala Ser His Tyr Pro Phe Pro
2030                2035                 2040

Lys Thr Gln Pro Thr Leu Leu Lys Phe Glu Asp Glu Val Asp Ile
2045                2050                 2055

Met Asn Ser Leu Gln Lys Pro Arg Lys Val Tyr Val Arg Gly Thr
2060                2065                 2070

Asp Gly Asn Leu Tyr Pro Phe Leu Cys Lys Pro Lys Asp Asp Leu
2075                2080                 2085

Arg Lys Asp Ala Arg Leu Met Glu Phe Asn Asn Leu Ile Cys Lys
2090                2095                 2100

Ile Leu Arg Lys Asp Gln Glu Ala Asn Arg Arg Asn Leu Cys Ile
2105                2110                 2115

Arg Thr Tyr Val Val Ile Pro Leu Asn Glu Glu Cys Gly Phe Ile
2120                2125                 2130

Glu Trp Val Asn His Thr Arg Pro Phe Arg Glu Ile Leu Leu Lys
2135                2140                 2145

Ser Tyr Arg Gln Lys Asn Ile Pro Ile Ser Tyr Gln Glu Ile Lys
2150                2155                 2160

Val Asp Leu Asp Phe Ala Leu Arg Ser Pro Asn Pro Gly Asp Ile
2165                2170                 2175

Phe Glu Lys Lys Ile Leu Pro Lys Phe Pro Pro Val Phe Tyr Glu
2180                2185                 2190

Trp Phe Val Glu Ser Phe Pro Glu Pro Asn Asn Trp Val Thr Ser
2195                2200                 2205

Arg Gln Asn Tyr Cys Arg Thr Leu Ala Val Met Ser Ile Val Gly
2210                2215                 2220

Tyr Val Leu Gly Leu Gly Asp Arg His Gly Glu Asn Ile Leu Phe
2225                2230                 2235

Asp Glu Phe Thr Gly Glu Ala Ile His Val Asp Phe Asn Cys Leu
2240                2245                 2250

Phe Asp Lys Gly Leu Thr Phe Glu Lys Pro Glu Lys Val Pro Phe
2255                2260                 2265

Arg Leu Thr His Asn Met Val Asp Ala Met Gly Pro Thr Gly Tyr
2270                2275                 2280

Glu Gly Gly Phe Arg Lys Ala Ser Glu Ile Thr Met Arg Leu Leu
2285                2290                 2295

Arg Ser Asn Gln Asp Thr Leu Met Ser Val Leu Glu Ser Phe Leu
2300                2305                 2310

His Asp Pro Leu Val Glu Trp Asn Arg Lys Lys Ser Ser Ser Lys
2315                2320                 2325

Tyr Pro Asn Asn Glu Ala Asn Glu Val Leu Asp Ile Ile Arg Lys
2330                2335                 2340

Lys Phe Gln Gly Phe Met Pro Gly Glu Thr Ile Pro Leu Ser Ile
2345                2350                 2355

Glu Gly Gln Ile Gln Glu Leu Ile Lys Ser Ala Val Asn Pro Lys
2360                2365                 2370

Asn Leu Val Glu Met Tyr Ile Gly Trp Ala Ala Tyr Phe
2375                2380                 2385

<210> SEQ ID NO 5
<211> LENGTH: 30
<212> TYPE: DNA
```

```
<213> ORGANISM: Artificial sequence
<220> FEATURE:
<223> OTHER INFORMATION: Primer

<400> SEQUENCE: 5
gttttcgcca tggcgcgctc ccaaacccaa                                        30

<210> SEQ ID NO 6
<211> LENGTH: 30
<212> TYPE: DNA
<213> ORGANISM: Artificial sequence
<220> FEATURE:
<223> OTHER INFORMATION: Primer

<400> SEQUENCE: 6
ttcatcaaac aatatctttt cgccatggcg                                        30

<210> SEQ ID NO 7
<211> LENGTH: 30
<212> TYPE: DNA
<213> ORGANISM: Artificial sequence
<220> FEATURE:
<223> OTHER INFORMATION: Primer

<400> SEQUENCE: 7
caaaaagaca gttgaattcg acatggatag                                        30

<210> SEQ ID NO 8
<211> LENGTH: 33
<212> TYPE: DNA
<213> ORGANISM: Artificial sequence
<220> FEATURE:
<223> OTHER INFORMATION: Primer

<400> SEQUENCE: 8
gacgcagaat tcaccagtca agaatcaaa gag                                     33

<210> SEQ ID NO 9
<211> LENGTH: 20
<212> TYPE: DNA
<213> ORGANISM: Artificial sequence
<220> FEATURE:
<223> OTHER INFORMATION: Primer

<400> SEQUENCE: 9
tggatgatga cagctgtgtc                                                   20

<210> SEQ ID NO 10
<211> LENGTH: 20
<212> TYPE: DNA
<213> ORGANISM: Artificial sequence
<220> FEATURE:
<223> OTHER INFORMATION: Primer

<400> SEQUENCE: 10
tgtagtcgct gctcaatgtc                                                   20

<210> SEQ ID NO 11
<211> LENGTH: 23
<212> TYPE: DNA
<213> ORGANISM: Artificial sequence
<220> FEATURE:
<223> OTHER INFORMATION: Primer

<400> SEQUENCE: 11
tggtttctga gaacattccc tga                                               23
```

```
<210> SEQ ID NO 12
<211> LENGTH: 10
<212> TYPE: PRT
<213> ORGANISM: Artificial sequence
<220> FEATURE:
<223> OTHER INFORMATION: Rad3/Esrlp
<221> NAME/KEY: MISC_FEATURE
<222> LOCATION: (5)..(5)
<223> OTHER INFORMATION: Xaa = Isoleucine or Valine
<221> NAME/KEY: MISC_FEATURE
<222> LOCATION: (6)..(6)
<223> OTHER INFORMATION: Xaa = Leucine or Phenylalanine
<221> NAME/KEY: MISC_FEATURE
<222> LOCATION: (8)..(8)
<223> OTHER INFORMATION: Xaa = Glutamine or Glutamic Acid

<400> SEQUENCE: 12

Lys Phe Pro Pro Xaa Xaa Tyr Xaa Trp Phe
1               5                   10

<210> SEQ ID NO 13
<211> LENGTH: 7
<212> TYPE: PRT
<213> ORGANISM: Artificial sequence
<220> FEATURE:
<223> OTHER INFORMATION: oligonucleutide oDH18

<400> SEQUENCE: 13

Leu Gly Leu Gly Asp Arg His
1               5

<210> SEQ ID NO 14
<211> LENGTH: 6
<212> TYPE: PRT
<213> ORGANISM: Artificial sequence
<220> FEATURE:
<223> OTHER INFORMATION: oligonucleotide oDH-16
<221> NAME/KEY: MISC_FEATURE
<222> LOCATION: (5)..(5)
<223> OTHER INFORMATION: Xaa = Aspartic Acid or Asparagine

<400> SEQUENCE: 14

His Val Asp Phe Xaa Cys
1               5
```

CELL-CYCLE CHECKPOINT GENES

This application claims priority of International Application No: PCT/GB96/09433, filed Sep. 6, 1996, which claims priority of Great Britain Application No: 9518220.0, filed Sep. 6, 1995.

The present invention relates to a class of checkpoint genes which control progression through the cell cycle in eukaryotic cells.

BACKGROUND OF THE INVENTION

Control of the cell cycle is fundamental to the growth and maintenance of eukaryotic organisms, from yeasts to mammals. Eukaryotic cells have evolved control pathways, termed "checkpoints" which ensure that individual steps of the cell cycle are completed before the next step occurs. In response to DNA damage, cell survival is increased both by direct DNA repair mechanisms and by delaying progression through the cell cycle. Depending on the position of the cell within the cycle at the time of irradiation, DNA damage in mammalian cells can prevent (a) passage from G1 into S phase, (b) progression through S phase or (c) passage from G2 into mitosis. Such checkpoints are thought to prevent deleterious events such as replication of damaged DNA and the segregation of fragmented chromosomes during mitosis (Hartwell and Kastan, 1994).

The rad3 gene of *Schizosaccharomyces pombe* is required for the checkpoints that respond to DNA damage and replication blocks. Rad3 is a member of the lipid kinase subclass of kinases which possess regions having sequence homology to the lipid kinase domain of the p110 subunit of phosphatidylinositol-3 kinase (PI-3 kinase). This subclass also includes the ATM protein defective in ataxia-telangiectasia patients. Cells from aeaxia telangiectasia patients (AT cells) have lost the delay to S phase following irradiation and are said to display radio resistant DNA synthesis (Painter and Young, 1989). AT cells irradiated in S phase accumulate in G2 with lethal damage, presumably as a consequence of attempting to replicate damaged DNA. AT cells irradiated during G2 display a different phenotype, they do not arrest mitosis after DNA damage, and progress through mitosis with damaged DNA (Beamish and Lavin, 1994). Mutations at the A-T locus, to which the ATM gene has been mapped, thus result in disruption of several checkpoints required for an appropriate response to ionising radiation. Other members of this lipid kinase subclass include: Tel1p (Greenwell et al. 1985). a gene involved in maintaining proper telomere length in *Saccharomyces cerevisiae;* Esr1p; Mec1p and the product of the *Drosophila melanogaster mei*-41 checkpoint gene (Hari et al. 1995).

DISCLOSURE OF THE INVENTION

We have analyzed the *S. pombe* rad3 gene and found that it has a full length amino acid sequence of 2386 amino acids, not the 1070 amino acids described by Seaton et al. 1992. We have determined that this is the direct homologue of *S. cerevisiae* Esr1p, and that it shares the same overall structure as the ATM gene. The C-terminal region of the rad3 protein contains a lipid kinase domain, which is required for Rad3 function We have shown that Rad3 is capable of self association. We have also identified a protein kinase activity associated with Rad3.

Further, we have found a human homologue to rad3. This gene, which we have named ATR (ataxia and rad related), displays significantly higher homology to rad3 than it does to the ATM gene.

The human ATR cDNA sequence is set out as Seq. ID No. 1. The amino acid sequence of the ORF from nucleotides 80 and 8011 is set out as Seq. ID No. 2.

The DNA sequence of the open reading frame (ORF) of rad3 is shown as Seq. ID. No. 3. The 2386 amino acid translation of the gene (nucleotides 585 to 7742 of Seq. ID No. 3) is shown as Seq. ID. No. 4.

Accordingly, in a first aspect, the invention provides the ATR protein of Seq. ID. 2 and homologues thereof, polypeptide fragments thereof, as well as antibodies capable of binding the ATR protein or polypeptide fragments thereof. ATR proteins, homologues and fragments thereof are referred to below as polypeptides of the invention.

In another aspect, the present invention provides a polynucleotide in substantially isolated form capable of hybridising selectively to Seq.ID No. 1 or to the complement (i.e. opposite stand) thereof. Also provided are polynucleotides encoding polypeptides of the invention.

Such polynucleotides will be referred to as a polynucleotide of die invention. A polynucleotides of the invention includes DNA of Seq.ID Nos. 1 and fragments thereof capable of selectively hybridising to this gene.

In a further aspect, the invention provides recombinant vectors carrying a polynucleotide of the invention, including expression vectors, and methods of growing such vectors in a suitable host cell, for example under conditions in which expression of a protein or polypeptide encoded by a sequence of the invention occurs.

In an additional aspect, the invention provides kits comprising polynucleotides, polypeptides or antibodies of the invention and methods of using such kits in diagnosing the presence of absence of ATR and its homologues, or variants thereof, including deleterious ATR mutants.

The invention further provides assay methods for screening candidate substances for use as compounds for inhibiting or activating ATR activity, or the activity of mutated forms of ATR which are deficient in checkpoint activity. The invention also provides assay methods for screening candidate substances for use as compounds for inhibiting interactions between ATR and other compounds that interact with ATR, including ATR itself.

In a related aspect, the invention also provides a polynucleotide sequence of Seq. ID No. 3 in substantially isolated form, and the protein of Seq. ID No. 4 in substantially isolated form, and novel fragments and variants thereof.

DETAILED DESCRIPTION OF THE INVENTION

A. Polynucleotides

Polynucleotides of the invention may comprise DNA or RNA. They may also be polynucleotides which include within them synthetic or modified nucleotides. A number of different types of modification to oligonucleotides are known in the an. These include methylphosphonate and phosphorothioate backbones, addition of acridine or polylysine chains at the 3' and/or 5' ends of the molecule. For the purposes of the present invention, it is to be understood that the polynucleotides described herein may be modified by any method available in the art. Such modifications may be carried out in order to enhance the in vivo activity or lifespan of polynucleotides of the invention.

Polynucleotides of the invention capable of selectively hybridizing to the DNA of Seq. ID No. 1 will be generally at least 70%, preferably at least 80 or 90% and more preferably at least 95% homologous to the corresponding DNA of Seq. ID No. 1 over a region of at least 20, preferably at least 25 or 30, for instance at least 40, 60 or 100 or more contiguous nucleotides.

It is to be understood that skilled persons may, using routine techniques, make nucleotide substitutions that do not affect the polypeptide sequence encoded by the polynucleotides of the invention to reflect the codon usage of any particular host organism in which the polypeptides of the invention are to be expressed.

Any combination of the above mentioned degrees of homology and minimum sizes may be used to define polynucleotides of the invention, with the more stringent combinations (i.e. higher homology over longer lengths) being preferred. Thus for example a polynucleotide which is at least 80% homologous over 25, preferably 30 nucleotides forms one aspect of the invention, as does a polynucleotide which is at least 90% homologous over 40 nucleotides.

Polynucleotides of the invention may be used to produce a primer, e.g. a PCR primer, a primer for an alternative amplification reaction, a probe e.g. labelled with a revealing label by conventional means using radioactive or non-radioactive labels, or the polynucleotides may be cloned into vectors. Such primers, probes and other fragments will be at least 15, preferably at least 20, for example at least 25, 30 or 40 nucleotides in length, and are also encompassed by the term polynucleotides of the invention as used herein.

Polynucleotides such as a DNA polynucleotide and primers according to the invention may be produced recombinantly, synthetically, or by any means available to those of skill in the art. They may also be cloned by standard techniques.

In general, primers will be produced by synthetic means, involving a step wise manufacture of the desired nucleic acid sequence one nucleotide at a time. Techniques for accomplishing this using automated techniques are readily available in the art.

Longer polynucleotides will generally be produced using recombinant means, for example using a PCR (polymerase chain reaction) cloning techniques. This will involve making a pair of primers (e.g. of about 15–30 nucleotides) to a region of the ATR gene which it is desired to clone, bringing the primers into contact with mRNA or cDNA obtained from a human cell (e.g. a dividing cell such as a peripheral blood leukocyte), performing a polymerase chain reaction under conditions which bring about amplification of the desired region, isolating the amplified fragment (e.g. by purifying the reaction mixture on an agarose gel) and recovering the amplified DNA. The primers may be designed to contain suitable restriction enzyme recognition sites so that be amplified DNA can be cloned into a suitable cloning vector.

Such techniques may be used to obtain all or part of the ATR sequence described herein. Genomic clones containing the ATR gene and its introns and promoter regions may also be obtained in an analogous manner, staring with genomic DNA from a human cell, e.g. a liver cell.

Although in general the techniques mentioned herein are well known in the art, reference may be made in particular to Sambrook et al. (Molecular Cloning: A Laboratory Manual, 1989).

Polynucleotides which are not 100% homologous to the sequences of the present invention but fall within the scope of the invention can be obtained in a number of ways.

Other human allelic variants of the ATR sequence described herein may be obtained for example by probing genomic DNA libraries made from a range of individuals, for example individuals from different populations.

In addition, other animal, particularly mammalian (e.g. mice, rats or rabbits), more particularly pa, homologues of ATR may be obtained and such homologues and fragments thereof in general will be capable of selectively hybridizing to Seq. ID No. 1. Such sequences may be obtained by probing cDNA libraries made from dividing cells or tissues or genomic DNA libraries from other animal species, and probing such libraries with probes comprising all or part of Seq. ID. 1 under conditions of medium to high stringency (for example 0.03M sodium chloride and 0.03M sodium citrate at from about 50° C. to about 60° C.).

Allelic variants and species homologues may also be obtained using degenerate PCR which will use primers designed to target sequences within the variants and homologues encoding conserved amino acid sequences. Conserved sequences can be predicted from aligning the AIR amino acid sequence with that of rad3. The primers will contain one or more degenerate positions and will be used at stringency conditions lower than those used for cloning sequences with single sequence primers against known sequences.

Alternatively, such polynucleotides may be obtained by site directed mutagenesis of the ATR sequences or allelic variants thereof. This may be useful where for example silent codon changes are required to sequences to optimise codon preferences for a particular host cell in which the polynucleotide sequences are being expressed. Other sequence changes may be desired in order to introduce restriction enzyme recognition sites, or to alter the property or function of the polypeptides encoded by the polynucleotides. Further changes may be desirable to represent particular coding changes found in ATR which give rise to mutant ATR genes which have lost the checkpoint fiction. Probes based on such changes can be used as diagnostic probes to detect such ATR mutants.

The invention further provides double stranded polynucleotides comprising a polynucleotide of the invention and its complement.

Polynucleotides or primers of the invention may carry a revealing label. Suitable labels include radioisotopes such as $^{32}P$ or $^{35}S$, enzyme labels, or other protein labels such as biotin. Such labels may be added to polynucleotides or primers of the invention and may be detected using by techniques known per se.

Polynucleotides or primers of the invention or fragments thereof labelled or unlabelled may be used by a person skilled in the art in nucleic acid-based tests for detecting or sequencing ATR in the human or animal body.

Such tests for detecting generally comprise bringing a human or animal body sample contain DNA or RNA into contact with a probe comprising a polynucleotide or primer of the invention under hybridizing conditions and detecting any duplex formed between the probe and nucleic acid in the sample. Such detection may be achieved using techniques such as PCR or by immobilizing the probe on a solid support, removing nucleic acid in the sample which is not hybridized to the probe, and then detecting nucleic acid which has hybridized to the probe. Alternatively, the sample nucleic acid may be immobilized on a solid support, and the amount of probe bound to such a support can be detected. Suitable assay methods of this any other formats can be found in for example WO89/03891 and WO90/13667.

Tests for sequencing ATR include bringing a human or animal body sample containing target DNA or RNA into contact with a probe comprising a polynucleotide or primer of the invention under hybridizing conditions and determining the she by, for example the Sanger dideoxy chain termination method (see Sambrook et al.).

Such a method generally comprises elongating, in the presence of suitable reagents, the primer by synthesis of a stand complementary to the target DNA or RNA and selectively terminating the elongation reaction at one or more of an A, C, G or T/U residue; allowing stand elongation and termination reaction to occur; separating out according to size the elongated products to determine the sequence of the nucleotides at which selective tenon has occurred. Suitable reagents include a DNA polymerase enzyme, the deoxynucleotides dATP, dCTP, dGTP and dTTP, a buffer and ATP. Dideoxynucleotides are used for selective termination.

Tests for detecting or sequencing ATR in the human or animal body may be used to determine ATR sequences within cells in individuals who have, or are suspected to have, an altered ATR gene sequence, for example within cancer cells including leukaemic cells and solid tumours such as breast, ovary, lung, colon, pancreas, testes, liver, brain, muscle and bone tumours.

In addition, the discovery of ATR will allow the role of this gene in hereditary diseases to be investigated, in a manner analogous to the ATM gene. In general, this will involve establishing the status of ATR (e.g using PCR sequence analysis) in cells derived from patients with diseases that may be connected with damage to replicating cells, e.g. familial predisposition to cancer. chromosome breakage or instability phenotype or repair-damage sensitivity phenotype.

The probes of the invention may conveniently be packaged in the form of a test kit in a suitable container. In such kits the probe may be bound to a solid support where the assay format for which the kit is designed requires such binding. The kit may also contain suitable reagents for treating the sample to be probed, hybridizing the probe to nucleic acid in the sample, control reagents, instructions, and the like.

The present invention also provides polynucleotides encoding the polypeptides of the invention described below. Because such polynucleotides will be useful as sequences for recombinant production of polypeptides of the invention, it is not necessary for them to be selectively hybridizable to the sequence Seq. ID No. 1, although this will generally be desirable. Otherwise, such polynucleotides may be labelled, used, and made as described above if desired. Polypeptides of the invention are described below.

Particularly preferred polynucleotides of the invention are hose derived from the lipid kinase domain of ATR, its allelic variants and species homologues. The lipid kinase domain is represented by nucleotides 7054 to 8011 of Seq. ID. 1. Polynucleotides of the invention which comprise this domain are particularly preferred. The "lipid kinase domain" refers to a domain which has homology to other known lipid kinases, in particular the p110 subunit of PI-3 kinase, as determined by sequence alignments.

Other preferred polynucleotides of the invention those which comprise nucleotides encoding amino acids 181 to 302 of Seq. ID No. 2 (nucleotides 620 to 985 of Seq. ID No. 1), which is believed to be a leucine zipper region, a putative site of protein-protein interaction, and amino acids 1358 to 1366 (nucleotides 4151 to 4177), which is also conserved. In an additional aspect, polynucleotides of the invention include those of Seq. ID No. 3 and fragments thereof capable of selectively hybridizing to this sequence other than the fragment consisting of nucleotides 2482 to 6599 in which the following changes have been made: Deletion of residues 2499, 2501, 2507 & 2509; insertion of C between 5918/5919.

Particularly preferred fragments include those comprising residues 6826 to 7334 (the lipid kinase domain) and the leucine zipper regions 1476 to 1625 and 2310 to 2357.

Additionally, the fragment comprising the conserved region 3891 to 3917 is preferred. Such polypeptides and fragments may be made and used as described above.

B. Polypeptides

Polypeptides of the invention include polypeptides in substantially isolated form which comprise the sequence set out in Seq ID No. 2.

Polypeptides further include van of such sequences, including naturally occurring allelic variants and synthetic variants which are substantially homologous to said polypeptides. In this context, substantial homology is regarded as a sequence which has at least 70%, e.g. 80% or 90% amino acid homology (identity) over 30 amino acids with the sequence of Seq. ID No. 2 except for the lipid kinase domain and C-terminal portion (residues 2326 to 2644) where substantial homology is regarded as at least 80% homology, preferably 90% homology (identity) over 50 amino acids.

Polypeptides also include other those encoding ATR homologues from other species including animals such as mammals (e.g. mice, rats or rabbits), especially primates, and variants thereof as defined above.

Polypeptides of the invention also include fragments of the above mentioned full length polypeptides and variants thereof, including fragments of the sequence set out in Seq. ID No. 2.

Preferred fragments include those which include an epitope, especially an epitope. Suitable fragments will be at least about 5, e.g. 10, 12, 15 or 20 amino acids in size. Polypeptide fragments of the ATR protein and allelic and species variants thereof may contain one or more (e.g. 2, 3, 5, or 10) substitutions, deletions or insertions, including conserved substitutions.

Conserved substitutions may be made according to the following table indicates conservative substitutions, where amino acids on the same block in the second column and preferably in the same line in the third column may be substituted for each other:

| ALIPHATIC | Non-polar | G A P |
| | | I L V |
| | Polar - uncharged | C S T M |
| | | N Q |
| | Polar - charged | D E |
| | | K R |
| AROMATIC | | H F W Y |
| OTHER | | N Q D E |

Variants of the polypeptides of the invention may also comprise polypeptides wherein one or more of the specified (i.e., naturally encoded) amino acids is deleted or replaced or wherein one or more nonspecified ammo acids arc added: (1) without loss of the kinase activity specific to the polypeptides of the invention; or (2) with disablement of the kinase activity specific to the polypeptides of the invention; or (3) with disablement of the ability to intend with members or regulators of the cell cycle checkpoint pathway.

Epitopes may be determined either by techniques such as peptide scanning techniques as described by Geysen et al. Mol. Immunol., 23; 709–715 (1986).

Polypeptides of the invention may be in a substantially isolated form. It will be understood that the polypeptide may be mixed with carriers or diluents which will not interfere with the intended purpose of the polypeptide and still be regarded as substantially isolated. A polypeptide of the invention may also be in a substantially purified form, in which case it will generally comprise the polypeptide in a preparation in which more than 90%, e.g. 95%, 98% or 99% of the polypeptide in the preparation is a polypeptide of the invention. Polypeptides of the invention may be modified for example by the addition of Histidine residues to assist their purification or by the addition of a signal sequence to promote their secretion from a cell.

A polypeptide of the invention may be labelled with a revealing label. The revealing label may be any suitable label which allows the polypeptide to be detected. Suitable labels include radioisotopes, e.g. $^{125}$I, enzymes, antibodies, polynucleotides and linkers such as biotin. Labelled polypeptides of the invention may be used in diagnostic procedures such as immunoassays in order to determine the amount of a polypeptide of the invention in a sample. Polypeptides or labelled polypeptides of the invention may also be used in serological or cell mediated immune assays for the detection of immune reactivity to said polypeptides in animals and humans using standard protocols.

A polypeptide or labelled polypeptide of the invention or fragment thereof may also be fixed to a solid phase, for example the surface of an immunoassay well or dipstick.

Such labelled and/or immobilized polypeptides may be paged into kits in a suitable container along with suitable reagents, controls, instructions and the like.

Such polypeptides and kits may be used in methods of detection of antibodies to the ATR protein or its allelic or species variants by immunoassay.

Immunoassay methods are well known in the an and will generally comprise:
  (a) providing a polypeptide comprising an epitope bindable by an antibody against said protein;
  (b) incubating a biological sample with said polypeptide under conditions which allow for the formation of an antibody-antigen complex; and
  (c) determining whether antibody-antigen complex comprising said polypeptide is formed.

Polypeptides of the invention may be may by synthetic means (e.g. as described by Geysen et al.) or recombinantly, as described below.

Particularly preferred polypeptides of the invention include those spanning or within the lipid kinase domain, namely from amino acids 2326 to 2644 of Seq. ID. 2. or sequences substantially homologous thereto. Fragments as defined above from this region are particularly preferred. The polypeptides and fragments thereof may contain amino acid alterations as defined above, including substitutions at one or more of positions 2475, 2480 and 2494, which correspond to the positions of the rad3 substitutions described in the examples below. Preferred substiutions include D2475A, N2480K and D2494E.

Polypeptides of the invention may be used in in vitro or in vivo cell culture systems to study the role of ATR as a checkpoint gene. For example, truncated or modified (e.g. modified in the lipid kinase domain) ATRs may be introduced into a cell to disrupt the normal checkpoint functions which occur in the cell.

The polypeptides of the invention may be introduced into the cell by in situ expression of the polypeptide from a recombinant expression vector (see below). The expression vector optionally carries an inducible promoter to control the expression of the polypeptide.

The use of mammalian host cells is expected to provide for such post-translational modifications (e.g., myristolation, glycosylation, truncation, lapidation and tyrosine, serine or threonine phosphorylation) as may be needed to confer optimal biological activity on recombinant expression products of the invention.

Such cell culture systems in which polypeptide of the invention are expressed may be used in assay systems to identify candidate substances which interfere or enhance checkpoint functions in the cell (see below).

In an additional aspect, polypeptides of the invention include the protein of Seq. ID No. 4 and fragments thereof from the region other than the fragment consisting of amino acids 713 to 1778. Particularly preferred fragments include those comprising residues 2082 to 2386 (the lipid kinase domain) and the leucine zipper regions 298 to 347 and 576 to 591. Additionally, the fragment comprising the conserved region 1103 to 1111 is preferred. Such polypeptides and fragments may be made and used as described above.

The invention also provides polypeptides substantially homologous to the protein of Seq. ID No. 4, and fragments thereof. In this context, substantial homology is regarded as a sequence which has at least 70%, e.g. 80% or 90% amino acid homology (identity) over 30 amino acids with the sequence of Seq. ID No. 4 except for the lipid kinase domain and C-terminal portion (residues 2082 to 2386) where substantial homology is regarded as at least 80%, preferably at least 90% homology (identity) over 50 amino acids.

C. Vectors

Polynucleotides of the invention can be incorporated into a recombinant replicable vector. The vector may be used to replicate the nucleic acid in a compatible host cell. Thus in a further embodiment, the invention provides a method of making polynucleotide of the invention by introducing a polynucleotide of the invention into a replicable vector, introducing the vector into a compatible host cell, and growing the host cell under conditions which bring about replication of the vector. The vector may be recovered from the host cell. Suitable host cells are described below in connection with expression vectors.

D. Expression Vectors

Preferably, a polynucleotide of the invention in a vector is operably linked to a control sequence which is capable of providing for the expression of the coding sequence by the host cell, i.e. the vector is an expression vector.

The term "operably linked" refers to a juxtaposition wherein the components described are in a relationship permitting them to function in their intended manner. A control sequence "operably linked" to a coding sequence is ligated in such a way that expression of the coding sequence is achieved under condition compatible with the control sequences.

Such vectors may be transformed into a suitable host cell as described above to provide for expression of a polypeptide of the invention. Thus, in a further aspect the invention provides a process for preparing polypeptides according to the invention which comprises cultivating a host cell transformed or transfected with an expression vector as described above under conditions to provide for expression by the vector of a coding sequence encoding the polypeptides, and recovering the expressed polypeptides.

The vectors may be for example, plasmid, virus or phage vectors provided with an origin of replication, optionally a promoter for the expression of the said polynucleotide and optionally a regulator of the promoter. The vectors may contain one or more selectable marker genes, for example an ampicillin resistance gene in the case of a bacterial plasmid or a neomycin resistance gene for a mammalian vector. Vectors may be used in vitro, for example for the production of RNA or used to transfect or transform a host cell. The vector may also be adapted to be used in vivo, for example in a method of gene therapy.

A further embodiment of the invention provides host cells transformed or transfected with the vectors for the replication and expression of polynucleotides of the invention. The cells will be chosen to be compatible with the said vector and may for example be bacterial, yeast, insect or mammalian.

Polynucleotides according to the invention may also be inserted into the vectors described above in an antisense orientation in order to provide for the production of antisense RNA. Antisense RNA or other antisense polynucleotides may also be produced by synthetic means. Such antisense polynucleotides may be used in a method of controlling the levels of ATR or its variants or species homologues.

Promoters and other expression regulation signals may be selected to be compatible with the host cell for which the expression vector is designed. For example, yeast promoters include S. cerevisiae GAL4 and ADH promoters, S. pombe nmt1 and adh promoter. Mammalian promoters include the metallothionein promoter which is can be included in response to heavy metals such as cadmium. Viral promoters such as the SV40 large T antigen promoter or adenovirus promoters may also be used. All these promoters are readily available in the art.

E. Antibodies

The invention also provides monoclonal or polyclonal antibodies to polypeptides of the invention or fragments thereof. The invention further provides a process for the production of monoclonal or polyclonal antibodies to polypeptides of the invention. Monoclonal antibodies may be prepared by conventional hybridoma technology using the polypeptides of the invention or peptide fragments thereof, as immunogens. Polyclonal antibodies may also be prepared by conventional means which comprise inoculating a host animal, for example a rat or a rabbit, with a polypeptide of the invention or peptide fragment thereof and recovering immune serum.

In order that such antibodies may be made, the invention also provides polypeptides of the invention or fragments thereof haptenised to another polypeptide for use as immunogens in animals or humans Preferred antibodies of the invention will be capable of selectively binding the human ATR protein, that is with an affinity at least 10 fold, preferably at least 100 fold that of the rad3 protein. Such antibodies can be obtained by routine experimentation, e.g. selecting regions of ATR protein with sequences different from the corresponding regions of rad3, making peptides comprising such sequences and using such peptides as immunogens. Following production of antibodies the binding of said antibodies may be determined. Preferred antibodies of the invention include those capable of selectively binding the lipid kinase domain (as defined above) of the human ATR protein. In addition, antibodies which are capable of binding the human and yeast (S. pombe) lipid kinase domains with similar affinity, but not to the domains of the ATM family of proteins form a further aspect of the invention. Such antibodies may be raised against peptides from the lipid se domains which correspond to regions found to be identical, or substantially identical, in the yeast and human genes.

For the purposes of this invention, the term "antibody", unless specified to the contrary, includes fragments of whole antibodies which retain their binding activity for a tumour target antigen. Such fragments include Fv, F(ab') and F(ab')$_2$ fragments, as well as single chain antibodies. Furthermore, the antibodies and fragments thereof may be humanised antibodies, eg. as described in EP-A-239400.

Antibodies may be used in method of detecting polypeptides of the invention present in biological samples by a method which comprises:

(a) providing an antibody of the invention;

(b) incubating a biological sample with said antibody under conditions which allow for the formation of an antibody-antigen complex; and (c) determining whether antibody-antigen complex comprising said antibody is formed.

Suitable samples include extracts from dividing cells, e.g leukocytes or cancer cells including leukaemic cells and solid tumours such as breast, ovary, lung, colon, pancreas, testes, liver, brain, muscle and bone tumours.

Antibodies of the invention may be bound to a solid support and/or packaged into kits in a suitable container along with suitable reagents, controls, instructions and die like.

F. Assays

Abrogating cell cycle checkpoints is a potential strategy for developing or designing drugs for anti cancer therapy, both as a novel treatment as such and as part of a combination therapy to enhance the specific toxicity of current chemotherapeutic agents. For example alkylating agents such as nitrogen mustards are used a chemotherapeutic agents which damage DNA in rapidly dividing cells, leading to cell death. The toxicity of such agents may be lessened by DNA repair and checkpoint mechanisms. Abrogating such mechanisms will thus enhance the effectiveness of therapeutic compounds designed to damage DNA. Abrogation of the ATR checkpoint will be especially useful where tumour cells have lost other checkpoint or damage response genes, since these other genes may be able to complement the loss of ATR function in non tumour cells, leading to an even greater enhancement in the effectiveness of the chemotherapeutic agent.

The lipid kinase activity of ATR is a target for developing anticancer compounds, since the results presented in the following examples indicate that the kinase domain is required for ATR function. Thus the present invention provides an assay method for screening candidate substances for anti-cancer therapy which comprises:

(a) providing a polypeptide of the invention which retains lipid kinase activity and a substrate for said kinase, under conditions and with reagents such that the kinase activity will act upon the substrate;

(b) bringing said polypeptide and substrate into contact with a candidate substance;

(c) measuring the degree of decrease in the kinase activity of the polypeptide; and (d) selecting a candidate substance which provides a decrease in activity.

The assay may be carried out in vitro, for example in the wells of a microtitre dish. Such a format may be readily adapted for automation, allowing large numbers of candidate substances to be screened.

The substrate may be a protein or lipid substrate of natural or synthetic origin upon which the polypeptide of the invention will act. Usually, the polypeptide of the invention will phosphorylate the substrate.

Any suitable format for the assay may be used by those of skill in the art of throughput assays. Typically, the polypeptide of the invention which retains lipid kinase activity will be bound to a solid support in the presence of a substrate and cellular and other components which are usually required for activity. Labelled phosphate and a candidate substance will be added to the mixture simultaneously or sequentially in either order. After a suitable reaction time (usually a few minutes but in any event enough for phosphorylation of the substrate in the absence of candidate substance to occur) the amount of free phosphate is determined, e.g. by precipitation of phosphate. Candidate substances which inhibit kinase activity will inhibit the incorporation of free phosphate into the substrate and thus where free phosphate is found this is indicative of inhibition.

Other assay formats may be used by those skilled in the art.

The candidate substances may be used in an initial screen in batches of for example 10 compounds per reaction, and the compounds of those batches which show inhibition tested individually.

Suitable candidate substances include peptides, especially of from about 5 to 20 amino acids in size, based on the sequence of the kinase domain, or variants of such peptides in which one or more residues have been substituted as described above. Peptides from panels of peptides comprising random sequences or sequences which have been varied consistently to provide a maximally diverse panel of peptides may be used. Further candidate substances include kinase inhibitors which are small molecules such as cyclosporin-like and staurosporin-like compounds, or other compounds commercially available in panels of small molecule inhibitors.

Candidate substances which show activity in in vitro screens such as the above can then be tested in in vivo systems, such as yeast or mammalian cells which will be exposed to the inhibitor and tested for checkpoint activity.

We have also shown that Rad3 possesses protein kinase activity. Target substrates of Rad3 protein kinase activity may be identified by incorporating test compounds in assays for kinase activity. Rad3 protein is resuspended in kinase buffer and incubated either in the presence of absence of the test compound (e.g., casein, histone H1, or appropriate substrate peptide). Moles of phosphate transferred by the kinase to the test compound are measured by autoradiography or scintillation courting. Transfer of phosphate to the test compound is indicative that the test compound is a substrate of the kinase.

Agents that modulate Rad3/ATR lipid kinase or Rad 3 protein kinase activity may be identified by incubating a test compound and Rad3/ATR immunopurified from cells naturally expressing Rad3/ATR, with Rad3/ATR obtained from recombinant procaryotic or eukaryotic cells expressing the enzyme, or with purified Rad3/ATR, and then determining the effect of the test compound on Rad3/ATR activity. The activity of the Rad3/ATR lipid kinase or Rad3 protein kinase domains can be measured by determining the moles of $^{32}$P-phosphate transferred by the kinase from gamma-$^{32}$-P-ATP to either itself (autophosphorylation) or to an exogenous substrate such as a lipid or protein. The amount of phosphate incorporated into the substrate is measured by scintillation counting or autoradiography. An increase in the moles of phosphate transferred to the substrate in the presence of the test compound compared to the moles of phosphate transferred to the substrate in the absence of the test compound indicates that the test compound is an activator of said kinase activity. Conversely, a decrease in the moles of phosphate transferred to the substrate in presence of the test compound compared to the moles of phosphate transferred to the substrate in the absence of the test compound indicates that the modulator is an inhibitor of said kinase activity.

In a presently preferred assay, a Rad3/ATR antibody linked to agarose beads is incubated with a cell lysate prepared from host cells expressing Rad3/ATR. The beads are washed to remove proteins binding nonspecifically to the beads and the beads are then resuspended in a kinase buffer (such as 25 mM K-HEPES pH 7.7, 50 mM potassium chloride, 10 mM magnesium chloride. 0.1% Nonidet-P40, 20% glycerol, 1 mM DTT). The reaction is initiated by the addition of 100 μM gamma-$^{32}$P-ATP (4 Ci/mM) and an exogenous substrate such as lipid or peptide, and the reaction is carried out at 30° C. for 10 minutes. The activity of the kinase is measured by determining the moles of $^{32}$P-phosphate transferred either to the kinase itself or the added substrate. In a preferred embodiment the host cells lack endogenous Rad3/ATR kinase activity. The selectivity of a compound that modulates the lipid kinase activity of Rad3/ATR can be evaluated by comparing its activity on Rad3/ATR to its activity on, for example, other known phosphatidylinositol-3 (PI-3)related kinases. The combination of the recombinant Rad3/ATR products of the invention with other recombinant PI-3-related kinase products in a series of independent assays provides a system for developing selective modulators of Rad3/ATR kinase activity. Similarly, the selectivity of a compound that modulates the protein kinase activity of Rad3 may be determined with reference to other protein kinases, for example the DNA dependent protein kinase or ATM.

In addition, the demonstration that the rad mutant rad.D2249E (see Examples) can act as a dominant negative mutant indicates involvement in one or more protein complexes, and such complexes themselves can be targeted for therapeutic interventions We have shown, for example, that Rad3 can both self associate and associate with ATR. It is therefore likely that Rad/ATR function as multimeric molecules Mutant yeast rad or human ATR genes, or derivatives thereof which also lack rad/ATR activity may be introduced into cells to act as dominant negative mutants. Thus for example if expression of a dominant negative mutant (e.g. ATR D2475A, N2480K or D2494E) in a tumour cell leads to enhanced radiation sensitivity this indicates that the native ATR is still functioning and thus a target for therapeutic agents.

Interacting proteins including components of multimeric protein complexes involving Rad3 or ATR may be identified by the following assays.

A first assay contemplated by the invention is a two-hybrid screen. The two-hybrid system was developed in yeast (Chien et al. (1991)) and is based on functional in vivo reconstitution of a transcription factor which activates a reporter gene. Specifically, a polynucleotide encoding a protein that interacts with Rad3/ATR is isolated by: transforming or transfecting appropriate host cells with a DNA construct comprising a reporter gene under the control of a promoter regulated by a transcription factor having DNA a binding domain and an activating domain: expressing in the host cells a first hybrid DNA sequence encoding a fire fusion of part or all of Rad3/ATR and either the DNA binding domain or the activating domain of the transcription factor; expressing in the host cell a library of second hybrid DNA sequences encoding second fusion of part or all putative Rad3/ATR binding proteins and the DNA binding domain or activating domain of the transcription factor which is not incorporated in the first fusion; detecting binding of an Rad3/ATR interacting protein to Rad3/ATR in a particular host cell by detecting the production of reporter gene product in the host cell; and isolating second hybrid DNA sequences encoding the interacting protein from the particular host cell. Presently preferred for use in the assay are a lexA promoter to drive expression of the reporter gene, the reporter gene, a transcription factor comprising the lexA DNA binding domain and the GAL4 transactivation domain, and yeast host cells.

Other assays for identifying proteins that interact with Rad3 or ATR may involve immobilising Rad3/ATR or a test protein, detectably labelling the nonimmobilised binding partner, incubating the binding partners together and determining the amount of label bound. Bound label indicates that the test protein interacts with Rad3/ATR.

Another type of assay for identifying Rad3 or ATR interacting proteins involves immobilising Rad3/ATR or a fragment thereof on a solid support coated (or impregnated with) a fluorescent agent, labelling a test protein with a compound capable of exciting the fluorescent agent, contacting the immobilised Rad3/ATR with the labelled test protein, detecting light emission by the fluorescent agent, and identifying interacting proteins as test proteins which result in the emission of light by the fluorescent agent. Alternatively, the putative interacting protein may be immobilised and Rad3/ATR may be labelled in the assay.

Compounds that modulate interaction between Rad3/ATR and other cellular components may be used in methods of treating cancer. For example, if a particular form of cancer results from a mutation in a gene other than ATR such as the p53 gene, an agent which inhibits the transcription or the enzymatic activity of ATR and thus the $G_2$ cell cycle checkpoint may be used to render cancerous cells more susceptible to chemotherapy or radiation therapy. The therapeutic value of such an agent lies in the fact that current radiation therapy or chemotherapy in most cases does nothing to overcome the ability of the p53 mutant cancerous cell to sense and correct the DNA damage imposed as a result of the treatment. As a result, a cancer cell can simply repair the DNA damage. Modulating agents of the invention may therefore be chemotherapy and radiation adjuvants or may be directly active as chemotherapy drugs themselves.

Assays for identifying compounds that modulate interaction of Rad3/ATR with other proteins may involve: transforming or transfecting appropriate host cells with a DNA construct comprising a reporter gene under the control of a promoter regulated by a transcription factor having a DNA-binding domain and an activating domain: expressing in the host cells a first hybrid DNA sequence encoding a first fusion of part or all of Rad3/ATR and the DNA binding domain or the activating domain of the transcription factor; expressing in the host cells a second hybrid DNA sequence encoding part or all of a protein that interacts with Rad3/ATR and the DNA binding domain or activating domain of the transcription factor which is not incorporated in the first fusion; evaluating the effect of a test compound on the interaction between Rad3/ATR and the interacting protein by detecting binding of the interacting protein to Rad3/ATR in a particular host cell by measuring the production of reporter gene product in the host cell in the presence or absence of the test compound; and identifying modulating compounds as those test compounds altering production of the reported gene product in comparison to production of the reporter gene product in the absence of the modulating compound. Presently preferred for use in the assay are a lexA promoter to drive expression of the reporter gene, the lacZ reporter gene, a transcription factor comprising the lexA DNA domain and the GALA transactivation domain, and yeast host cells.

Another type of assay for identifying compounds that modulate the interaction between Rad3/ATR and an interacting protein involves immobilising Rad3/ATR or a natural Rad3/ATR interacting protein, detectably labelling the non-immobilised binding partner, incubating the binding partners together and determining the effect of a test compound on the amount of label bound wherein a reduction in the label bound in the present of the test compound compared to the amount of label bound in the absence of the test compound indicates that the test agent is an inhibitor of Rad3/ATR interaction with the protein. Conversely, an increase in the bound in the presence of the test compared to the amount label bound in the absence of the compared indicates that the putative modulator is an activator of Rad3/ATR interaction with the protein.

Yet another method contemplated by the invention for identifying compounds that modulate the binding between Rad3/ATR and an interacting protein involves immobilising Rad3/ATR or a fragment thereof on a solid support coated (or impregnated with) a fluorescent agent, labelling the interacting protein with a compound capable of exciting the fluorescent agent, contacting the immobilised Rad3/ATR with the labelled interacting protein in the presence and absence of a test compound, detecting light emission by the fluorescent agent, and identifying modulating compounds as those test compounds that affect the emission of light by the fluorescent agent in comparison to the emission of light by the fluorescent agent in the absence of the test compound. Alternatively, the Rad3/ATR interacting protein may be immobilised and Rad3/ATR may be labelled in the assay.

We have shown that Rad3 interacts with ATR. Therefore the above-mentioned assays may also be used to identify compounds that modulate the interaction between Rad3 and ATR where the interacting protein described in the assay methods is either Rad3 or ATR.

We have also shown that Rad3 can bind to itself, strongly suggesting that ATR can also bind to itself. Therefore the above-mentioned assays may also be used to identify compounds that modulate Rad3-Rad3 interactions and ATR-ATR interactions.

Such compounds could be used therapeutically to disrupt ATR-ATR interactions and increase the sensitivity of tumour cells to chemotherapy and/or radiotherapy. Thus the invention provides an assay method for screening candidate substances for anti cancer therapy which comprises:

(a) (i) incubating a polypeptide of the invention with another polypeptide of the invention, which may be the same as or different to the first polypeptide, under conditions which allow the first polypeptide to bind to the second polypeptide to form a complex;

(ii) bringing the complex thus formed into contact with a candidate substance;

or (a) incubating a polypeptide of the invention with another polypeptide of the invention, which may be the same as or different to the first polypeptide, under conditions which allow the first polypeptide to bind to the second polypeptide to form a complex and in the presence of a candidate substance;

and (b) determining whether the candidate substance inhibits binding of the first polypeptide to the second polypeptide and (c) selecting a candidate substance which inhibits binding of the first polypeptide to the second polypeptide.

Preferably the first and second polypeptide may be distinguished from each other. For example, the first polypeptide and the second polypeptide may both be ATR, or may both be Rad3, or one may be ATR and one may be Rad3 or derivatives of either ATR or Rad3 which retain binding activity. When both polypeptides are ATR or Rad3, preferably two distinguishable forms of ATR/Rad3 would be used in these assays. They may be distinguished by, for example, labelling either of the polypeptides. Examples of labels include radioactive labels. epitope tags or other polypeptide tags such as glutathione-S-transferase. For example, one form of Rad3 may have one form of epitope tag, and the other form would have a different epitope tag, allowing them to be distinguished immunologically such that binding of one to the other can be ascertained quantitively or qualitatively. In a preferred method, the first polypeptide may be immobilised, for example to agarose beads or a solid support, and the second polypeptide may be in free solution. Binding is then determined using methods described above and well-known to skilled persons.

Also comprehended by the present invention are antibody products (e.g., monoclonal and polyclonal antibodies, single chain antibodies, chimeric antibodies, CDR-grafted antibodies and the like) and other binding proteins (such as those identified in the assays above) which are specific for the Rad3 protein kinase domain or the Rad3/ATR lipid kinase domains. Binding proteins can be developed using isolated natural or recombinant enzymes. The binding proteins are useful, in turn, for purifying recombinant and naturally occurring enzymes and identifying cells producing such enzymes. Assays for the detection and quantification of proteins in cells and in fluids may involve a single antibody substance or multiple antibody substances in a "sandwich" assay format. The binding proteins are also manifestly useful in modulating (i.e., blocking, inhibiting, or stimulating) enzyme/substrate or enzyme/regulator interactions.

Modulators of Rad3/ATR may affect its kinase activity, its localisation in the cell, and/or its interaction with members of the cell cycle checkpoint pathway. Selective modulators may include, for example, polypeptides or peptides which specifically bind to Rad3/ATR or Rad3/ATR nucleic acid, and/or other non-peptide compounds (e.g., isolated or synthetic organic molecules) which specifically react with Rad3/ATR or Rad3/ATR nucleic acid. Mutant forms of Rad3/ATR which affect the enzymatic activity or cellular localisation of wild-type Rad3/ATR are also contemplated by the invention.

Furthermore, combinatorial libraries, peptide and peptide mimetics, defined chemical entities, oligonucleotides, and natural product libraries may be screened for activity as modulators of Rad3/ATR kinase activity and RAd3/ATR interactions in assays such as those described F. Therapeutic Uses Modulators of Rad3/ATR activity, including inhibitors of their lipid kinase and protein kinase activities, may be used in anti-cancer therapy. In particular, they may be used to increase the susceptibility of cancer cells to chemotherapy and/or radiotherapy by virtue of their ability to disrupt the cell cycle regulatory functions of Rad3/ATR.

Thus the invention provides the use of compounds that modulate Rad3/ATR activity, identified by the screening assays described above, in a method of treatment of cancer. In one embodiment, said compounds are capable of inhibiting rad3/ATR lipid kinase and/or Rad3 protein kinase activity. In another embodiment, said compounds are capable of inhibiting interactions between ATR and itself and/or between ATR and other interacting proteins which may, for example, normally form part of a multimeric protein complex.

It is to be understood that the term "compound" in this context also refers 10 the candidate substances selected in the above-described assays.

Typically the compounds are formulated for clinical administration by mixing them with a pharmaceutically acceptable carrier or diluent. For example they can be formulated for topical, parenteral, intravenous, intramuscular, subcutaneous, intraocular or transdermal administration. Preferably, the compound is used in an injectable form. Direct injection into the patient's tumour is advantageous because it makes it possible to concentrate the therapeutic effect at the level of the affected tissues. It may therefore be so with any vehicle which is pharmaceutically acceptable for an injectable formulation, preferably for a direct injection at the site to be treated. The pharmaceutically carrier or diluent may be, for example, sterile or isotonic solutions.

The dose of compound used may be adjusted according to various parameters, especially according to the compound used, the age, weight and condition of the patient to be treated, the mode of administration used, pathology of the tumour and the required clinical regimen. As a guide, the amount of compound administered by injection is suitably from 0.01 mg/kg to 30 mg/kg, preferably from 0.1 mg/kg to 10 mg/kg.

The routes of administration and dosages described are intended only as a guide since a skilled practitioner will be able to determine readily the optimum route of administration and dosage for any particular patient and condition.

Compounds to be administered may include polypeptides or nucleic acids. The nucleic acids may encode polypeptides or they may encode antisense constructs that inhibit expression of a cellular gene. Nucleic acids may be administered by, for example, lipofection or by viral vectors. For example, the nucleic acid may form part of a viral vector such as an adenovirus. When viral vectors are used, in general the dose administered is between $10^4$ and $10^{14}$ pfu/ml, preferably $10^6$ to $10^{10}$ pfu/ml. The term pfu ("plaque forming unit") corresponds to the infectivity of a virus solution and is determined by infecting an appropriate cell culture and measuring, generally after 48 hours, the number of plaques of infected cells. The techniques for determining the pfu titre of a viral solution are well documented in the literature.

Any cancer types may be treated by these methods, for example leukaemias, and solid tumours such as breat, ovary, lung, colon, pancreas, testes, liver, brain, muscle and bone tumour. Preferably, the tumour has normal ATR function.

DESCRIPTION OF THE DRAWINGS

FIG. 1

The relationship between ATR, rad3, mei-41, MEC1, TEL1 and ATM

A. Overall structures of ATR, Rad3, Mei-41, Mec1p, Tel1p and ATM.

Legend: open square—Rad3 domain; hatched boxes—kinase domain

B. Dendrogram based on sequence alignments generated by the Clustal method (PAM250) using DNAstar software, rad3/ESR1/mei-41/ATR are more closely related to each other than to ATM and TEL1. Sequences of rad3 and ATM are available in the EMBL database.

The following examples illustrate the invention.

EXAMPLE 1

The rad3 gene of *S. pombe* is one of six genes absolutely required for the DNA structure checkpoints in *S. pombe* (Al-Khodairy and Carr, 1992; Al-Khodairy et a. 1994). A sequence refining part of the rad3 gene was reported by Seaton et al. (1992). In attempting to clarify the intron/exon structure of this gene we identified sequencing anomalies at both the 5' and 3' ends. We have sequenced the complete gene (see Experimental Procedures) and find that rad3 is capable of encoding a product of 2386 amino acids. The C-terminal region contains the consensus sequences typical of a sub-class of kinases known as lipid kinases, the founder member of which is the p110 catalytic subunit of PI3 kinase (Hiles et al. 1992).

A truncated rad3 clone lacking the amino terminus and the kinase region has been reported to complement the rad3::pR3H1.0 gene disruption mutant of rad3 (Jimenez et al. 1992). This disruption mutant does not remove the potential kinase domain. To clarify the role of this domain, we have created a null mutant by gene replacement. This mutant has amino acids 1477–2271 of rad3, including the kinase consensus domain, replaced by ura4$^+$. This strain rad3.d, has identical checkpoint defects and radiation/hydroxyurea sensitivities to the rad3.136 mutant (Nasim and Smith. 1975) and the original rad3::pR3H1.0 disruption mutant (Jimenez et at. 1992: Seaton et al. 1992) (data not shown). We have created three separate point mutants in the putative kinase domain of rad3 and used these in gene replacement experiments to construct strains with defined kinase null mutations. All three stains, rad3.D2230A. rad3.N2235K and rad3.D2249E have phenotypes identical to the rad3.d null mutant da not shown), suggesting that the kinase activity is required for Rad3 function. In the light of our findings, one interpretation of the results of Seaton et al. (1992) and Jimenez et al. (1992) is that the partial clone may show intragenic complementation between the plasmid borne truncated gene and a genomic partial deletion which retains kinase function. Such an interpretation would be consistent with Rad3 acting as a dimer or multimer.

When the kinase Dull allele rad3.D2249E was moderately over-expressed in wild type veils under control of a modified nmt1 promoter (Maundrell, 1990), it caused extreme radiation sensitivity, assayed by UV strip tests, and acted as a dominant negative mutant (data not shown). When the same kinase null construct was expressed at a higher level, it inhibited growth (data not shown). Examination of the cells indicates that division continued very slowly, and at a smaller cell size wild type cells and cells containing empty vector divide at approximately 15 microns, while rad3 and rad3.D2249E over-expressing cells divide at approximately 11.2 microns (data not shown). In S. pombe, this usually indicates an advancement of mitosis.

The Human rad3 Homolog, ATR

To identify a human form of rad3, a combination of methods was applied. Through these approaches, we have cloned the entire coding region of a human gene (see materials and methods). which we have named ATR (ataxia and lad related). ATR is capable of encoding a 2644 amino acid protein which is much more closely related to the products of S. pombe rad3, S. cerevisiae ESR1 (Kato and Ogawa, 1994) and D. melanogaster mei-41 genes (Hari et al. 1995) than to the human ATM and S. cerevisiae Tell proteins (Savitsky et al. 1995; Greenwell et al. 1995) and is likely to be the true homolog of rad3. ESR1 is allelic to the mecI/sad3 checkpoint mutants (Allen et al. 1994; Weinert et al. 1994) which have an equivalent phenotype to rad3. ATR is less closely related to the human checkpoint gene ATM, containing C-terminal putative lipid kinase domain and having a similar overall structure. Sequence alignments demonstrate clearly that the rad3/ESR1(MEC1/SAD3)/mei-41/ATR genes are more closely related to each other than any are to ATR or TEL1, and that ATM is more homologous to TEL1 (FIG. 1).

The ATM gene is expressed in a wide variety of tissues (Savitsky et al. 1995). In S. cerevisiae, ESR1 shows low level expression in mitotic cells but is rapidly in during meiosis 1 (Kato and Ogawa. 1994). Using Northern blot analysis, we have demonstrated that ATR is also weakly expressed in many tissues but that it is mote highly expressed in testis (data not shown). Given that ATP, Rad3 and Esr1p proteins are more highly related to each other than to ATM, the higher ATR expression in testis is consistent with the observation that Esr1p has a role in meiotic recombination (Kato and Ogawa, 1994). Using FISH and PCR analysis, we have mapped ATR to chromosome 3q22–3q25 (data not shown). This region is not associated with known cancer prone syndromes.

In order to further investigate the possibility that Rad3 acts as a multimer, we have created two separate tagged constructs of full length rad3 in pREP based inducible vectors. In one, Rad3 is translated with two myc epitope tags at the N terminus, while in the other these are substituted for a triple HA epitope tag. When both constructs are expressed together in wild type cells, it is possible to co-precipitate the HA tagged Rad3 with the myc specific antibody, and the myc tagged Rad3 with the HA specific antibody (data not shown). This demonstrates that in vivo, the Rad3 protein is capable of self association and is fully consistent with the complementation data of Jimenez et al. (1992).

Although the ATR gene could not complement the phenotype of the rad3 mutants, we have investigated the ability of ATR to form a protein complex with S. pombe Rad3 by expressing both ATR and myc-tagged S. pombe Rad3 in the same yeast cells. Using an anti-ATR antibody (which does not precipitate S. pombe Rad3, see materials and methods) we are able to co-precipitate the yeast protein. We were also able to precipitate the human ATR protein with myc-specific antibodies that recognise the S. pombe Rad3 (data not shown). These data suggest the human and yeast proteins can form a heteromeric-complex, which supports the contention, based on the sequence similarity, of a close functional relationship between these homologues.

Rad3 Proteins have Associated Kinase Activity

Since mutagensis experiments suggest that the kinase activity of the Rad3 proteins in vivo appears to be essential for their function, we have investigated this activity further. Using S. pombe rad3::ura4 cells expressing HA tagged S. pombe Rad3, we have been able to detect a significant protein se activity which precipitates with HA-specific antibodies only when Rad3 is induced and which is not changed following irradiation (data not shown). This activity, which is specific to Rad3 or co-precipitating kinase, appears to reflect phosphorylation of Rad3 itself, since the major band above 200 kD that is phosphorylated can be detected by Western analysis with anti-HA antibody (data not shown). Attempts to identify convenient in vitro substrates such as myelin basic protein. RP-A and several purified S. pombe checkpoint proteins have so far proved unsuccessful. When the IP in vitro kinase assay is performed with cells over-expressing a "kinase-null" D2249E version of Rad3, the associated kinase activity precipitated by HA-specific antibody is significantly reduced (data not shown). There are several possible explanations for this. The measured kinase activity could reflect Rad3 activity directly. In this case the residual activity seen with the kinase dead Rad3 could reflect the fact that it is not unknown for the equivalent D to E mutation in other protein kinases to produce a biologically inert protein with residual in vitro biochemical activity. Alternatively the kinase activity which phosphorylates Rad3 may be due to associated proteins, and these may interact less effectively with the D2249E mutant protein.

Discussion

The checkpoint pathways controlling cell cycle progression following DNA damage or interference in the individual events which comprise the cycle are of considerable importance in maintaining genetic stability and can be considered as pathways which suppress tumorgenesis. Several tumour suppressor genes are intimately involved in subsets of the checkpoint pathways (reviewed in Hartwell and Kastan, 1994), particularly those affecting the transition from G1 into S phase and commitment to the cell cycle. The convergence of the two yeast model systems for checkpoints clearly indicates that the genes involved in these pathways are conserved Our work extends this conservation to metazoan cells, and clarifies the relationship between rad3, ESR1(MEC1/SAD3). mei-41 and the ATM gene.

In this work we demonstrate that the correct sequence of the rad3 gene places its product in the family of protein/lipid kinases related to ATM. Over-expression of kinase-defective rad3 mutant in *S. pombe* causes a dominant negative phenotype, which suggests that Rad3 is acting as a member of a protein complex whose inter is necessary for checkpoint Onion. This is consistent with the observation that rad1, rad9, rad17, rad26 and has1 deletion mutants all have phenotype indistinguishable from rad3.d (Sheldrick and Carr, 1993). Unexpectedly, unlike the remaining checkpoint rad genes, high level over-expression of either wild type or mutant rad alleles inhibits cell growth and causes mitosis to occur at a reduced cell size, indicative of premature entry into mitosis. This "semi wee" phenotype is not observed in the null mutant, and may indicate interference in a second pathway whose function overlaps with that of Rad3 and acts to inhibit mitosis. A candidate for such a pathway is the ATM/TEL1 pathway which has been shown to have some overlapping functions with the ESR1(MEC1/SAD1) pathway (Morrow et al. 1995).

The structure of ATM is most closely related to the Te11p, which is involved in maintaining telomere length (Greenwell et al., 1995). However, ATM function also appears related to that of the Rad3/Esr1p/mei-41 products. Following the initial discovery of the ATM gene and its sequence relationship to the rad3/ESR1 genes and to TEL1, it was not clear whether, as in many cases in yeast, the gene had duplicated and diverged in yeast, or whether the two yeast proteins defined conserved sub-families of closely related genes. The significant finding of this work is the identification of a human gene, ATR, which is more closely related to rad3/ESR1/mei-41. his defines two sully distinct checkpoint related subfamilies of protein/lipid kinases that are conserved throughout eukaryotic evolution. Although the proteins in these two subfamilies may have some overlapping functions, they probably control different processes. For example: the rad3 sub-family in yeast control all the G1 and G2 DNA damage checkpoints in response to both uv and ionising radiation, and the S phase checkpoint which prevents mitosis following inhibition of replication (Al-Khodairy and Carr, 1992: Allen et al., 1994; Weinert et al., 1994). In contrast, A-T cells have abnormal responses to a narrow range of DNA damaging agents including ionising radiation, biomycin and neocarzinostatin, which produce strand breaks in DNA as a consequence of radical attack. The response to uv and most chemical carcinogens is normal, as is the response to the inhibition of DNA synthesis. It is possible that some or all of the remaining DNA damage checkpoints and the S phase checkpoint are controlled by ATR.

Experimental Procedures
Strains, Plasmids and Media

Standard genetic techniques, growth conditions and media for *S. pombe* are described in Gutz et al. (1974). *S. pombe* strain sp011 (ura4.D18, leu.1.32 ade6.704 h⁻) has been described previously (Murray et al. 1992). Plasmid pSUB41 was a gift from S. Subramani (Seaton et al. 1992).

Cloning of *S. pombe* rad3

A 4.0 kb Kpn1 fragment was excised from pSUB41 and sequenced in both directions to obtain the 5' rad3 sequence. The 3' clone was identified from a genomic library (Barbet et al. 1992) by colony hybridisation using a 1 kb 3' probe derived from the published rad3 sequence, and sequenced in both directions. In this way, the sequence of the entire rad3 gene was assembled.

Null and "Kinase Dead" rad3 Mutants

A construct of rad3, in which the 794 amino acids between aa 1477 and aa 2271 (including kinase domain) were replaced with a ura4+ gene, was created using the methodology describerd in Barbet et at. (1992). A linear fragment of this was used to transform sp011 to uracil prototropy and single copy integration at the rad3 locus was checked by Southern blotting. To create the site specific kinase null mutations, a C-terminsl 3.01 kb bamHI-salI fragment of rad3 was mutated with either (A: GTTTTCGC-CATGGCGCGCTCCCAAACCCAA (SEQ ID NO: 5), B: TTCATCAAACAATATCTTTTCGCCATGGCG (SEQ ID NO: 6), or C: CAAAAAGACAGTTGAATTCGACATG-GATAG (SEQ ID NO: 7)) in order to introduce either the D2230A, N2235K or D2249E mutations into the kinase domain. Analgous changes have previously been used in the analysis of P13 kinase vps34 of *S. cerevisiae* (Schu et al. 1993). These fragments were then used to transform the rad3.d null mutant and gene replacements selected by their ability to grow on FOA containing media (Grimm et al. 1988). All strains were checked by Southern blotting. Full length expression constructs of rad3.D2230A were created in pREP1 and pREP41 (Maundrell, 1990) by standard subcloning following introduction of an NdeI site at the ATG and deletion of three internal NdeI sites.

UV Radiation Sensitivity Strip Tests

Expression from REP1 (high) and REP41 (intermediate) was induced by the absence of thiamine for 18 hours prior to plating. Plates were irradiated with a gradient of uv doses down the plate from 0 to 300 Jm$^{-2}$ according to the settings on a Stratagene Stratalinker.

Cloning and Expression of ATR

To isolate an appropriate probe for identifying cDNAs corresponding to a human rad3 homologue, degenerate oligonucleotides were designed against the amino acids LGLGDRH (5' oligo; oDH18)(SEQ ID NO: 13) and HVDF [D/N]C (3' oligo; oDH-16)(SEQ ID NO: 14) or Rad3/Esr1p. Inosine was incorporated at positions of four-fold degeneracy, and primers were tailed with BamHI (oDH18) and EcoRI (oDH16) to facilitate cloning. DNA sequencen analysis of the ~100 bp PCR product obtained from amplification of peripheral blood leukocyte cDNA demonstrated significant similarity to MEC1/rad3. This sequence was used to synthesize a non-degenerate primer (oDH-23; GACGCA-GAATTCACCAGTCAAAGAATCAAAGAG (SEQ ID NO: 8)) for PCR with an additional degenerate primer (oDH17) designed against the amino acid sequence KFPP [I/V][L/F]Y[Q/E]WF (SEQ ID NO: 12) of Rad3/Esr1p. The 174 bp product of this reaction was used directly to screen a macrophage cDNA library. Four positive clones were isolated (the largest approximately 3 kb.

In parallel, database searches with full length *S. pombe* rad3 derived from the EMBL database a human cDNA clone, HSAAADPDG, as a potential homologue of rad3, if a single frameshift was allowed for in the 233 bp sequence. This 233 bp sequence is contained within a 1.6 kb clone obtained from Dr. N. Affara, Human Molecular Genetics Research Group, Cambridge University, UK. The entire clone (1.6 kb) was sequenced and lies within the cDNA clones identified by degenerate PCR and library screens. To identify the whole gene, RACE PCR experiments were performed on cDNA derived from placental and thymus mRNA using the instructions provided with a Clontech Marathon Kit. Gene specific primers were derived from the cDNA clones. From these experiments, a 8239 bp cDNA sequence was assembled with an internal ORF of 2644 amino acids, a 79 bp 5' noncoding region, a 194 bp 3' noncoding region and a poly A⁻ tail. Parts of the sequence were determined solely by PCR. To avoid errors, clones from a minimum of 3 independent PCR reactions were sequenced in both directions.

The 233 bp sequence corresponds to the sequence of nucleotides 6809 to 7042 (234 nt in total) of Seq. ID No. 1 except for a single base deletion at position 6942. This sequence encodes amino acids 2244 to 2320 of Seq. ID No. 2.

The sequence of the "1.6 kb" insert corresponds to nucleotides 5725 to 7104 (1353 nt) of Seq. ID No. 1, and encodes amino acids 1892 to 2340 of Seq. ID No. 2.

Northern blot hybridisation : a 1.3 kb PCR product was amplified in the presence of $_{32}$P-dCTP using primers 279-3 (TGGATGATGA CAGCTGTGTC (SEQ ID NO:9)) and 279-6 (TGTAGTCGCT GCTCAATGTC (SEQ ID NO:10)). A nylon mambrane containing 2 µg of size-fractionated poiy A+ RNA from a variety of human tissue sources (Clontech Laboratories) was probed as recommended by the manufacturer except that the final wash was performed at 55° C. rather than 50° C. to minimize the possibility of cross-hybridization to related sequences.

Mapping ATR

We mapped the ATR gene to chromosome 3 by a combination of fluorescent in situ hybridisation and polymerase chain reaction (PCR) based assays. FISH analysis using a cDNA clone identified the ATR gene on chromosome 3. Two primers (oATR23: GACGCAGAATTCACCAGTCAAA-GAATCAAAGAG (SEQ ID NO: 8) and oATR26: TGGTTTCTGAGAACATTCCCTGA (SEQ ID NO:11)) which amplify a 257 bp fragment of the ATR gene were used on DNA derived from humanlrodent somatic cell hybrids containing various human chromosome panels available from the NIGMS Human Genetic Mutant Cell Repository (Drwinga et al. 1993). PCR with the same primers was used to sub-localise ATR to a specific region on chromosome 3. The templates for these amplifications consisted of DNA samples from patients with truncations along chromosome 3 (Leach et al. 1994).

Immunoprecipitation (IP) and Kinase Assays with Rad3

The *S. pombe* rad3 and human ATR genes were cloned into pREP41 expression vector for complementation studies. To -tag the proteins, versions of these vectors containing in-frame N terminal tag sequences, either a double myc or a triple HA tag, were used (Griffiths et al. 1995). Tagged proteins were expressed by growing in media without thiamine (Maundrell. 1990). Yeast cells lysed in lysis buffer (25 mM Tris.Cl pH 7.5. 60 mM B-glycerophosphate, 0.1 mM Na$_3$VO$_4$, 1% Triton X-100, 50 mM MaCl, 2 mM EDTA. 50 mM NaF, 1 mM phenylmethylsulfonyl fluoride [PMSF], 5 µg/ml leupeptin, 5 µg/ml aprotinin, 1 mM DTT) by the addition of glass beads followed by treatment in a dismembrinator for 2 minutes. For IP's 300 µg total protein extract was incubated on ice with the appropriate antibody for 30 min and the immune complexes precipitated by mixing with Protein G beads for a further 30 min at 4° C. For kinase assays, the immune complexes were washed 4 timed with Lysis buffer, once with Kinase Buffer (25 mM Hepes pH7.7; 50 mM KCl; 10 mM MgCl$_2$; 0.1% NP-40; 2% glycerol; 1 mM DTT), and incubated in Kinase Buffer with 10 µM ATP [50 Ci/mmol]) for 15 minutes at 30° C. The reactions were stopped with 20 ul 2×SDS sample buffer prior to separation on 6% polyacrylamide gels. Rad3 IP's contained several phosphorylated products, including one which comigrated with Rad3 protein itself on Western analysis.

References

Al-Khodairy, F., and. Carr, A. M. (1992). DNA repair mutants defining G2 checkpoint pathways in *Schizosaccharomyces pombe*. EMBO J. 11, 1343–1350.

Al-Khodairy, F., Fotou, E., Sheldrick, K. S., Griffiths, D. J. F., Lehmann A. R. and Carr, A. M. (1994). Identification and characterization of new elements involved in checkpoints and feedback controls in fission yeast. Mol. Biol. Cell 5, 147–160.

Allen, J. B., Zhou, Z., Siede, W., Friedberg, E. C. and Elledge, S. J. (1994) The SAD1/RAD53 protein kinase controls multiple checkpoints and DNA damage-induced transcription in yeast. Genes Dev. 8, 2416–2428.

Barbet, N. C., Muriel, W. J., and Carr, A. M. (1992) Versatile shuttle vectors and genomic libraries for use with *Schizosaccharomyces pombe*, Gene 114, 59–66.

Beamish, H. and Lavin, M. F. (1994) Radiosensitivity in ataxia-telangiectasia: anomalies in radiation-induced cell cycle delay. Int. J. Radiat Biol. 65, 175–184.

Carr, A. M. and Hoekstra, M. F. (1995) The Cellular Responses to DNA Damage. Trends in Cell Biology 5, 32–40.

Chien et al., (1991) Proc. Natl. Acad Sci USA 88, 9578–9582

Deng, C., Zhang, P., Harper, J. W., Elledge, S. J. and Leder, P. J. (1995) Mice lacking p21$^{CIP1/WAF1}$ undergo normal development, but are defective in G1 checkpoint control. Cell, (in press).

Drwinga, H. L., Tojia, L. H., Kim, C. H., Greene, A. E., and Mulovor, R. A. (1993). NIGMS Human/Rodent Somatic Cell Hybrid Mapping Panels 1 and 2. Genomics 16:311–314.

El-Deiry, W. S., Tokino, T., Velculescu, V. E., Levy, D. B., Parson, R., Trent, I. M., Lin D., Mercer, W. E., Kinzler, K. W. and Vogelstein, B. (1993) WAF1, a potential mediator of p53 tumour suppression. Cell 75, 817–825

Enoch, T., Carr, A. M. and Nurse, P. (1992). Fission yeast genes involved in coupling mitosis to completion of DNA-replication. Genes Dev. 6, 2035–2046.

Greenwell, P. W., Kronmal, S. L., Porter, S. E., Gassenhuber, J., Obermaier. B. and Petes, T. D. (1995) TEL1, a gene involved in controlling telomere length in *Saccharomyces cerevisiae*, is homologous to the human ataxia telangiectasia (ATM) gene. Cell submitted.

Grimm C., Kholi, J. Murray, J. M. and Maundrell, K. (1988) Genetic engineering of *Schizosaccharomyces pombe*: a system for gene disruption and replacement using the ura4 gene as a selectable marker. Mol. Gen. Genet. 215, 81–86.

Gutz, H., Heslot, H. Leupold, U. and Loprieno, N. (1974). In "Handbook of Genetics", King R. C., Ed., Plenum Press, New York, Vol. 1, 395–446.

Hari, K. L., Santerre. A., Sekelsky, J. J., McKim, K. S., Boyd, J. B. and Hawley, R. S. (1995) The mei-41 gene of Drosophila melanogaster is functionally homologous to the human ataxia telangiec.

Harper, J. W., Adami, G., Wei, N., Keyomarsi, K. and Elledge, S. J. (1993) The 21 kD Cdk interacting protein Cip1 is a potent inhibitor of G1 cyclin dependent kinases. Cell 75, 805–816.

Hartwell, L. H., and Kastan, M. B. (1994). Cell cycle control and Cancer. Science 266, 1821–1828.

Hiles, I. D., Otsu, M., Volinia, S., Fry, M. J., Gout, I., Dhand, R., Panayotou, G., Ruiz-Larrea, F., Thompson, A., Totty, N. F., Hsuan, J. J., Courtneidge, S. A., Parker, P. J. and Waterfield M. D. (1992) Phosphatidylinositol 3-kinase: structure and expression of the 110 kd catalytic subunit. Cell 70, 419–429.

Jimenez, G., Yucel, J., Rowley, R. and Subramani S. (1992) The rad3+ gene of Schizosaccharomyces pombe is involved in multiple checkpoint functions and in DNA repair. Proc Natl. Acad. Sci. USA 87, 4952–4956

Kato, R. and Ogawa, H. (1994) An essential gene, ESR1, is required for mitotic cell growth, DNA repair and Meiotic recombination in Saccharomyces cerevisiae. Nucleic Acids Res. 22, 3104–3112.

Lamb, J. R., Petit-Frere, C., Broughton, B. C., Lehmann, A. R. and Green, M. H. L. (1989) Inhibition of DNA replication by ionizing radiation is mediated by a trans acting factor. Int. J. Radiat. Biol. 56, 125–130.

Leach, R. J., Chinn, R., Reus, B. E., Hayes, S., Schantz, L., Dubois, B., Overhauser, J., Ballabio, A., Drabkin, H., Lewis, B. T., Mendgen, G., and Naylor, S. L. (1994) Regional Localisation of 188 Sequence Tagged Sites on a Somatic Cell Hybrid Mapping Panel for Human Chromosome 3 Genomics 24, 549–556

Maundrell, K. (1990), nmt1 of fission yeast. A highly transcribed gene completely repressed by thiamine. J. Biol. Chem. 265, 10857–10864.

Morrow. D. M., Tagle, D. A., Shiloh, Y., Collins F. S. and Hieter, P. (1995) HAT1/TEL1, a Saccharomyces cerevisiae homologue of the human gene mutated in ataxia-telangiectasia, is functionally related to the yeast checkpoint gene MEC1/ESR1. Cell submitted.

Murray, J. M., Doe, C. Schenk, P. Carr, A. M. Lehmann, A. R and Watts, F. Z. (1992) Cloning and characterization of the S. pombe rad15 gene, a homologue to the S. cerevisiae RAD3 and human ERCC2 genes Nucleic Acids Res. 20, 2673–2678.

Nasim, A, and Smith, B. P. (1975) Genetic control of radiation sensitivity in Schizosaccharomyces pombe. Genetics 79, 573–582.

Painter, R. B. and Young, B. R (1980) Radiosensitivity in ataxia-telangiectasia: A new explanation. Proc. Natl. Acad. Sci. USA. 77, 7315–7317

Rowley, R., Subramani, S. and Young, P. G. (1992). Checkpoint controls in Schizosaccharomyces pombe, rad1. EMBO J. 11, 1335–1342.

Savitsky, K., Bar-Shira, A., Gilad, S., Rotman, G., Ziv, Y., Vanagaite L., Tagle, D. A., Smith, S., Uziel, T., Sfez, S., Ashkenazi, M., Pecker, I., Frydman, M., Harnik, R., Patanjali, S. R., Simmons, A., Clines, G. A., Sartiel, A., Gatti, R. A., Chessa, L., Sanal, O., Lavine, M. F., Jaspers, N. G. J., Taylor, M. R., Arlett, C. F., Miki, T., Weissman, S. M., Lovett, M., Collins, F. S. and Shiloh, Y. (1995). A single ataxia telangiectasia gene with a product similar to PI-3 kinase. Science 286, 1749–1753.

Seaton, B. L., Yucel, J., Sunnerhagen P. and Subramani, S. (1992). Isolation and characterisation of the Schizosaccharomyces pombe rad3 gene which is involved in the DNA damage and DNA synthesis checkpoints. Gene 119, 83–89.

Schu, P. V., Takegawa, K., Fry, M. J., Stack, J. H., Waterfield, M. D. and Emr, S. D. (1993) Phosphatidylinositol 3-kinase encoded by yeast VPS34 gene essential for protein sorting. Science 260, 88–91.

Sheldrick K. S. and Carr, A. M. (1993). Feedback controls and G2 checkpoints. fission yeast as a model system. BioEssays 15, 775–782.

Walworth, N., Davey, S. and Beach, D. (1993). Fission yeast chk1 protein kinase link the rad checkpoint pathway to cdc2. Nature 363, 368–371.

Weinert, T. A., and Hartwell, L. H. (1988). The RAD9 gene controls the cell cycle response to DNA damage in Saccharomyces cerevisiae. Science 241, 317–322.

Weinert, T. A., Kiser, G. L. Hartwell, L. H. (1994). Mitotic checkpoint genes in budding yeast and the dependence of mitosis on DNA replication and repair. Genes Dev. 8, 652–665.

Sequence Information

```
Sequence ID No, 1: ATR seq
    1 GCGCTCTTCCGGCAGCGGTACGTTTGGAGACGCCGGGAACCCGCGTTGGCGTGGTTGACTACTGCCTCGCAGCCT    75

76 CAGCATGGGGGAACATGGCCTGGAGCTGGCTTCCATGATCCCCGCCCTGCGGGAGCTGGGCAGTGCCACACCAGA   150

151 GGAATATAATACAGTTGTACAGAAGCCAAGACAAATTCTGTGTCAATTCATTGACCGGATACTTACAGATGTAAA   225

226 TGTTGTTGCTGTAGAACTTGTAAAGAAAACTGACTCTCAGCCAACCTCCGTGATGTTGCTTGATTTCATCCAGCA   300

301 TATCATGAAATCCTCCCCACTTATGTTTGTAAATGTGAGTGGAAGCCATGAGCGCAAAGGCAGTTGTATTGAATT   375

376 CAGTAATTGGATCATAACGAGACTTCTGCGGATTGCAGCAACTCCCTCCTGTCATTTGTTACACAAGAAAATCTG   450

451 TGAAGTCATCTGTTCATTATTATTTCTTTTTAAAAGCAAGAGTCCTGCTATTTTTGGGGTACTCACAAAAGAATT   525

525 ATTACAACTTTTTGAAGACTTGGTTTACCTCCATAGAAGAAATGTGATGGGTCATGCTGTGGAATGGCCAGTGGT   600

601 CATGAGCCGATTTTTAAGTCAATTAGATGAACACATGGATATTTACAATCAGCTCCTTTGCAGTTGATGAGTAT   675

676 GCAAAATTTAGAATTTATTGAAGTCACTTTATTAATGGTTCTTACTCGTATTATTGCAATTGTGTTTTTTAGAAG   750

751 GCAAGAACTCTTACTTTGGCAGATAGGTTGTGTTCTGCTAGAGTATGGTAGTCCAAAAATTAAATCCCTAGCAAT   825

826 TAGCTTTTTAACAGAACTTTTTCAGCTTGGAGGACTACCAGCACAACCAGCTAGCACTTTTTTCAGCTCATTTTT   900

901 GGAATTATTAAAACACCTTGTAGAAATGGATACTGACCAATTGAAACTCTATGAAGAGCCATTATCAAAGCTGAT   975
```

-continued

| | Sequence Information | |
|---|---|---|
| 976 | AAAGACACTATTTCCCTTTGAAGCAGAAGCTTATAGAAATATTGAACCTGTCTATTTAAATATGCTGCTGGAAAA | 1050 |
| 1051 | ACTGTCTGTCATGTTTGAAGACGGTGTGCTCATGCGGCTTAAGTCTGATTTGCTAAAAGCAGCTTTGTGCCATTT | 1125 |
| 1126 | ACTGCAGTATTTCCTTAAATTTGTGCCAGCTGGGTATGAATCTGCTTTACAAGTCAGGAAGGTCTATGTGAGAAA | 1200 |
| 1201 | TATTTGTAAAGCTCTTTTGGATGTGCTTGGAATTGAGGTAGATGCAGAGTACTTGTTGGGCCCACTTTATGCAGC | 1275 |
| 1276 | TTTGAAAATGGAAAGTATGGAAATCATTGAGGAGATTCAATGCCAAACTCAACAGGAAAACCTCAGCAGTAATAG | 1350 |
| 1351 | TGATGGAATATCACCCAAAAGGCGTCGTCTCAGCTCGTCTCTAAACCCTTCTAAAAGAGCACCAAAACAGACTGA | 1425 |
| 1426 | GGAAATTAAACATGTGGACATGAACCAAAAGAGCATATTATGGAGTGCACTGAAACAGAAAGCTGAATCCCTTCA | 1500 |
| 1501 | GATTTCCCTTGAATACAGTGGCCTAAAGAATCCTGTTATTGAGATGTTAGAAGGAATTGCTGTTGTCTTACAACT | 1575 |
| 1576 | GACTGCTCTGTGTACTGTTCATTGTTCTCATCAAAACATGAACTGCCGTACTTTCAAGGACTGTCAACATAAATC | 1650 |
| 1651 | GAAGAAGAAACCTTCTGTAGTGATAACTTGGATGTCATTGGATTTTTACACAAAAGTGCTTAAGAGCTGTAGAAG | 1725 |
| 1726 | TTTGTTAGAATCTGTTCAGAAACTGGACCTGGAGGCAACCATTGATAAGGTGGTGAAAATTTATGATGCTTTGAT | 1800 |
| 1801 | TTATATGCAAGTAAAGACTTCATTTGAAGATCATATCCTGGAAGATTTATGTGGTATGCTCTCACTTCCATGGAT | 1875 |
| 1876 | TTATTCCCATTCTGATGATGGCTGTTTAAAGTTGACCACATTTGCCGCTAATCTTCTAACATTAAGCTGTAGGAT | 1950 |
| 1951 | TTCAGATAGCTATTCACCACAGGCACAATCACGATGTGTGTTTCTTCTGACTCTGTTTCCAAGAAGAATATTCCT | 2025 |
| 2026 | TGAGTGGAGAACAGCAGTTTACAACTGGGCCCTGCAGAGCTCCCCTGAAGTAATCCGGGCTAGTTGTGTTAGTGG | 2100 |
| 2101 | ATTTTTTATCTTATTGCAGCAGCAGAATTCTTGTAACAGAGTTCCCAAGATTCTTATAGATAAAGTCAAAGATGA | 2175 |
| 2176 | TTCTGACATTGTCAAGAAAGAATTTGCTTCTATACTTGGTCAACTTGTCTGTACTCTTCACGGCATGTTTTATCT | 2250 |
| 2251 | GACAAGTTGTTTAACAGAACCTTTCTCTGAACACGGACATGTGGACCTCTTCTGTAGGAACTTGAAAGCCACTTC | 2325 |
| 2326 | TCAACATGAATGTTCATCTTCTCAACTAAAAGCTTCTGTCTGCAAGCCATTCCTTTTCCTACTGAAAAAAAAAAT | 2400 |
| 2401 | ACCTAGTCCAGTAAAACTTGCTTTCATAGATAATCTACATCATCTTTGTAAGCATCTTGATTTTAGAGAAGATGA | 2475 |
| 2476 | AACAGATGTAAAAGCAGTTCTTGGAACTTTATTAAATTTAATGGAAGATCCAGACAAAGATGTTAGAGTGGCTTT | 2500 |
| 2551 | TAGTGGAAATATCAAGCACATATTGGAATCCTTGGACTCTGAAGATGGATTTATAAAGGAGCTTTTTGTCTTAAG | 2625 |
| 2626 | AATGAAGGAAGCATATACACATGCCCAAATATCAAGAAATAATGAGCTGAAGGATACCTTGATTCTTACAAGACC | 2700 |
| 2701 | GGATATTGGAAGGGCCGCAAAAGGAGATTTGGTACCATTTGCACTCTTACACTTATTGCATTGTTTGTTATCCAA | 2775 |
| 2776 | GTCAGCATCTGTCTCTGGAGCAGCATACACAGAAATTAGAGCTCTGGTTGCAGCTAAAAGTGTTAAACTGCAAAG | 2850 |
| 2851 | TTTTTTCAGCCAGTATAAGAAACCCATCTGTCAGTTTTTGGTAGAATCCCTTCACTCTAGTCAGATGACAGCACT | 2925 |
| 2926 | TCCGAATACTCCATGCCAGAATGCTGCCGTGCGAAAACAAGATGTGGCTCACCAGAGAGAAATGGCTTTAAATAC | 3000 |
| 3001 | GTTGTCTGAAATTGCCAACGTTTTCGACTTTCCTGATCTTAATCGTTTTCTTACTAGGACATTACAAGTTCTACT | 3075 |
| 3076 | ACCTGATCTTGCTGCCAAAGCAAGCCCTGCAGCTTCTGCTCTCATTCGAACTTTAGGAAAACAATTAAATGTCAA | 3150 |
| 3151 | TCGTAGAGAGATTTTAATAAACAACTTCAAATATATTTTTTCTCATTTGGTCTGTTCTTGTTCCAAAGATGAATT | 3225 |
| 3226 | AGAACGTGCCCTTCATTATCTGAAGAATGAAACAGAAATTGAACTGGGGAGCCTGTTGAGACAAGATTTCCAAGG | 3300 |
| 3301 | ATTGCATAATGAATTATTGCTGCGTATTGGAGAACACTATCAACAGGTTTTTAATGGTTTGTCAATACTTGCCTC | 3375 |
| 3376 | ATTTGCATCCAGTGATGATCCATATCAGGGCCCGAGAGATATCATATCACCTGAACTGATGGCTGATTATTTACA | 3450 |
| 3451 | ACCCAAATTGTTGGGCATTTTGGCTTTTTTTAACATGCAGTTACTGAGCTCTAGTGTTGGCATTGAAGATAAGAA | 3525 |
| 3526 | AATGGCCTTGAACAGTTTGATGTCTTTGATGAAGTTAATGGGACCCAAACATGTCAGTTCTGTGAGGGTGAAGAT | 3600 |
| 3601 | GATGACCACACTGAGAACTGGCCTTCGATTCAAGGATGATTTTCCTGAATTGTGTTGCAGAGCTTGGGACTGCTT | 3675 |
| 3676 | TGTTCGCTGCCTGGATCATGCTTGTCTGGGCTCCCTTCTCAGTCATGTAATAGTAGCTTTGTTACCTCTTATACA | 3750 |
| 3751 | CATCCAGCCTAAAGAAACTGCAGCTATCTTCCACTACCTCATAATTGAAAACAGGGATGCTGTGCAAGATTTTCT | 3825 |
| 3826 | TCATGAAATATATTTTTTACCTGATCATCCAGAATTAAAAAAGATAAAAGCCGTTCTCCAGGAATACAGAAAGGA | 3900 |

-continued

| Sequence Information |
|---|
| 3901 GACCTCTGAGAGCACTGATCTTCAGACAACTCTTCAGCTCTCTATGAAGGCCATTCAACATGAAAATATCGATCT 3975 |
| 3976 TCGTATTCATGCTCTTACAAGCTTGAAGGAAACCTTGTATAAAAATCAGGAAAAACTGATAAAGTATGCAACAGA 4050 |
| 4051 CAGTGAAACAGTAGAACCTATTATCTCACAGTTGGTGACAGTGCTTTTGAAAGGTTGCCAAGATGCAAACTCTCA 4125 |
| 4126 AGCTCGGTTGCTCTGTGGGAATGTTTAGGGGAATTGGGGGCGATAGATCCAGGTCGATTAGATTTCTCAACAAC 4200 |
| 4201 TGAAACTCAAGGAAAAGATTTTACATTTGTGACTGGAGTAGAAGATTCAAGCTTTGCCTATGGATTATTGATGGA 4275 |
| 4276 GCTAACAAGAGCTTACCTTGCGTATGCTGATAATAGCCGAGCTCAAGATTCAGCTGCCTATGCCATTCAGGAGTT 4350 |
| 4351 GCTTTCTATTTATGACTGTAGAGAGATGGAGACCAACGGCCCAGGTCACCAATTGTGGAGGAGATTTCCTGAGCA 4425 |
| 4426 TGTTCGGGAAATACTAGAACCTCATCTAAATACCAGATACAAGAGTTCTCAGAAGTCAACCGATTGGTCTGGAGT 4500 |
| 4501 AAAGAAGCCAATTTACTTAAGTAAATTGGGTAGTAACTTTGCAGAATGGTCAGCATCTTGGGCAGGTTATCTTAT 4575 |
| 4576 GACCATCTATCTTCTTCCACATATTCTGGTGTATGTCTTACTGGGTTGTAATCAAGAAGATCAGCAGGAGGTTTA 4725 |
| 4725 TGCAGAAATTATGGCAGTTCTAAAGCATGACGATCAGCATACCATAAATACCCAAGACATTGCATCTGATCTGTG 4800 |
| 4801 TCAACTCAGTACACAGACTGTGTTCTCCATGCTTGACCATCTCACACAGTGGGCAAGGCACAAATTTCAGGCACT 4875 |
| 4876 GAAAGCTGAGAAATGTCCACACAGCAAATCAAACAGAAATAAGGTAGACTCAATGGTATCTACTGTGGATTATGA 4950 |
| 4951 AGACTATCAGAGTGTAACCCGTTTTCTAGACCTCATACCCCAGGATACTCTGGCAGTAGCTTCCTTTCGCTCCAA 5025 |
| 5026 AGCATACACACGAGCTGTAATGCACTTTGAATCATTTATTACAGAAAAGAAGCAAAATATTCAGGAACATCTTGG 5100 |
| 5101 ATTTTTACAGAAATTGTATGCTGCTATGCATGAACCTGATGGAGTGGCCGGAGTCAGTGCAATTAGAAAGGCAGA 5175 |
| 5176 ACCATCTCTAAAAGAACAGATCCTTGAACATGAAAGCCTTGGCTTGCTGAGGGATGCCACTGCTTGTTATGACAG 5250 |
| 5251 GGCTATTCAGCTAGAACCAGACCAGATCATTCATTATCATGGTGTAGTAAAGTCCATGTTAGGTCTTGGTCAGCT 5325 |
| 5326 GTCTACTGTTATCACTCAGGTGAATGGAGTGCATGCTAACAGGTCCGAGTGGACAGATGAATTAAACACGTACAG 5400 |
| 5401 AGTGGAAGCAGCTTGGAAATTGTCACAGTGGGATTTGGTGGAAAACTATTTGGCAGCAGATGGAAAATCTACAAC 5475 |
| 5476 ATGGAGTGTCAGACTGGGACAGCTATTATTATCAGCCAAAAAAGAGATATCACAGCTTTTTATGACTCACTGAA 5550 |
| 5551 ACTAGTGAGAGCAGAACAAATTGTACCTCTTTCAGCTGCAAGCTTTGAAAGAGGCTCCTACCAACGAGGATATGA 5625 |
| 5626 ATATATTGTGAGATTGCACATGTTATGTGAGTTGGAGCATAGCATCAAACCACTTTTCCAGCATTCTCCAGGTGA 5700 |
| 5701 CAGTTCTCAAGAAGATTCTCTAAAGTGGGTAGCTCGACTAGAAATGACCCAGAATTCCTACAGAGCCAAGGAGCC 5775 |
| 5776 TATCCTGGCTCTCCGGAGGGCTTTACTAAGCCTCAACAAAAGACCAGATTACAATGAAATGGTTGGAGAATGCTG 5850 |
| 5851 GCTGCAGAGTGCCAGGGTAGCTAGAAAGGCTGGTCACCACCAGACAGCCTACAATGCTCTCCTTAATGCAGGGGA 5925 |
| 5926 ATCACGACTCGCTGAACTGTACGTGGAAAGGGCAAAGTGGCTCTGGTCCAAGGGTGATGTTCACCAGGCAATAAT 6000 |
| 6001 TGTTCTTCAAAAAGGTGTTGAATTATGTTTTCCTGAAAATGAAACCCCACCTGAGGGTAAGAACATGTTAATCCA 6075 |
| 6076 TGGTCGAGCTATGCTACTAGTGGGCCGATTTATGGAAGAAACAGCTAACTTTGAAAGCAATGCAATTATGAAAAA 6150 |
| 6151 ATATAAGGATGTGACCGCGTGCCTGCCAGAATGGGAGGATGGGCATTTTTACCTTGCCAAGTACTATGACAAATT 6225 |
| 6226 GATGCCCATGGTCACAGACAACAAAATGGAAAAGCAAGGTGATCTCATCCGGTATATAGTTCTTCATTTTGGCAG 6300 |
| 6301 ATCTCTACAATATGGAAATCAGTTCATATATCAGTCAATGCCACGAATGTTAACTCTATGGCTTCATTATGGTAC 6375 |
| 6376 AAAGGCATATGAATGGGAAAAAGCTGGCCGCTCCGATCGTGTACAAATGAGGAATGATTTGGGTAAAATAAACAA 6450 |
| 6451 GGTTATCACAGAGCATACAAACTATTTAGCTCCATATCAATTTTTGACTGCTTTTTCACAATTGATCTCTCGAAT 6525 |
| 6526 TTGTCATTCTCACGATGAAGTTTTTGTTGTCTTGATGGAAATAATAGCCAAAGTATTTCTAGCCTATCCTCAACA 6600 |
| 6601 AGCAATGTGGATGATGACAGCTGTGTCAAAGTCATCTTATCCCATGCGTGTGAACAGATGCAAGGAAATCCTCAA 6675 |
| 6676 TAAAGCTATTCATATGAAAAAATCCTTAGAGAAGTTTGTTGGAGATGCAACTCGCCTAACAGATAAGCTTCTAGA 6750 |
| 6751 ATTGTGCAATAAACCGGTTGATGGAAGTAGTTCCACATTAAGCATGAGCACTCATTTTAAAATGCTTAAAAAGCT 6825 |
| 6826 GGTAGAAGAAGCAACATTTAGTGAAATCCTCATTCCTCTACAATCAGTCATGATACCTACACTTCCATCAATTCT 6900 |

-continued

| | Sequence Information | |
|---|---|---|
| 6901 | GGGTACCCATGCTAACCATGCTAGCCATGAACCATTTCCTGGACATTGGGCCTATATTGCAGGGTTTGATGATAT | 6975 |
| 6976 | GGTGGAAATTCTTGCTTCTCGGCAGAAACCAAAGAAGATTTCTTTAAAAGGCTCAGATGGAAAGTTCTACATCAT | 7050 |
| 7051 | AGACCGTCATGGTGAAAATATTCTCTTTGATTCTTTGACTGGTGAATGCGTACATGTAGATTTCAATTGTCTTTT | 7125 |
| 7126 | AAGAAAAGATGCAGAGTCTCGTAGAAGAGAACTTCATATTCGAACATATGCAGTTATTCCACTAAATGATGAATG | 7200 |
| 7201 | TGGGATTATTGAATGGGTGAACAACACTGCTGGTTTGAGACCTATTCTGACCAAACTATATAAAGAAAAGGGAGT | 7275 |
| 7276 | GTATATGACAGGAAAAGAACTTCGCCAGTGTATGCTACCAAAGTCAGCAGCTTTATCTGAAAAACTCAAAGTATT | 7350 |
| 7351 | CCGAGAATTTCTCCTGCCCAGGCATCCTCCTATTTTTCATGAGTGGTTTCTGAGAACATTCCCTGATCCTACATC | 7425 |
| 7426 | ATGGTACAGTAGTAGATCAGCTTACTGCCGTTCCACTGCAGTAATGTCAATGGTTGGTTATATTCTGGGGCTTGG | 7500 |
| 7501 | AGACCGTCATGGTGAAAATATTCTCTTTGATTCTTTGACTGGTGAATGCGTACATGTAGATTTCAATTGTCTTTT | 7575 |
| 7576 | CAATAAGGGAGAAACCTTTGAAGTTCCAGAAATTGTGCCATTTCGCCTGACTCATAATATGGTTAATGGAATGGG | 7650 |
| 7651 | TCCTATGGGAACAGAGGGTCTTTTTCGAAGAGCATGTGAAGTTACAATGAGGCTGATGCGTGATCAGCGAGAGCC | 7725 |
| 7726 | TTTAATGAGTGTCTTAAAGACTTTTCTACATGATCCTCTTGTGGAATGGAGTAAACCAGTGAAAGGGCATTCCAA | 7800 |
| 7801 | AGCGCCACTGAATGAAACTGGAGAAGTTGTCAATGAAAAGGCCAAGACCCATGTTCTTGACATTGAGCAGCGACT | 7875 |
| 7876 | ACAAGGTGTAATCAAGACTCGAAATAGAGTGACAGGACTGCCGTTATCTATTGAAGGACATGTGCATTACCTTAT | 7950 |
| 7951 | ACAAGAAGCTACTGATGAAAACTTACTATGCCAGATGTATCTTGGTTGGACTCCATATATGTGAAATGAAATTAT | 8025 |
| 8026 | GTAAAAGAATATGTTAATAATCTAAAAGTAATGCATTTGGTATGAATCTGTGGTTGTATCTGTTCAATTCTAAAG | 8100 |
| 8101 | TACAACATAAATTTACGTTCTCAGCAACTGTTATTTCTCTGATCATTAATTATATGTAAAATAATATACATTC | 8175 |
| 8176 | AGTTATTAAGAAATAAACTGCTTTCTTAATAAAAAAAAAAAAAAAAAAAAAAAAAAAAAAAAA | 8239 |

Sequence ID No. 2: ATR protein

| 1 | MGEHGLELASMIPALRELGSATPEEYNTVVQKPRQILCQFIDRILTDVNVVAVELVKKTDSQPTSV | 66 |
|---|---|---|
| 67 | MLLDFIQHIMKSSPLMFVNVSGSHERKGSCIEFSNWIITRLLRIAATPSCHLLHKKICEVICSLLFLFKSKSPAI | 141 |
| 142 | FGVLTKELLQLFEDLVYLHRRNVMGHAVEWPVVMSRFLSQLDEHMGYLQSAPLQLMSMQNLEFIEVTLLMVLTRI | 216 |
| 217 | IAIVFFRRQELLLWQIGCVLLEYGSPKIKSLAISFLTELFQLGGLPAQPASTFFSSFLELLKHLVEMDTDQLKLY | 291 |
| 292 | EEPLSKLIKTLFPFEAEAYRNIEPVYLNMLLEKLCVMFEDGVLMRLKSDLLKAALCHLLQYFLKFVPAGYESALQ | 366 |
| 367 | VRKVYVRNICKALLDVLGIEVDAEYLLGPLYAALKMESMEIIEEIQCQTQQENLSSNSDGISPKRRRKSSSLNPS | 441 |
| 442 | KRAPKQTEEIKHVDMNQKSILWSALKQKAESLQISLEYSGLKNPVIEMLEGIAVVLQLTALCTVHCSHQNMNCRT | 516 |
| 517 | FKDCQHKSKKKPSVVITWMSLDFYTKVLKSCRSLLESVQKLDLEATIDKVVKIYDALIYMQVNSSFEDHILEDLC | 591 |
| 592 | GMLSLPWIYSHSDDGCLKLTTFAANLLTLSCRISDSYSPQAQSRCVFLLTLFPRRIFLEWRTAVYNWALQSSHEV | 666 |
| 667 | IRASCVSGFFILLQQQNSCNRVPKILIDKVKDDSDIVKKEFASILGOLVCTLHGMFYLTSSLTEPFSEHGHVDLF | 671 |
| 742 | CRNLKATSQHECSSSQLKASVCKPFLFLLKKKIPSPVKLAFIDNLHHLCKHKDFREDETDVKAVLGTLLNLMEDP | 816 |
| 817 | DKDVRVAFSGNIKHILESLDSEDGFIKELFVLRMKEAYTHAQISRNNELKDTLILTTGDIGRAAKGDLVPFALLH | 891 |
| 892 | LLHCLLSKSASVSGAAYTEIRALVAAKSVKLQSFFSQYKKPICQFLVESLHSSQMTALPNTPCQNADVRKQDVAH | 966 |
| 967 | QREMALNTLSEIANVFDFPDLNRFLTRTLQVLLPDLAAKASPAASALIRTLGKQLNVNRREILINNFKYIFSHLV | 1041 |
| 1042 | CSCSKDELERALHYLKNETEIELGSLLRQDFQGLHNELLLRIGEHYQQVFNGLSILASFASSDDPYQGPRDIISP | 1116 |
| 1117 | ELMADYLQPKLLGILAFFNMQLLSSSVGIEDKKMALNSLMSLMKLMGPKHVSSVRVKMMTTLRTGLRFKDDFPEL | 1191 |
| 1192 | CCRAWDCFVRCLDHACLGSLLSHVIVALLPLIHIQPKETAAIFHYLIIENRDAVQDFLHEIYFLPDHPELKKIKA | 1266 |
| 1267 | VLQEYRKETSESTDLQTTLQLSMKAIQHENVDVRIHALTSLKETLYKNQEKLIKYATDSETVEPIISQLVTVLLK | 1341 |
| 1342 | GCQDANSQARKKCGECLGELGAIDPGRLDFSTTETQGKDFTFVTGVEDSSFAYGLLMELTRAYLAYADNSRAQDS | 1416 |
| 1417 | AAYAIQELLSIYDCREMETNGPGHQLWRRFPEHVREILEPHLNTRYKSSQKSTDWSGVKKPIYLSKLGSNFAEWS | 1491 |

-continued

| Sequence Information |
|---|
| 1492 ASWAGYLITKVRHDLASKIFTCCSIMMKHDFKVTIYLLPHILVYVLLGCNQEDQQEVYAEIMAVLKHQDQHTINT 1566 |
| 1567 QDIASDLCQLSTQTVFSMLDHLTQWARHKFQALKAEKCPHSKSNRNKVDSMSTVDYEDYQSVTRFLDLIPPQDTL 1641 |
| 1642 AVASFRSKAYTRAVMHFESFITEKKQNIQEHLGFLQKLYAAMHEPDGVAGVSAIRKAEPSLKEQILEHESLGLLR 1716 |
| 1717 DATACYDRAIQLEPDQIIHYHGVVKSMLGLGQLSTVITQVNGVHANRSEWTDELNTYRVEAAWKLSQWDLVENYL 1791 |
| 1792 AADGKSTTWSVRLGQLLLSAKKRDITAFYDSLKLVRAEQIVPLSAASFERGSYQRGYEYIVRLHMLCELEHSIKP 1866 |
| 1867 LFQHSPGDSSQEDSLNWVARLEMTQNSYRAKEPILALRRALLSLNKRPDYNEMVGECWLQSARVARKAGHHQTAY 1941 |
| 1942 NALLNAGESRLAELYVERAKWLWSKGDVHQALIVLQKGVELCFPENETPPEGKNMLIHGRAMLLVGRFMEETANF 2016 |
| 2017 ESNAIMKKYKDVTACLPEWEDGHFYLAKYYDKLMPMVTDNKMEKQGDLIRYIVLHFGRSLQYGNQFIYQSMPRML 2091 |
| 2092 TLWLDYGTKAYEWEKAGRSDRVQMRNDLGKINKVITEHTNYLAPYQFLTAFSQLISRICHSHDEVFVVLMEIIAK 2166 |
| 2167 VFLAYPQQAMWMMTAVSKSSYPMRVNRCKEILNKAIHNKKSLEKFVGDATRLTDKLLELCNKPVDGSSSTLSMST 2241 |
| 2242 HFKMLKKLVEEATFSEILIPLQSVMIPTLPSILGTHANHASHEPFPGHWAYIAGFDDMVEILASLQKPKKISLKG 2316 |
| 2317 SDGKFYIMMCKPKDDLRKDCRLMEFNSLINKCLRKDAESRRRELHIRTYAVIPLNDECGIIEWVNNTAGLRPILT 2391 |
| 2392 KLYKEKGVYMTGKELRQCMLPKSAALSEKLKVFREFLLPRHPPIFHEWFLRTFPDPTSWYSSRSAYCRSTAVMSM 2466 |
| 2467 VGYILGLGDRHGENILFDSLTGECVHVDFNCLFNKGETFEVPEIVPFRLTHNMVNGMGPMGTEGLFRRACEVTNR 2541 |
| 2542 LMRDQREPLMSVLKTFLHDPLVEWSKPVKGHSKAPLMETGEVVNEKAKTHVLDIEQRLQGVIKTRNRVTGLPLSI 2616 |
| 2617 EGHVHYLIQEATDENLLCQMYLGWTPYM 2664 |

Sequence ID No. 3: rad3.seq
```
   1 GGTACCAAGTAAAAACTGCTTAGTAAGTATAAAACACAGAAGAATCCGCGATCTAGTGAACCAATGCCCTGCGTA   75
  76 TGACGCTCCACTGACGCTATAGTCAATGAGAACTAGGATGTGCGATTATAACTTATCTTTTCAATATTTTCTTAT  150
 151 TATTTATTTAAGAAATAATTGAATTAAAACTCATTTCTTCTTTTATTAGCCGTAAAATAGCTTATTTTCTCTCCT  225
 226 ACTACCTTTCAACAATAACTTTTTTTTTGTTTATTGACCATTATAATCACATCAAAAGTCAAAAAATTCAATCA   300
 301 TTATCAGAAACATCCAGCCTAATATTACTTAAAAGTTAGTTTCCTCTGAAAATTCAGTATCACAAAAGCTCGTTA  375
 376 ATTAGCATCGCTCGATACTTAGTGCACCATGCATCTTCCTTTACCTCGTGAGTGGAAATCGATTTGATAATCGAT  450
 451 TGCCACTTTTCGCATAATTCTATTGAGATATTTTATTACTTACAATCGTCTTTTATAAATGCTCAAGACTTTGAA  525
 526 CGCGCGTGTTGCGTTTTAAAAAGGCCTTTTTTTGAATTGAATCAATGGTTTGATATAGTATGAGCCAACACGCAA  600
 601 AAAGGAAAGCTGGGTCACTCGATCTTTCACCCAGAGGCTTAGATGACAGACAGGCTTTCGGACAGCTTTTGAAAG  675
 676 AAGTATTAGCATTAGACAAAGAACATGAGTTAGGTAGAAGTAATTCTTTACCATCTATGACCTCCGAGCTTGTTG  750
 751 AAGTTTTAATTGAAGTTGGTCTTCTAGCTTTTAAACATGATGATTCAAAATCTGAATTTATCTCTCCTAAGATGC  825
 826 TAAAAGAAGCCCATCTCTCTCTACAAGCGTTAATGCTAATCTTAAAAAGGTCTCCGACAGTTTTGCGGGAGATTA  900
 901 AATCATCTGTTACTCTTTTGGATTGGATTTTACCCAGGACTATATCATTGTTTGCTGATATTCGTTTTATTAAGT  975
 976 TATTTGACTCATTAAAAGAGTTTCATAAGCTAATTTATCAGCTAATCAGTGAAAAGTCATTCCTATGGGACTTAT 1050
1051 ATGCTTCGTTTATGCGTTATTGGAAATATTATATTACAAACGTTTCTTCTATAGTTCTCCAAATCACTAATGCTA 1125
1126 CATTCCCTTACAAGATGCCCTCACCCAATTCTCAACCATTGCAGAGTATCTCCCCAAATTATCCAACCCATCGAG 1200
1201 AGGACAAATTTGATTTACTTATCATTAATATAGAGGAGGCTTGTACATTTTTCTTTGAAAGTGCCCATTTTTTTG 1275
1276 CACAATGCTCATATTTAAAGAAATCCAATTTTCCTAGTCCACCTCTCTTTACAGCGTGGACTTGGATCAAGCCAT 1350
1351 GTTTTTTTAATTTTGTTATTTTATTAAAACGAATCAGCATCGGAGACTCACAGCTCTTTCTACATTTGCATTCAC 1425
1426 GTATAGTCCAAACTTTATGCTGTTTTTCCTTGAATTTTATATATCATGGCCTTCCCATTTGTGAAAAATCTAAAC 1500
1501 ATATTTTAATGTCCTCCATCAACTTAACATTGGGATCATTGAAGAAAACTTATACAGTTGCTAATACTGCTATAT 1575
1576 CTCTTTTTTTTCTCTCTTTATTTGTTTTACCCAAAACTGTAGCTGGTCTATTCTATCCTTTTGGGGTTTCCTTAC 1650
```

-continued

| | Sequence Information | |
|---|---|---|
| 1651 | TTTCTGACTTCAAGGTATTAGAGCAACTTGAACCAGATTCTGATCTCAAAAAGGCAATAATATTATTTAAGTGCA | 1725 |
| 1726 | GATACCAAAGTTCAGAAATAGATCAAACAACTCTCCGTGCTTTTGGCGAAATTTGTACTGGTAAACTTGAAAACA | 1800 |
| 1801 | CGTTGTTTTCTAACTCTGAATTAAACCTTTTTCTTTTACATTATCTTTCCTTGGACAATGACTTGTCAAATATTC | 1875 |
| 1876 | TTAAAGTGGATTTCCAGAATGGTCATAACATATGTACATTTGCAAATGGTGTATAAACAACAACTTAGATGAAC | 1950 |
| 1951 | CGTCTAATTTAAAGCACTTTCGTGAAATGTTAGATTATTATAGCTCTCATAATGTTACAATAAGTGAGGACGACC | 2025 |
| 2026 | TGAAGAACTTCTCTTTAGTTTTGTGTACTCATGTTGCAAAGGTGAATGAGAAAACAAATAGTATTTTCCGCACAT | 2100 |
| 2101 | ATGAAGTACATGGTTGTGAAGTTTGTAACTCATTTTGTTTACTATTTGATGAGCGGTCGCCTTTTAAAATTCCTT | 2175 |
| 2176 | ATCACGAATTGTTTTGTGCATTGCTAAAAAATCCCGCAATAATTTCCTCTTCTGTTAAACAATCATTGTTGCTTG | 2250 |
| 2251 | ATGGCTTTTTTCGGTGGAGCCAGCATTGCTCAAACTTTAATAAAGAATCAATGTTAAGTTTAAGAGAATTTATTA | 2325 |
| 2326 | TGAAAGCATTAGCCAGTACTTCAAGATGTTTACGTGTTGTTGCTGCAAAAGTTTTGCCCATTTTCATTAAGGGAC | 2400 |
| 2401 | *CTAATAATCTTGATATAGTTGAATTTCACAAGGAAAGTAAAGCCTTGATTTTAATACGTTGAAAATATTGGCGG* | 2475 |
| 2476 | *TGGAAAATACAGCTATTTTAGAA*ACG*GTCAT*TCT*TTCCTGGATCTCCTTATCTAGAGTGGTAGAAGAAGAAGAAT* | 2550 |
| 2551 | *TACATTTTGTACTATTGGAAGTTATATCTTCTGTGATAAACAGCGGAATATTTTATCAAGGCATTGGTCTCAGCG* | 2625 |
| 2626 | *CTCTGCAACAAATTGCCTCGACGCGTCATATATCCGTTTGGCAATTACTTTCTCCATATTGGCCAACAGTGTCCG* | 2700 |
| 2701 | *TTGCGATTGTCCAAGGTATGGGTAAAAAACCGAACATAGCCAGTTTATTTGCTCAGCTTATGAATATTTCCGAGG* | 2775 |
| 2776 | *GCGATTTTCTTATTCGAACAGAGGCGTACACTTTACCATTCCTTGTACTTACTAAAAACAAAGCGTTAATAGTAC* | 2850 |
| 2851 | *GTATAGCTGAACTTTCACAAAGTGATGTTGCTACTTTGTGCCTTACCAATATGCATAAAATCCTTGCTTCGCTAC* | 2925 |
| 2926 | *TTACTACGGATCATCCTAATTTGGAAGAGAGTGTGATGCTTCTTCTTTCACTGGCCACTTCTGATTTTGAAAAAG* | 3000 |
| 3301 | *TTGATTTAACGTCTTTGTTACGCTCTGATCCTATTTCTATTACTGTGGAGTTGTTACAGCTTTATCAGAATGATG* | 3075 |
| 3076 | *TTCCTCATGAAAAAATTGAAAATGCTTTAAGAAAGGTAGCAATGATTCTGTCTCAAGTGGTTAATGACGAAGACT* | 3150 |
| 3151 | *TGAGCAATAAGGAATTACTTTATGATTTTTTAATAATCACATTTTGGGTATCTTAGCAGAATTTTCTAATATCC* | 3225 |
| 3226 | *TTAACGACCTGAAAGGAAAGACTTCAATTAATGAAAAGATTAAGACAATTGTCGGCATTGAAAAAATGTTATCTT* | 3300 |
| 3301 | *TATGTGGAGGTGCAGTCAAACTTGGATTACCACAGATACTTTCTAATTTACAAAGTGCTTTTCAAAATGAGCACT* | 3375 |
| 3376 | *TAAGGTTTTATGCAATCAAAGCTTGGTTCAGTTTGATATTAGCAACCAAGGAGCCCGAGTATAGTTCAATTGCTG* | 3450 |
| 3451 | *GTTTAAGTCTTGTAATTTTACCTCCTTTATTCCCTTATTTAGAACCACAAGAAGCAGAGCTAGTAATTCAAATAT* | 3525 |
| 3526 | *TTGATTTTATTTCTTCTGACACACACAAGTGCCTACAAGGATTAAAGTGGGCTATCCCCACCAGTCTGGATTCAG* | 3600 |
| 3601 | *CGTGCTTTAGCCTTAAGGCTAAAGAAATATTCTGTTCGCTTCAAAATGAAGATTTTTACTCTGAGCTTCAAAGTA* | 3675 |
| 3676 | *TAATTAAGTGTTTAACTAACGAAAATGAGCCAGTTTGTTATTTAGGTTTACAAAAATTAGAACTTTTTTTCAAG* | 3750 |
| 3751 | *CCAAGGTGGACGAGTTACATGACACACTAAATTTGGACATATCCAACGAAGTTCTGGACCAATTACTAAGATGCC* | 3825 |
| 3826 | *TTTTAGATTGTTGTGTAAAATATGCTTCAACAAATATGCAAATATCATATCTTGCTGCAAAAAATCTTGGTGAAT* | 3900 |
| 3901 | *TGGGTGCGATAGATCCCAGCCGCGCCAAGGCTCAACATATTATTAAAGAAACAGTTGTTCTTGATAACTTTGAAA* | 3975 |
| 3976 | *ACGGAGAAGAAAGTTTGAAGTTTATTCTAGATTTTATGCAATCGCAGTTAATTCCAGCTTTCCTTGTTACTACTG* | 4050 |
| 4051 | *ATACTAAAGCACAAGGTTTTCTTGCCTATGCTCTGCAAGAGTTTCTAAAGCTTGGTGGATTCAAGTCCGCAGTGA* | 4125 |
| 4126 | *TTAATAAAAAAAAGGGACTAACTGTGGTAACAGAACATTGGATGTCTTTGCCTGATTTATCCAAACGTGTGCTTA* | 4200 |
| 4201 | *TACCATTTTTAACTTCCAAGTATCATTTAACACCAATCCCCAAAATTGACATTCGGTACCCTATTTATAAAGAAA* | 4275 |
| 4276 | *ATGTTACTATTCATACTTGGATGCAGTTGTTTTCTCTTAAATTGATGGAGTACGCCCATTCGCAAAACGCTGAAA* | 4350 |
| 4351 | *AAATATTTGGTATTTGTTCGAAAGTAGTGAAAGACCAAGAGGTTAACATTCCCTGTTTTCTTCTTCCCTTTCTTG* | 4425 |
| 4426 | *TTTTAAATGTTATTTTAACCGAGTCAGAACTGGAAGTTAATAAAGTCATTGAAGAATTCCAGCTTGTTATTAATC* | 4500 |
| 4501 | *AACCGGGACCTGATGGATTAAAATTCCGTGGGGCAACAAAGATACACCTCATTTGTAGATGTATTTTTAAGATTG* | 4575 |

| Sequence Information |
|---|
| 4576 *TGGATTACCTTAACAAATGGCTTCGCATGCGAAAGAAGAGGAATTGGGATAGACGTTCTGCCATTGCAAGGAAAG* 4650 |
| 4651 *AGAACCGTTATATGTCGGTGGAAGATGCTACCTCTCGAGAATCATCGATCTCAAAAGTTGAGTCATTTCTTTCTC* 4725 |
| 4726 *GATTTCCTTCAAAAACATTAGGTATTCTCTCTTTAAATTGTGGATTTCATGCTCGTGCATTGTTTTATTGGGAGC* 4800 |
| 4801 *AACACATACGTAATGCTACAGCTCCATATGCAGCTTTAGAGTCCGATTATAGAGTTTTGCAGGAAATATATGCTG* 4875 |
| 4876 *GAATTGATGATCCAGATGAAATCGAAGCAGTGTCTTTAAATTTCCATGATTACTCGTTTGATCAACAACTCCTTT* 4950 |
| 4951 *TACATGAAAATTCAGGAACATGGGACTCGGCTTTGAGTTGTTACGAAATTATTATTCAAAAGGATCCTGAAAATA* 5025 |
| 5026 *AAAAGGCGAAAATCGGTTTGCTTAACAGCATGCTGCAATCGGGGCATTATGAATCTCTTGTTTTGAGTTTAGATT* 5100 |
| 5101 *CTTTTATAATCAATGACAACCACGAGTATTCGAAGATGTTAAATTTGGGTATTGAAGCTTCATGGCGTTCGCTAT* 5175 |
| 5176 *CTATTGATTCGTTAAAAAAGTGTCTTTCAAAAAGCAACTTGGAATCTTTCGAAGCTAAATTGGGTAGCATATTTT* 5250 |
| 5251 *ACCAATACCTACGGAAGGATTCTTTTGCTGAATTGACGGAGCGGCTGCAACCCTTGTACGTTGATGCTGCTACAG* 5325 |
| 5326 *CAATTGCAAACACAGGAGAAAATTCAGCCTATGATTGTTATGATATTTTATCTAAGCTGCACGCAATTAATGACT* 5400 |
| 5401 *TTAGTAGGATTGCTGAAACTGACGGAATTGTTTCCGACAATCTTGATATTGTTCTTCGCCGTCGGCTTAGCCAAG* 5475 |
| 5476 *TAGCTCCGTACGGTAAATTCAAGCACCAAATCCTGTCCACTCACTTAGTTGGCTATGAAAAATTTGAAAACACGA* 5550 |
| 5551 *AGAAAACTGCTGAAATATATCTCGAGATTGCAAGAATATCTCGAAAAAATGGTCAATTTCAAAGAGCCTTCAATG* 5625 |
| 5626 *CCATCCTCAAAGCAATGGATTTAGATAAACCGCTAGCAACAATAGAGCACGCACAATGGTGGTGGCATCAAGGGC* 5700 |
| 5701 *AACATCGTAAAGCTATTTCTGAATTGAATTTTTCGCTTAATAACAACATGTTTGATTGGTTGATGAGCATGAAG* 5775 |
| 5776 *AAAGACCTAAAAATCGTAAAGAAACTTTAGGAAATCCACTTAAAGGAAAAGTGTTCTTGAAACTTACAAAATGGC* 5850 |
| 5851 *TCGGAAAAGCTGGCCAACTGGGATTGAAGGATTTGGAGACGTATTATCATAAAGCGGTAGAGATTTA<u>CT</u>CAGAAT* 5925 |
| 5926 *GTGAGAATACGCATTATTATCTTGGCCATCATCGAGTTTTAATGTATGAAGAAGAACAAAAGCTCCCAGTTAATG* 6000 |
| 6001 *AACAGAGCGAACGATTTTTAAGTGGTGAGTTAGTAACTCGCATAATTAACGAATTTGGTCGATCTTTGTACTATG* 6075 |
| 6076 *GTACAAATCATATATATGAAAGTATGCCAAAATTGCTCACACTGTGGCTTGATTTTGGGGCCGAAGAACTTCGCT* 6150 |
| 6151 *TATCTAAAGATGACGGCGAAAAGTACTTTCGTGAACACATTATCTCTTCGAGAAAAAAATCTTTGGAACTTATGA* 6225 |
| 6226 *ATTCGAATGTTTGTCGCCTTTCTATGAAAATTCCTCAATACTTTTTTGTCCTTGCATTATCCCAAATGATATCCA* 6300 |
| 6301 *GAGTATGCCATCCAAATAATAAAGTTTATAAAATTTTGGAACATATAATTGCAAACGTTGTAGCATCTTATCCTG* 6375 |
| 6376 *GGGAGACGCTATGGCAATTAATGGCAACAATAAAATCGACTTCTCAAAAGCGCTCGCTTCGTGGAAAAAGCATTT* 6450 |
| 6451 *TAAATGTTTTACATTCTAGGAAGCTTTCTATGTCTTCCAAAGTTGATATAAAAGCACTCAGTCAATCTGCAATTC* 6525 |
| 6526 *TCATTACTGAAAAGTTAATCAATTTGTGCAATACAAGGATTAACAGTAAATCTGTAAAAATGAGCTTAAAGGATC* 6600 |
| 6601 ATTTTCGGCTTTCTTTTGATGATCCGGTAGATTTAGTCATTCCTGCTAAATCATTTTTAGACATTACTTTACCAG 6675 |
| 6676 CTAAAGATGCTAACAGAGCTAGTCATTATCCATTTCCAAAAACTCAGCCTACTCTGTTGAAATTTGAGGATGAGG 6750 |
| 6751 TGGATATAATGAACTCTCTTCAAAAACCAAGAAAAGTGTACGTTAGAGGTACGGATGGCAACTTATACCCATTCT 6825 |
| 6826 TGTGCAAACCCAAAGATGATCTTCGTAAGGATGCTAGATTGATGGAATTTAATAATCTTATTTGTAAAATATTGA 6900 |
| 6901 GGAAAGATCAAGAAGCGAACAGAAGGAACTTGTGTATTAGAACTTATGTTGTTATTCCTTTAAATGAAGAATGCG 6975 |
| 6976 GATTTATCGAATGGGTAAATCATACTCGTCCATTTAGAGAAATTTTGTTAAAAAGCTATAGACAGAAAAACATTC 7050 |
| 7051 CCATATCATATCAAGAAATCAAAGTTGATTTAGACTTTGCACTGCGAAGTCCTAACCCTGGTGATATATTTGAAA 7125 |
| 7126 AGAAAATCTTACCGAAATTTCCTCCAGTTTTTTATGAGTGGTTTGTTGAATCTTTCCCAGAACCAAATAATTGGG 7200 |
| 7201 TTACTAGTAGACAAAACTATTGCCGAACTTTAGCAGTAATGTCAATAGTTGGCTACGTTTTGGGTTTGGGAGATC 7275 |
| 7276 GCCATGGCGAAAACATATTGTTTGATGAATTTACAGGTGAAGCTATCCATGTCGATTTCAACTGTCTTTTTGATA 7350 |
| 7351 AAGGTCTTACTTTTGAAAAACCTGAAAAGGTGCCGTTCAGATTAACTCATAATATGGTAGATGCAATGGGTCCGA 7425 |
| 7426 CAGGTTATGAAGGGGGTTTCAGGAAAGCTAGCGAAATAACGATGCGGCTTCTTCGCTCAAACCAAGATACATTGA 7500 |

-continued

Sequence Information

```
7501 TGAGCGTACTAGAGTCTTTCCTACATGATCCTTTAGTCGAGTGGAATAGAAAGAAGTCGTCAAGCAAGTACCCGA 7575

7576 ATAATGAAGCAAATGAAGTTTTGGATATAATTCGCAAAAAATTTCAAGGCTTTATGCCAGGGGAGACGATACCTT 7650

7651 TATCTATTGAAGGGCAAATTCAAGAATTGATCAAATCTGCTGTCAACCCAAAAAACCTGGTAGAAATGTACATTG 7725

7726 GTTGGGCTGCTTATTTCTAGCATTTTACTAACAAAAATTTCAATGAACAAGCTACCCATTATTAAACTTATGATT 7800

7801 TGAATCGAAGATATTTTATTTATTAATCCGATGAAGAATTCTCGCTGAGTTGTTCAATTTCTTGTAATTTTCCTT 7875

7876 CCATTTCTAAATCGTCGATTCGCTTAAATAGGGCACTGGCTTTTTGTGCATTTTTCTCTCGTAAAGCAGCTTCTG 7950

7951 ATTGAAAAAAAGCTATATCTGTTTCTGAGTCATCATCCGAATCAACAATATATTTTGCAGATCGACCTGCAG     8022
```

In italics, sequenced by Seaton, et al.
On Bold are those bases deleted in Seaton et al. (2499, 22501, 2507, 2509)
Underlined are the two bases either side of a single C insert (5918/5919) in Seaton
et al. (i.e., incorrect base not shown, but the one residue either side is)

Sequence ID No. 4: rad3 protein

```
   1 MSQHAKRKAGSLDLSPRGLDDRQAFGQLLKEVLALDKEHELGRSNSLPSMTSELVEVLIEVGLLAFKHDDSKSEF   75

76 ISPKMLLEAHLSLQALMLILKRSPTVLREIKSSVTLLDWILPRTISLFADIRFIKLFDSLKEFHKLIYQLISEKS  150

151 FLWDLYASFMRYWKYYITNVSSIVLQITNATFPYKMPSPNSQPLQSISPNYPTHREDKFDLLIINIEEACTFFFE  225

226 SAHFFAQCSYLKKSNFPSPPLFTAWTWIKPCFFNFVILLKRISIGDSQLFLHLHSRIVQTLCCFSLNFIYHGLPI  300

301 CEKSKHILMSSINLTLGSLKKTYTVANTAISLFFLSLFVLPKTVAGLFYPFGVSLLSDFKVLEQLEPDSDLKKAI  375

376 ILFKCRYQSSEIDQTTLRAFGEICTGKLENTLFSNSELMLFLLHYLSLDNDLSNILKVDFQNGHNICTFAKWCIN  450

451 NNLDEPSNLKHFREMLDYYSSHNVTISEDDLKNFSLVLCTHVAKVNEKTNSIFRTYEVHGCEVCNSFCKKFDERS  525

526 PFKIPYHELFCALLKNPDIISSSVKQSLLLDGFFRWSQHCSNFNKESMLSLREFIMKALASTSRCLRVVAAKVLP  600

601 IFIKGPNNLDIVEFHKESKALIFNTLKILAVENTAILETVILSWISLSRVVEEEELHFVLLEVISSVINSGIFYQ  675

676 GIGLSALQQIASTRHISVWQKKSPYWPTVSVAIVQGMGKKPNIASLFAQLMNISEGDFLIRTQAYTLPFLVLTKN  750

751 KALIVRIAELSQSDVATLCLTNMHKILASLLIIDHPNLEESVMLLLSLATSDFEKVDLTSLLRSDPISITVELLQ  825

826 LYQNDVPHEKIENALRKVAMIVSQVVNDEDLSNKELLYDFFNNHILGILAEFSNILNDLKGKTSINEKIKTIVGI  900

901 EKMLSLCGGAVKLGLPQILSNLQSAFQNEHLRFYAIKAWFSLILATKEPEYSSIAGLSLVILPPLFPYLEPQEAE  975

976 LVIQIFDFISSDTHKCLQGLKWAIPTSLDSACFSLKAKEIFCSLQNEDFYSELQSIIKCLTNENEPVCYLGLQKL 1050

1051 ELFFQAKVDELHDTLNLDISNEVLDQLLRCLLDCCVKYASTNMQISYLAAKNLGELGAIDPSRAKAQHIIKETVV 1125

1126 LDNFENGEESLKFILDFMQSQLIPAFLVTTDTKAQGFLAYALQEFLKLGGFKSAVINKKKGLTVVTEHWMSLPDL 1200

1201 SKRVLIPFLTSKYHLTPIPKIDIRYPIYKENVTIHTWMQLFSLKLMEYAHSQNAEKIFGICSKVVKDQEVNIPCF 1275

1276 LLPFLVLNVILTESELEVNKVIEEFQLVINQPGPDGLNSVGQQRYTSFVDVFFKIVDYLNKWLRMRKKRNWDRRS 1350

1351 AIARKENRYMSVEDATSRESSISKVESFLSRFPSKTLGIVSLNCGFHARALFYWEQHIRNATAPYAALESDYRVL 1425

1426 QEIYAGIDDPDEIEAVSLNNFHDYSFDQQLLHENSGTWDSALSCYEIIIQKDPENKKAKIGLLNSMLQSGHYESL 1500

1501 VLSLDSFIINDNHEYSKMLNLGIEASWRSLSIDSLKKCLSKSNLESFEAKLGSIFYQYLRKDSFAELTERLQPLY 1575

1576 VDAATAIANTGAHSAYDCYDILSKLHAINDFSRIAETDGIVSDNLDIVLRRRLSQVAPYGKFKHQILSTHLVGYE 1650

1651 KFENTKKTAEIYLEIARISRKNGQFQRAFNAILKAMDLDKPLATIEHAQWWWHQGQHRKAISELNFSLNNNMFDL 1725

1726 VDEHEERPKNRKETLGNPLKGKVFLKLTKWLGKAGQLGLKDLETYYHKAVEIYSECENTHYYLGHHRVLMYEEEQ 1800

1801 KLPVNEQSERFLSGELVTRIINEFGRSLYYGTNHIYESMPKLLTLWLDFGAEELRLSKDDGEKYFREHIISSRKK 1875

1876 SLELMNSNVCRLSMKIPQYFFLVALSQMISRVCHPNNKVYKILEHIIANVVASYPGETLWQLMATIKSTSQKRSL 1950

1951 RGKSILNVLHSRKLSMSSKVDIKALSQSAILITEKLINLCNTRINSKSVKMSLKDHFRLSFDDPVDLVIPAKSFL 2025

2026 DITLPAKDANRASHYPFPKTQPTLLKFEDEVDIMNSLQKPRKVYVRGTDGNLYPFLCKPKDDLRKDARLMEFNNL 2100

2101 ICKILRKDQEANRRNLCIRTYVVIPLNEECGFIEWVNHTRPFREILLKSYRQKNIPISYQEIKVDLDFALRSPNP 2175
```

-continued

Sequence Information

2176 GDIFEKKILPKFPPVFYEWFVESFPEPNNWVTSRQNYCRTLAVMSIVGYVLGLGDRHGENILFDEFTGEAIHVDF 2250

2251 NCLFDKGLTFEKPEKVPFRLTHNMVDAMGPTGYEGGFRKASEITMRLLRSNQDTLMSVLESFLHDPLVEWNRKKS 2325

2326 SSKYPNNEANEVLDIIRKKFQGFMPGETIPLSIEGQIQELIKSAVNPKNLVEMYIGWAAYF 2386

---

What is claimed is:

1. A purified and isolated polynucleotide encoding an ATR polypeptide that has lipid kinase activity, said polynucleotide selected from the group consisting of:
   (a) a polynucleotide encoding the amino acid sequence set out in SEQ ID NO: 2,
   (b) a polynucleotide encoding the amino acid sequence set out in SEQ ID NO: 4, and
   (c) a polynucleotide which hybridizes to the complement of the polynucleotide of (a) or (b) under conditions including a final wash at 55° C.

2. A purified and isolated polynucleotide encoding an ATR polypeptide that has lipid kinase activity, said polynucleotide selected from the group consisting of:
   a) the polynucleotide set out in SEQ ID NO: 1;
   b) the polynucleotide set out in SEQ ID NO: 3; and
   c) a polynucleotide that hybridizes to the complement of the polynucleotide of (a) or (b) under conditions including a final wash at 55° C.

3. An expression vector comprising the polynucleotide according to claim 1 or 2.

4. An isolated host cell transformed or transfected with a polynucleotide according to claim 1 or 2.

5. A method for producing an ATR polypeptide comprising the step of growing the host cell of claim 4 under conditions in which expression of the ATR polypeptide occurs.

6. A method for detecting the presence of a polynucleotide according to claim 1 or 2 in a human or animal body sample comprising the steps of
   (a) contacting a human or animal body sample with a probe comprising a polynucleotide according to claim 1 or 2 under conditions which permit hybridization; and
   (b) detecting in the sample any duplex formed between the probe and a nucleic acid.

* * * * *

UNITED STATES PATENT AND TRADEMARK OFFICE
CERTIFICATE OF CORRECTION

PATENT NO. : 6,632,936 B2
DATED : October 14, 2003
INVENTOR(S) : Antony M. Carr

It is certified that error appears in the above-identified patent and that said Letters Patent is hereby corrected as shown below:

Title page,
Insert Item -- [73] Assignee: Icos Corporation --.

Column 1,
Line 35, please delete "aeaxia" and insert in its place -- ataxia --.
Line 41, please delete "phenotype," and insert in its place -- phenotype: --.
Line 48, please delete "...1985)." and insert in its place -- ...1985), --.
Line 65, please delete "(ataxia and r ad related)," and insert in its place -- ataxia and rad related), --.

Column 2,
Line 17, please delete "stand" and insert in its place -- strand --.
Line 20, please delete "die" and insert in its place -- the --.
Line 20, please delete "polynucleotides" and insert in its place -- polynucleotide --.
Line 53, please delete "presence of absence" and insert in its place -- presence or absence --.
Line 56, please delete "an." and insert in its place -- art. --.

Column 3,
Line 53, please delete "staring" and insert in its place -- starting --.
Line 67, please delete "pa," and insert in its place -- primate, --.

Column 4,
Line 14, please delete "AIR" and insert in its place -- ATR --.
Line 30, please delete "fiction." and insert in its place -- function. --.
Line 40, please delete "using by" and insert in its place -- by using --.
Line 47, please delete "contain" and insert in its place -- containing --.
Line 58, please delete "of this any other" and insert in its place -- of this or any other --.
Line 64, please delete "she" and insert in its place -- sequence --.

Column 5,
Lines 1 and 3, please delete "stand" and insert in its place -- strand --.
Line 6, please delete "tenon" and insert in its place -- termination --.
Line 23, please delete "cancer." and insert in its place -- cancer, --.
Line 44, please delete "hose" and insert in its place -- those --.
Line 48, please delete "The "lipid..."" and insert in its place -- The term "lipid... --.
Line 52, please delete "invention those" and insert in its place -- invention are those --.
Line 56, please delete "...conserved. In..." and insert in its place -- conserved. (begin new paragraph) In --.

UNITED STATES PATENT AND TRADEMARK OFFICE
CERTIFICATE OF CORRECTION

PATENT NO.   : 6,632,936 B2
DATED         : October 14, 2003
INVENTOR(S)  : Antony M. Carr It is certified that error appears in the above-identified patent and that said Letters Patent is hereby corrected as shown below:

Column 6,
Line 8, please delete "van" and insert in its place -- variants --.
Line 34, please delete "table indicates" and insert in its place -- table which indicates --.
Line 56, please delete "intend" and insert in its place -- interact --.

Column 7,
Line 28, please delete "an" and insert in its place -- art --.
Line 37, please delete "may be may" and insert in its place -- may be made --.

Column 8,
Line 1, please delete "polypeptide" and insert in its place -- polypeptides --.
Line 27, please delete "polynucleotide" and insert in its place -- polynucleotides --.
Line 44, please delete "condition" and insert in its place -- conditions --.

Column 9,
Line 55, please delete "se" and insert in its place -- kinase --.
Line 65, please delete "method" and insert in its place -- methods --.

Column 10,
Line 13, please delete "die" and insert in its place -- the --.
Line 34, please delete "anticancer" and insert in its place -- anti-cancer --.

Column 11,
Line 32, please delete "presence of absence" and insert in its place -- presence or absence --.
Line 36, please delete "courting." and insert in its place -- counting. --.

Column 12,
Line 14, please delete "(PI-3) related" and insert in its place -- (PI-3)-related --.
Line 27, please delete "interventions" and insert in its place -- interventions. --.
Line 30, please delete "molecules" and insert in its place -- molecules. --.
Line 50, please delete "domain:" and insert in its place -- domain; --.
Line 51, please delete "fire" and insert in its place -- first --.
Line 65, please delete "reporter gene," and insert in its place -- IacZ reporter gene, --.

Column 13,
Line 39, please delete "domain:" and insert in its place -- domain; --.
Line 59, please delete "GALA" and insert in its place -- GAL4 --.

UNITED STATES PATENT AND TRADEMARK OFFICE
CERTIFICATE OF CORRECTION

PATENT NO.     : 6,632,936 B2
DATED          : October 14, 2003
INVENTOR(S)    : Antony M. Carr It is certified that error appears in the above-identified patent and that said Letters Patent is hereby corrected as shown below:

Column 14,
Line 1, please delete "present" and insert in its place -- presence --.
Line 38, please delete "anti cancer" and insert in its place -- anti-cancer --.

Column 15,
Line 43, please delete "described" and insert in its place -- described above. --.
Line 62, please delete "10" and insert in its place -- to --.

Column 16,
Line 6, please delete "...be so with any vehicle" and insert in its place -- ...be mixed with any vehicle... --.
Line 9, please delete "...pharmaceutically carrier..." and insert in its place
-- ...pharmaceutically acceptable carrier --.
Line 38, please delete "breat" and insert in its place -- breast --.
Line 53, please delete "software," and insert in its place -- software. --.
Line 13, please delete "strain" and insert in its place -- strain, --.
Line 17, please delete "at." and insert in its place -- al. --.

Column 17,
Line 21, please delete "rad3.D2230A." and insert in its place -- rad3.D2230A, --.
Line 23, please delete "da not shown)," and insert in its place -- (data not shown) --.
Line 31, please delete "Dull" and insert in its place -- null --.
Line 32, please delete "veils" and insert in its place -- cells --.
Line 48, please delete "methods)." and insert in its place -- methods); --.
Lines 48-49, please delete "(ataxia and lad related)" and insert in its place -- (ataxia and rad related) --.
Line 53, please delete "Tell" and insert in its place -- Tel1 --.
Line 67, please delete "in" and insert in its place -- induced --.

Column 18,
Line 1, please delete "Ogawa." and insert in its place -- Ogawa, --.
Line 1, please delete "1" and insert in its place -- I --.
Line 3, please delete "mote" and insert in its place, -- more --.
Line 42, please delete "se" and insert in its place -- kinase --.
Line 50, please delete "protein." and insert in its place -- protein, --.

UNITED STATES PATENT AND TRADEMARK OFFICE
CERTIFICATE OF CORRECTION

PATENT NO. : 6,632,936 B2
DATED : October 14, 2003
INVENTOR(S) : Antony M. Carr

It is certified that error appears in the above-identified patent and that said Letters Patent is hereby corrected as shown below:

Column 19,
Line 10, please delete "conserved" and insert in its place -- conserved. --.
Line 12, please delete "(MEC1/SAD3)." and insert in its place -- (MEC1/SAD3), --.
Line 19, please delete "Onion." and insert in its place -- function. --.
Line 20, please delete "has1" and insert in its place -- hus1 --.
Line 21, please delete "phenotype" and insert in its place -- phenotypes --.
Line 24, please delete "rad" and insert in its place -- rad3 --.
Line 33, please delete "Tellp," and insert in its place -- Tel1p, --.
Line 44, please delete "his defines two sully..." and insert in its place -- This defines two structurally... --.
Line 53, please delete "1992:" and insert in its place -1992; --.
Line 56, please delete "biomycin" and insert in its place -- bleomycin --.

Column 20,
Line 15, please delete "at" and insert in its place -- al. --.
Line 19, please delete "C-terminsl" and insert in its place -- C-terminal --.
Line 50, please delete "sequencen" and insert in its place -- sequence --.
Line 61, please delete "kb." and insert in its place -- kb). --.

Column 21,
Line 16, please delete "234" and insert in its place -- 23$\underline{4}$ --.
Line 24, please delete "$_{32}$P" and insert in its place -- $^{32}$P --.
Line 27, please delete "poiy" and insert in its place -- poly --.
Line 42, please delete "human1rodent" and insert in its place -- human/rodent --.
Line 53, please delete "-tag" and insert in its place -- tag --.
Line 57, please delete "Maundrell." and insert in its place -- Maundrell, --.
Line 59, please delete "EDTA." and insert in its place -- EDTA, --.
Line 57, please delete "timed" and insert in its place -- times --.

Column 22,
Line 24, please delete "pombe," and insert in its place -- pombe. --.
Line 42, please delete "Trent, I.M.," and insert in its place -- Trent, J.M., --.

Column 23,
Line 27, please delete "(1990)," and insert in its place -- (1990). --.
Line 36, please delete "A.R" and insert in its place -- A.R. --.

UNITED STATES PATENT AND TRADEMARK OFFICE
CERTIFICATE OF CORRECTION

PATENT NO.   : 6,632,936 B2
DATED        : October 14, 2003
INVENTOR(S)  : Antony M. Carr It is certified that error appears in the above-identified patent and that said Letters Patent is hereby corrected as shown below:

<u>Column 24,</u>
Line 28, please delete "checkpoints." and insert in its place -- checkpoints, --.

Signed and Sealed this

Twenty-eighth Day of December, 2004

JON W. DUDAS
*Director of the United States Patent and Trademark Office*

UNITED STATES PATENT AND TRADEMARK OFFICE
CERTIFICATE OF CORRECTION

PATENT NO. : 6,632,936 B2
APPLICATION NO. : 09/029047
DATED : October 14, 2003
INVENTOR(S) : Antony M. Carr It is certified that error appears in the above-identified patent and that said Letters Patent is hereby corrected as shown below:

Title Page Item [73],
Assignee information is missing from cover page, please insert the following:

Icos Corporation

In the Specification:

Column 1, line 35, please delete "aeaxia" and insert in its place --ataxia--.

Column 1, line 41, please delete "phenotype," and insert in its place --phenotype:--.

Column 1, line 48, please delete "...1985)." and insert in its place --...1985),--.

Column 1, line 65, please delete "(ataxia and r ad related)," and insert in its place --(ataxia and rad related),--.

Column 2, line 17, please delete "stand" and insert in its place --strand--.

Column 2, line 20, please delete "die" and insert in its place --the--.

Column 2, line 20, please delete "polynucleotides" and insert in its place --polynucleotide--.

Column 2, line 53, please delete "presence of absence" and insert in its place --presence or absence--.

Column 2, line 56, please delete "an." and insert in its place --art.--.

Column 3, line 53, please delete "staring" and insert in its place --starting--.

Column 3, line 67, please delete "pa," and insert in its place --primate,--.

Column 4, line 14, please delete "AIR" and insert in its place --ATR--.

Column 4, line 30, please delete "fiction." and insert in its place --function.--.

Column 4, line 40, please delete "using by" and insert in its place --by using--.

Column 4, line 47, please delete "contain" and insert in its place --containing--.

UNITED STATES PATENT AND TRADEMARK OFFICE
CERTIFICATE OF CORRECTION

PATENT NO. : 6,632,936 B2
APPLICATION NO. : 09/029047
DATED : October 14, 2003
INVENTOR(S) : Antony M. Carr It is certified that error appears in the above-identified patent and that said Letters Patent is hereby corrected as shown below:

Column 4, line 58, please delete "of this any other" and insert in its place --of this or any other--.

Column 4, line 64, please delete "she" and insert in its place --sequence--.

Column 5, line 1, please delete "stand" and insert in its place --strand--.

Column 5, line 3, please delete "stand" and insert in its place --strand--.

Column 5, line 6, please delete "tenon" and insert in its place --termination--.

Column 5, line 23, please delete "cancer." and insert in its place --cancer,--.

Column 5, line 44, please delete "hose" and insert in its place --those--.

Column 5, line 48, please delete "The "lipid..."" and insert in its place --The term "lipid...--.

Column 5, line 52, please delete "invention those" and insert in its place --invention are those--.

Column 5, line 56, please delete "...conserved. In..." and insert in its place --conserved. (begin new paragraph) In--.

Column 6, line 8, please delete "van" and insert in its place --variants--.

Column 6, line 34, please delete "table indicates" and insert in its place --table which indicates--.

Column 6, line 56, please delete "intend" and insert in its place --interact--.

Column 7, line 28, please delete "an" and insert in its place --art--.

Column 7, line 37, please delete "may be may" and insert in its place --may be made--.

Column 8, line 1, please delete "polypeptide" and insert in its place --polypeptides--.

Column 8, line 27, please delete "polynucleotide" and insert in its place --polynucleotides--.

UNITED STATES PATENT AND TRADEMARK OFFICE
CERTIFICATE OF CORRECTION

| | |
|---|---|
| PATENT NO. | : 6,632,936 B2 |
| APPLICATION NO. | : 09/029047 |
| DATED | : October 14, 2003 |
| INVENTOR(S) | : Antony M. Carr |

It is certified that error appears in the above-identified patent and that said Letters Patent is hereby corrected as shown below:

Column 8, line 44, please delete "condition" and insert in its place --conditions--.

Column 9, line 55, please delete "se" and insert in its place --kinase--.

Column 9, line 65, please delete "method" and insert in its place --methods--.

Column 10, line 13, please delete "die" and insert in its place --the--.

Column 10, line 34, please delete "anticancer" and insert in its place --anti-cancer--.

Column 11, line 32, please delete "presence of absence" and insert in its place --presence or absence--.

Column 11, line 36, please delete "courting." and insert in its place --counting.--.

Column 12, line 14, please delete "(PI-3) related" and insert in its place --(PI-3)-related--.

Column 12, line 27, please delete "interventions" and insert in its place --interventions.--.

Column 12, line 30, please delete "molecules" and insert in its place --molecules.--.

Column 12, line 50, please delete "domain:" and insert in its place --domain;--.

Column 12, line 51, please delete "fire" and insert in its place --first--.

Column 12, line 65, please delete "reporter gene," and insert in its place --lacZ reporter gene,--.

Column 13, line 39, please delete "domain:" and insert in its place --domain;--.

Column 13, line 59, please delete "GALA" and insert in its place --GAL4--.

Column 14, line 1, please delete "present" and insert in its place --presence--.

UNITED STATES PATENT AND TRADEMARK OFFICE
CERTIFICATE OF CORRECTION

PATENT NO. : 6,632,936 B2
APPLICATION NO. : 09/029047
DATED : October 14, 2003
INVENTOR(S) : Antony M. Carr It is certified that error appears in the above-identified patent and that said Letters Patent is hereby corrected as shown below:

Column 14, line 38, please delete "anti cancer" and insert in its place --anti-cancer--.

Column 15, line 43, please delete "described" and insert in its place --described above.--.

Column 15, line 62, please delete "10" and insert in its place --to--.

Column 16, line 6, please delete "...be so with any vehicle" and insert in its place --...be mixed with any vehicle...--.

Column 16, line 9, please delete "...pharmaceutically carrier..." and insert in its place --...pharmaceutically acceptable carrier--.

Column 16, line 38, please delete "breat" and insert in its place --breast--.

Column 16, line 53, please delete "software," and insert in its place --software.--.

Column 17, line 13, please delete "strain" and insert in its place --strain,--.

Column 17, line 17, please delete "at." and insert in its place --al.--.

Column 17, line 21, please delete "rad3.D2230A." and insert in its place --rad3.D2230A,--.

Column 17, line 23, please delete "da not shown)," and insert in its place --(data not shown)--.

Column 17, line 31, please delete "Dull" and insert in its place --null--.

Column 17, line 32, please delete "veils" and insert in its place --cells--.

Column 17, line 48, please delete "methods)." and insert in its place --methods);--.

Column 17, lines 48-49, please delete "(ataxia and lad related)." and insert in its place --(ataxia and rad related).--.

Column 17, line 53, please delete "Tell" and insert in its place --Tel1--.

UNITED STATES PATENT AND TRADEMARK OFFICE
CERTIFICATE OF CORRECTION

PATENT NO.        : 6,632,936 B2
APPLICATION NO. : 09/029047
DATED             : October 14, 2003
INVENTOR(S)       : Antony M. Carr It is certified that error appears in the above-identified patent and that said Letters Patent is hereby corrected as shown below:

Column 17, line 67, please delete "in" and insert in its place --induced--.

Column 18, line 1, please delete "Ogawa." and insert in its place --Ogawa,--.

Column 18, line 1, please delete "1" and insert in its place --I--.

Column 18, line 3, please delete "mote" and insert in its place --more--.

Column 18, line 42, please delete "se" and insert in its place --kinase--.

Column 18, line 50, please delete "protein." and insert in its place --protein,--.

Column 19, line 10, please delete "conserved" and insert in its place --conserved.--.

Column 19, line 12, please delete "(MEC1/SAD3)." and insert in its place --(MEC1/SAD3),--.

Column 19, line 19, please delete "Onion." and insert in its place --function.--.

Column 19, line 20, please delete "has1" and insert in its place --hus1--.

Column 19, line 21, please delete "phenotype" and insert in its place --phenotypes--.

Column 19, line 24, please delete "rad" and insert in its place --rad3--.

Column 19, line 33, please delete "Tellp," and insert in its place --Tel1p,--.

Column 19, line 44, please delete "his defines two sully..." and insert in its place --This defines two structurally...--.

Column 19, line 53, please delete "1992:" and insert in its place --1992;--.

Column 19, line 56, please delete "biomycin" and insert in its place --bleomycin--.

Column 20, line 15, please delete "at." and insert in its place --al.--.

Column 20, line 19, please delete "C-terminsl" and insert in its place --C-terminal--.

UNITED STATES PATENT AND TRADEMARK OFFICE
CERTIFICATE OF CORRECTION

PATENT NO. : 6,632,936 B2
APPLICATION NO. : 09/029047
DATED : October 14, 2003
INVENTOR(S) : Antony M. Carr It is certified that error appears in the above-identified patent and that said Letters Patent is hereby corrected as shown below:

Column 20, line 50, please delete "sequencen" and insert in its place --sequence--.

Column 20, line 61, please delete "kb." and insert in its place --kb).--.

Column 21, line 16, please delete "234" and insert in its place --23<u>4</u>--.

Column 21, line 24, please delete "$_{32}P$" and insert in its place --$^{32}P$--.

Column 24, line 28, please delete "checkpoints." and insert in its place --checkpoints,--.

Signed and Sealed this

Twenty Second Day of April, 2008

JON W. DUDAS
*Director of the United States Patent and Trademark Office*